(12) United States Patent
Napoletano et al.

(10) Patent No.: US 6,492,360 B1
(45) Date of Patent: *Dec. 10, 2002

(54) PHTHALAZINE DERIVATIVES PHOSPHODIESTERASE 4 INHIBITORS

(75) Inventors: Mauro Napoletano, Milan; Gabriele Norcini, Vizzola Ticino; Giancarlo Grancini, Nova Milanese; Franco Pellacini; Gian Marco Leali, both of Milan; Gabriele Morazzoni, Lainate, all of (IT)

(73) Assignee: Zambon Group S.p.A., Vicenza (IT)

( * ) Notice: Subject to any disclaimer, the term of this patent is extended or adjusted under 35 U.S.C. 154(b) by 0 days.

This patent is subject to a terminal disclaimer.

(21) Appl. No.: 09/976,436

(22) Filed: Oct. 15, 2001

Related U.S. Application Data

(63) Continuation of application No. 09/743,813, filed as application No. PCT/EP99/04904 on Jul. 13, 1999, now Pat. No. 6,329,370.

(30) Foreign Application Priority Data

Jul. 21, 1998 (IT) .......................... MI98A1670

(51) Int. Cl.⁷ ................. A61K 31/502; C07D 237/30
(52) U.S. Cl. ............... 514/234.5; 514/248; 544/116; 544/119; 544/237
(58) Field of Search .................. 544/237, 116, 544/119; 514/248, 234.5

(56) References Cited

U.S. PATENT DOCUMENTS 5,089,494 A  2/1992 Iwase et al. ............. 514/248

FOREIGN PATENT DOCUMENTS

| EP | 0 634 404 | 1/1995 |
| EP | 722936 | 7/1996 |
| GB | 2063249 | 6/1981 |
| WO | WO 99/32456 | 7/1999 |

OTHER PUBLICATIONS

Uenishi et al. Chemical Abstracts, vol. 115, No. 28, p. 869, AN 115:256196r, JP 3–106873, May 7, 1991.

Primary Examiner—Richard L. Raymond

(74) Attorney, Agent, or Firm—Oblon, Spivak, McClelland, Maier & Neustadt, P.C.

(57) ABSTRACT

Compounds of formula (I),

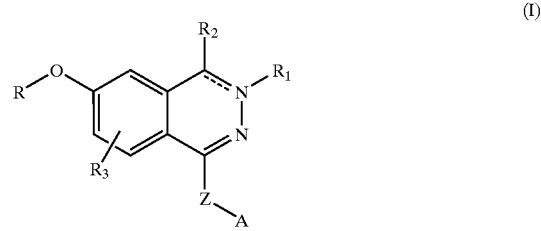

wherein === is a single or double bond; Z is NH, methylene, a $(C_2-C_6)$alkylene chain optionally branched and/or unsaturated and/or interrupted by a $(C_5-C_7)$cycloalkyl residue; A is phenyl or heterocycle optionally substituted or a $COR_4$ group wherein $R_4$ is hydroxy, $(C_1-C_6)$-alkoxy, amino optionally substituted; R is a $(C_1-C_6)$alkyl or polyfluoro$(C_1-C_6)$alkyl group; $R_1$ is absent when === is a double bond or, when === is a single bond, is (a) hydrogen; (b) $(C_1-C_6)$ alkyl optionally substituted; (c) —$COR_6$ wherein $R_6$ is hydrogen, aryl, aryl-$(C_1-C_6)$alkyl, amino optionally alkylated or monohydroxylated, hydroxy, $(C_1-C_4)$ alkoxy, carboxy, $(C_1-C_4)$alkoxycarbonyl, formula (1), or $(C_1-C_4)$alkyl optionally substituted by heterocycle; (d) $(C_1-C_4)$-alkylsulfonyl; $R_2$ represents two hydrogen atoms or a group —O when === is a single bond, or, when === is a double bond, $R_2$ is hydrogen, cyano, $(C_1-C_4)$alkoxycarbonyl, amido, optionally substituted aryl or heterocycle, $(C_1-C_8)$alkyl, $(C_2-C_8)$alkenyl or $(C_2-C_8)$alkynyl optionally branched and/or substituted; aryloxy, heterocyclyloxy, aryl-$(C_1-C_4)$alkoxy, heterocyclyloxy-$(C_1-C_4)$alkoxy, amino substituted by one or two $(C_1-C_4)$-alkyl group(s), arylamino, heterocyclylamino, aryl-$(C_1-C_4)$alkylamino, heterocyclyl-$(C_1-C_4)$-alkylamino; $R_3$ is hydrogen, or a $(C_1-C_8)$alkyl, $(C_2-C_8)$alkenyl or $(C_2-C_8)$alkynyl group optionally substituted, and optionally interrupted; the N→O derivatives of the compounds of formula (I) and the pharmaceutically acceptable salts thereof are PDE 4 inhibitors.

17 Claims, No Drawings

PHTHALAZINE DERIVATIVES PHOSPHODIESTERASE 4 INHIBITORS

This application is a continuation of application Ser. No. 09/743,813 filed Jan. 22, 2001 now U.S. Pat. No. 6,329,370 originally filed as International application No. PCT/EP99/04904, on Jul. 13, 1999. Which was published in English.

The present invention relates to phthalazine derivatives, to the pharmaceutical compositions containing them and to their use as phosphodiesterase 4 inhibitors.

Phosphodiesterases are a family of isoenzymes which constitute the basis of the main mechanism of cAMP (cyclic adenosine-3',5'-monophosphate) hydrolytic inactivation. cAMP has been shown to be the second messenger mediating the biologic response to many hormones, neurotransmitters and drugs [Krebs Endocrinology Proceedings of the 4th International Congress Excerpta Medica, 17–29, 1973]. When the suitable agonist binds to the cell surface, the adenylate cyclase activates and turns $Mg^{2+}$-ATP into cAMP. cAMP modulates the activity of the majority, if not of all the cells contributing to the pathophysiology of various respiratory diseases, both of allergic origin and not. It follows that an increase of the cAMP concentration yields beneficial effects such as airway smooth muscle relaxation, inhibition of the mast cell mediator release (basophil granulose cells), suppression of the neutrophil and basophil degranulation, inhibition of the monocyte and macrophage activation. Thus, compounds able of activating adenylate cyclase or of inhibiting phosphodiesterases could suppress the undesired activation of the airway smooth muscle and of a great number of inflammatory cells.

In the phosphodiesterase family there is a distinct group of isoenzymes, phosphodiesterases 4 (hereinafter PDE 4), specific for the hydrolysis of cAMP in the airway smooth muscle and inflammatory cells (Torphy, "Phosphodiesterase Isoenzymes: Potential Targets for Novel Anti-asthmatic Agents" in New Drugs for Asthma, Barnes, ed. IBC Technical Services Ltd, 1989). Studies carried out on this enzyme show that its inhibition yields not only the airway smooth muscle relaxation, but also the suppression of mastocyte, basophil and neutrophil degranulation, so as the inhibition of the monocyte and neutrophil activation. Thus PDE 4 inhibitors are effective in the therapy of asthma. Such compounds offer a unique approach to the therapy of various respiratory diseases both of allergic origin and not, and possess significant therapeutic advantages over the current therapy.

The excessive or irregular production of tumour necrosis factor (hereinafter $TNF_\alpha$), a cytokine with proinflammatory activity produced by various kind of cells, affects the mediation or the exacerbation of many pathologies such as, for example, the adult respiratory distress syndrome (ARDS) and the chronic pulmonary inflammatory disease. Therefore, compounds able to control the negative effects of $TNF_\alpha$, i.e. the inhibitors of this cytokine, are to be considered as useful against many pathologies.

The patent application EP 722 936 (Eisai) claims, inter alia, compounds of formula

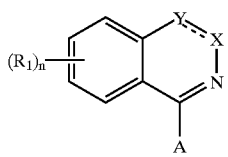

wherein n=0–4; $R_1$ is optionally substituted lower alkoxy, optionally substituted cycloalkyl, or a —$OR_9$ group wherein $R_9$ represents an optionally substituted arylalkyl group; X is —N= or —$NR_6$— wherein $R_6$ is hydrogen, a lower alkyl group, or optionally substituted arylalkyl or heteroarylalkyl groups; Y is —CO or —CB= wherein B is —$NR_7R_8$ wherein one of $R_7$ and $R_8$ may be H and the other an optionally substituted heteroarylalkyl group, or B is hydrogen or an optionally substituted aryl, heteroaryl, arylalkyl or heteroarylalkyl group; A is a hydrogen or halogen atom, or an optionally mono- or disubstituted amino group, an optionally substituted aryl, heteroaryl or heteroarylalkyl group. Among the groups optionally substituting the above mentioned residues, halogen atoms are cited. These compounds are said to be active as inhibitors of cGMP-PDE, i.e. PDE 5, a phosphodiesterase just acting through a cGMP-dependent mechanism and whose field of application is markedly cardiovascular (Schudt C. et al., Phosphodiesterase Inhibitors, Academic Press).

The patent application EP 634 404 (Rhone Poulenc Agriculture) describes, inter alia, phthalazinones of formula

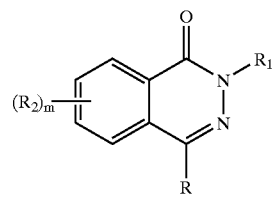

wherein R is an arylalkyl group, in particular pyridyl optionally substituted by halogen atoms; $R_1$ represents an alkyl chain up to 6 carbon atoms or an arylalkyl group, in particular phenyl; $R_2$ represents a phenoxy or benzyloxy group; and m=0–4. These compounds are useful as pesticides.

The U.S. Pat. No. 3,274,185 (Messengill) describes, inter alia, phthalazines of formula

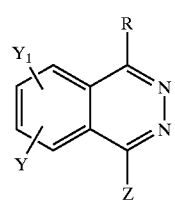

wherein Y and $Y_1$ are independently hydrogen or lower alkoxy; Z is phenyl optionally substituted by halogen or benzyl optionally substituted by lower alkyl or alkoxy; and R is hydrogen. These phthalazines are endowed with sedative and hypotensive activity, without mentioning the mechanism of action.

The U.S. Pat. No. 3,813,384 (Asta-Werke) illustrates, inter alia, benzylphtltalazinones of formula

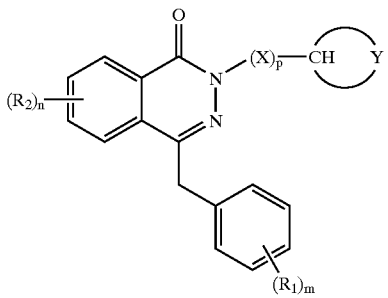

wherein R₁ and R₂ are hydrogen, lower alkoxy or halogen X is an optionally branched alkylene chain; m and n are 1–3; p is 0 or 1; and the group

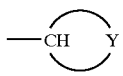

is an optionally substituted ($C_3$–$C_8$) mono, di- or tricyclic residue containing one or two nitrogen atom(s). Such compounds have hystaminolytic action and are useful, for example, in the treatment of asthma. All of the exemplified compounds show a residue

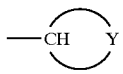

which is a saturated heterocycle.

The patent application WO 97/40020 (Schering AG) describes compounds of formula

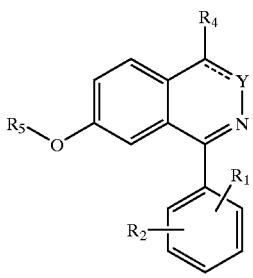

wherein Y is —NR₃— or —N═, R₁ and R₂ are H, lower alkyl, nitro, halogen, amino, lower alkoxy or —CF₃, R₃ is H, —CO— substituted by H, lower alkyl substituted by aryl, amino, lower alkoxy, cycloalkyl or cycloalkoxy, or R₃ is lower alkyl or cycloalkyl, R₄ is H or lower alkoxy, R₅ is lower alkyl. These compounds are said to be uncompetitive antagonists of excitatory amino acids.

The patent application WO 97/48697 (Rhone Poulenc Rorer) describes bicyclic compounds with PDE 4 and TNF$_\alpha$ inhibiting activity represented by a very broad general formula. Phthalazine compounds could be included in the general formula of this patent application, nevertheless none of the exemplified compounds is a phthalazine derivative and this kind of structure is excluded from the claims.

The patent application EP 848 000 (Tanabe Seiyaku) discloses, inter alia, phthalazine derivatives of formula

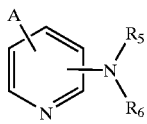

wherein A is one of

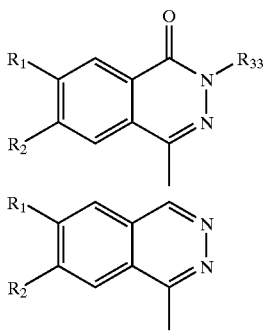

wherein R₁ and R₂ are H, or optionally protected hydroxy; R₃₃ is lower alkyl; R₅ and R₆ are H, amino or may form a heterocycle. These compounds are PDE 4 inhibitors.

It has been now surprisingly found a new class of phthalazine derivatives able to inhibit PDE 4 and TNF$_\alpha$.

Therefore the present invention relates to compounds of formula I

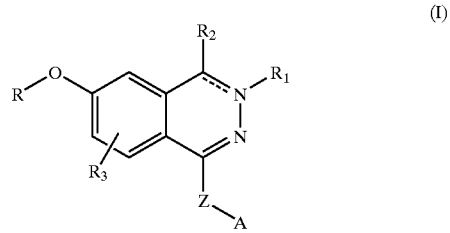

(I)

wherein

═══ is a single or double bond,

Z is NH, methylene, a ($C_2$–$C_6$)alkylene chain optionally branched and/or unsaturated and/or interrupted by a ($C_5$–$C_7$)cycloalkyl residue;

A is phenyl or heterocycle optionally substituted by one or more substituent(s) selected among oxo, nitro, carboxy groups and halogen atoms, or a COR₄ group wherein R₄ is hydroxy, ($C_1$–$C_6$)alkoxy, amino optionally substituted by one or two ($C_1$–$C_6$)alkyl group(s) or by hydroxy;

R is a ($C_1$–$C_6$)alkyl or polyfluoro($C_1$–$C_6$)alkyl group;

R₁ is absent when ═══ is a double bond or, when ═══ is a single bond, is a) hydrogen;

b) ($C_1$–$C_6$)alkyl optionally substituted by aryl, by heterocycle or by a COR₅ group wherein R₅ is hydroxy, ($C_1$–$C_4$)alkoxy or hydroxyamino;

c) —COR₆ wherein R₆ is hydrogen, aryl, aryl-($C_1$–$C_6$) alkyl, amino optionally alkylated or monohydroxylated, hydroxy, ($C_1$–$C_4$)alkoxy, carboxy, ($C_1$–$C_4$)alkoxycarbonyl,

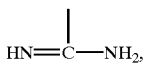

or (C₁–C₄)alkyl optionally substituted by heterocycle;

d) (C₁–C₄)alkylsulfonyl;

R₂ represents two hydrogen atoms or a group =O when ═══ is a single bond, or, when ═══ is a double bond, R₂ is hydrogen, cyano, (C₁–C₄)alkoxycarbonyl, amido, optionally substituted aryl or heterocycle, (C₁–C₈)alkyl, (C₂–C₈)alkenyl or (C₂–C₈)alkynyl optionally branched and/or substituted by aryl or heterocycle; aryloxy, heterocyclyloxy, aryl-(C₁–C₄)-alkoxy, heterocyclyl-(C₁–C₄)alkoxy, amino substituted by one or two (C₁–C₄)alkyl group(s), arylamino, heterocyclylamino, aryl-(C₁–C₄)alkylamino, heterocyclyl-(C₄)alkylamino;

R₃ is hydrogen, or a (C₁–C₈)alkyl, (C₂–C₈)alkenyl or (C₂–C₈)alkynyl group optionally substituted by hydroxy, oxo, aryl or heterocycle, and optionally interrupted by one or more heteroatom(s) or heterogroup(s);

the N→O derivatives of the compounds of formula I and the pharmaceutically acceptable salts thereof.

Preferred compounds according to the present invention are the compounds of formula I wherein ═══ is a double or single bond; and Z is methylene or a (C₂–C₆)alkylene chain.

Still more preferred compounds according to the invention are the compounds of formula I wherein ═══ is a double or single bond; Z is methylene or a (C₂–C₆)alkylene chain; and A is a heterocycle optionally substituted by one or more substituent(s).

Still more preferred compounds according to the invention are the compounds of formula I wherein ═══ is a double or single bond; Z is methylene; and A is pyridine substituted by two substituents.

Within this class a preferred subset is represented by the compounds of formula I-A

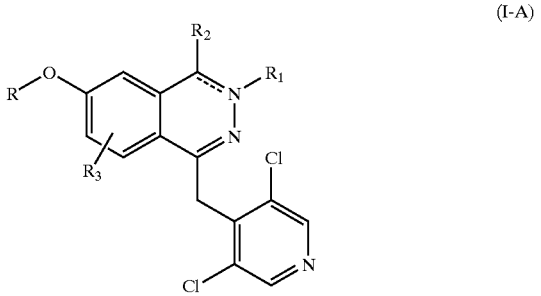

(I-A)

(formula I-Z is methylene, A is 3,5-dichloro-pyridin4-yl).

Still more preferred compounds are the compounds of formula I-A wherein ═══ is a single bond and R₂ represents two hydrogen atoms.

Another class of still more preferred compounds are the compounds of formula I-A wherein ═══ is a double bond; and R₂ is cyano, (C₁–C₄)alkoxycarbonyl, amido, optionally substituted heterocycle, (C₂–C₈)alkenyl or (C₂–C₈)alkynyl optionally substituted by aryl or heterocycle; aryloxy, heterocyclyloxy, arylamino, heterocyclylamino.

Within this class particularly preferred compounds are the compounds of formula I-B

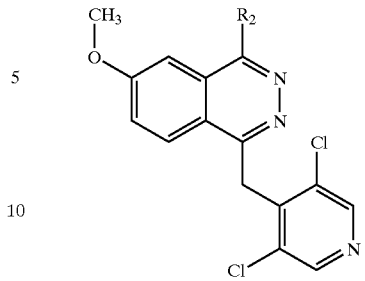

(I-B)

(formula I-A ═══ is a double bond, R₃ is hydrogen, R is methyl) wherein R₂ is a heterocycle.

Specific examples of preferred compounds according to the invention are:

1-(3,5-dichloro-pyridin-4-ylmethyl)-6-methoxy-4-phenyl-phthalazine;

4-(3,5-dichloro-pyridin-4-ylmethyl)-7-methoxy-1H-phthalazin-2-carboxylic acid methyl ester;

benzyl-{3-[1-(3,5-dichloro-pyridin-4-ylmethyl)-6-methoxy-phthalazin-5-yl]-prop-2-ynyl}-methyl-amine;

1-(3,5-dichloro-pyridin-4-ylmethyl)-6-methoxy-5(5-morpholin-4-yl-pent-1-ynyl)-phthalazine dihydrochloride;

3-[1(3,5-dichloro-pyridin-4-ylmethyl)-6-methoxy-phthalazin-5-yl]-prop-2-yn-1-ol;

1-(3,5-dichloro-pyridin-4-ylmethyl)-6-methoxy-4-morpholin-4-yl-phthalazine;

1-(3,5-dichloro-pyridin-4-ylmethyl)-6-methoxy-4-[1,2,4]triazol-1-yl-phthalazine.

The compounds of formula I may have one or more asymmetric centre(s) and thus be in form of stereoisomers. Object of the present invention are compounds of formula I in form of stereoisomeric mixtures so as of single stereoisomers.

The compounds of formula I are active as PDE 4 and TNFα inhibitors and thus are used as therapeutic agents in allergic and inflammatory pathologies such as, for example, COPD, asthma and allergic rhinitis.

As heterocycle pyrrole, imidazole, pyrazole, pyridine, pyrazine, pyrimidine, pyridazine, piperazine, triazole, morpholine, pyrrolidine, pyrroline, imidazoline, pyrazoline, pyrazolidine, imidazolidine, piperidine, furan, pyran, thiazole, isothiazole, isoxazole, thiophene and the like are particularly meant.

Halogen atom means fluorine, chlorine, bromine or iodine atom.

Specific examples of alkyl groups are methyl, ethyl, n-propyl, i-propyl, n-butyl, s-butyl, tert-butyl, n-pentyl, 1-methyl-butyl, 2-methyl-butyl, 3-methyl-butyl, 3-methyl-2-butyl, n-hexyl, heptyl, octyl and the like. As (C₅–C₇)cycloalkyl group, cyclopentyl, cyclohexyl and cycloheptyl are meant, while aryl means an aromatic ring or system of 6–10 carbon atoms and specific examples of aryl and aryl (C₁–C₁₀)alkyl are phenyl, benzyl, phenethyl, phenyl-pentyl, naphthyl, indanyl, indanyl-pentyl and the like.

The oxidised form N→O, if present, may involve both the nitrogen atoms present on the phthalazine ring and those present on A when it is a heterocyclic substituent. Pharmaceutically acceptable salts of the compounds of formula I are those with organic and inorganic acids, such as, for example, hydrochloric, hydrobromic, hydroiodic, nitric, sulfuric, phosphoric, acetic, benzoic, maleic, fumaric, succinic, tartaric, citric, aspartic, methanesulfonic, 3,7-di-tert-butylnaphthalen-1,5-disulfonic (dibudinic acid) or with inorganic bases such as, for example, sodium or potassium hydroxide, sodium bicarbonate.

The synthesis of the compounds of formula I proceeds according to methods known to the skilled in the art. For example, it can start from a compound of formula II

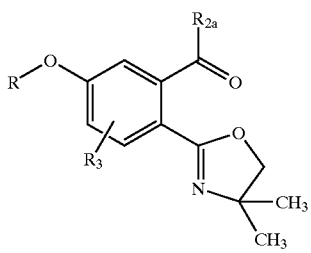

(II)

wherein R and $R_3$ are as defined above, and $R_{2a}$ is hydrogen, optionally substituted aryl or heterocycle or $(C_1-C_8)$alkyl, $(C_2-C_8)$alkenyl or $(C_2-C_8)$alkynyl optionally substituted by aryl or heterocycle, which can be prepared by different routes. For example, the treatment of a compound of formula III

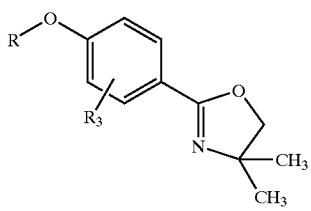

(III)

wherein R and $R_3$ are as defined above, with a strong base, for example, n-butyl lithium, gives the compound of formula IIIa

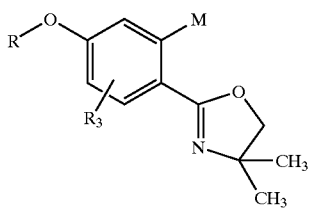

(IIIa)

wherein R and $R_3$ are as defined above and M is lithium or sodium, which treated with a formyl electrophile provides a compound of formula II wherein $R_{2a}$ is hydrogen. Such compound can be turned into a compound of formula II wherein $R_2$. is other than hydrogen by treatment with a suitable organometal, for example, a Grignard reagent, to give a compound of formula IV

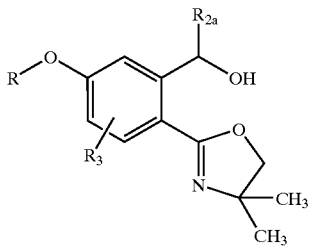

(IV)

wherein R, $R_{2a}$ and $R_3$ are as defined above, which by oxidation, for example, with a pyridine-$SO_3$ complex, DMSO and triethylamine, gives the desired compound II.

The compound of formula IV can also be obtained starting from a compound of formula IIIa by reaction with an aldehyde of formula V

$R_{2a}$—CHO (V)

wherein $R_{2a}$ is as defined above, used in molar excess as compared to the compound IIIa.

Also, a compound of formula II wherein $R_{2a}$ is other than hydrogen can be synthesised directly from a compound of formula IIIa by transmetallation with a suitable salt, for example zinc chloride, and subsequent reaction with an acyl chloride in the presence of a transition metal catalyst, for example, palladium.

After clearing of the oxazoline group of the compound of formula II, the treatment with hydrazine, in a protic solvent, is effected to give a phthalazinone of formula VI

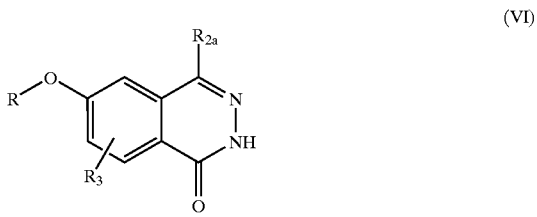

(VI)

wherein R, $R_{2a}$ and $R_3$ are as defined above, which treated with a halogenating agent such as, for example, phosphorous oxychloride gives a compound of formula VII

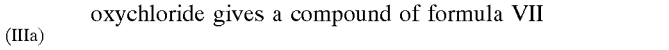

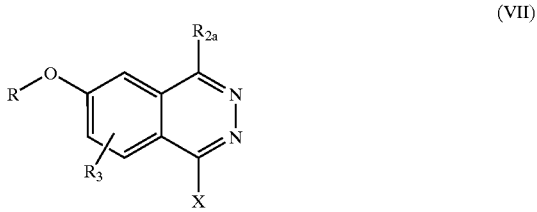

(VII)

wherein R, $R_{2a}$ and $R_3$ are as defined above, and X is a bromine or chlorine atom. This, by treatment with a compound of formula VIII

A—Z—Y (VIII)

wherein A and Z are as defined above and Y is a metal such as, for example, Li, Na, Mg or a transition metal complex, gives a compound of formula I wherein $R_2$ has the meanings listed above when === is a double bond and $R_1$ is absent.

When a compound of formula I wherein $R_1$ is present is desired, a compound of formula I wherein === is a double bond and $R_2$ is hydrogen is treated according to methods known to the skilled in the art. For example, by reduction with hydrogen in the presence of Pd/C or $PtO_2$, a compound of formula I wherein $R_1$ is hydrogen is obtained, which by subsequent treatment with a suitable sulfonating or acylating agent, gives a compound of formula I wherein $R_1$ is $(C_1-C_4)$ alkylsulfonyl or $-CO-R_6$ wherein $R_6$ is as defined above.

Alternatively, the compounds of formula I can be obtained starting from the acid of formula VIII

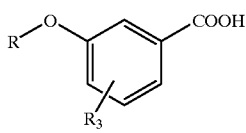

(VIII)

wherein R and $R_3$ are as defined above, which by reaction with formaldehyde and HCl gives a compound of formula IX

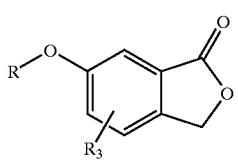

(IX)

wherein R and $R_3$ are as defined above. This compound is halogenated, for example with N-bromosuccinimide in the presence of a catalyst such as benzoyl peroxide or 2,2' azoisobutyronitrile, to give a compound of formula X

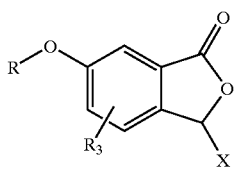

(X)

wherein R, $R_3$ and X are as defined above, which is treated with triphenylphosphine to give a compound of formula XI

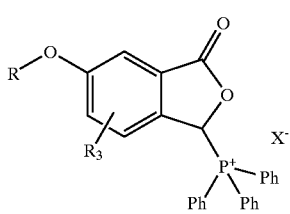

(XI)

wherein R, $R_3$ and X are as defined above, which is reacted with an aldehyde of formula XII

A—Z'—CHO (XII)

wherein A is as defined above and Z' is methylene or a $(C_2-C_5)$alkylene chain optionally ranched and/or unsaturated and/or interrupted by a $(C_5-C_7)$cycloalkyl residue, or is absent, in the presence of an organic base such as, for example triethylamine, to give a compound of formula XIII

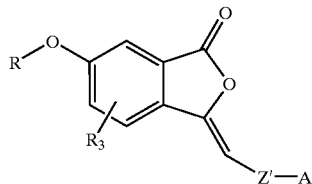

(XIII)

wherein R, $R_3$, Z' and A are as defined above. This compound is reacted with hydrazine to give a compound of formula I wherein $R_1$ is hydrogen, $R_2$ is a group =O, and Z is methylene or a $(C_2-C_5)$alkylene chain optionally branched and/or unsaturated and/or interrupted by a $(C_5-C_7)$ cycloalkyl residue, but not on the first carbon atom. The reaction of this compound of formula I with a suitable alkyl halide or sulfonate in the presence of a base, for example sodium hydride, gives a compound of formula I wherein $R_1$ is a substituent other than hydrogen.

The compound of formula I wherein $R_1$ is hydrogen can provide also other compounds of formula I wherein Z is methylene or a $(C_2-C_5)$alkylene chain optionally branched and/or unsaturated and/or interrupted by a $(C_5-C_7)$ cycloalkyl residue, but not on the first carbon atom. For example, it is reacted with a halogenating agent such as, for example $POCl_3$ or $POBr_3$, to give an intermediate of formula XIV

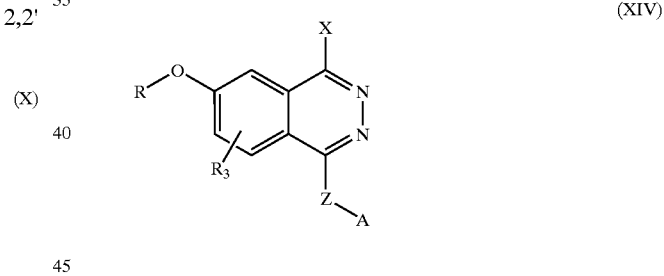

(XIV)

wherein A, R, $R_3$, Z and X are as defined above, which is then subdued to a coupling reaction in the presence of a catalyst, such as for example palladium, or to an aromatic nucleophilic substitution, to give a compound of formula I wherein $R_2$ has the meanings listed above when === is a double bond and Z is methylene or a $(C_2-C_5)$alkylene chain optionally branched and/or unsaturated and/or interrupted by a $(C_5-C_7)$cycloalkyl residue, but not on the first carbon atom.

As for the substituent $R_3$ when other than hydrogen, it can be already present in the starting products of the various above synthetic routes or can be introduced and/or modified during the process according to methods known to the skilled in the art. For example, when $R_3$ is $(C_2-C_8)$alkenyl or $(C_2-C_8)$alkynyl optionally substituted by aryl or heterocycle, it can be hydrogenated to give the corresponding $(C_1-C_8)$alkyl or $(C_2-C_8)$alkenyl residue. Said hydrogenation is effected according to methods known to the skilled in the art.

Alternatively, a compound of formula XV

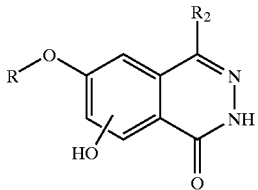
(XV)

wherein R and $R_2$ are as defined above, is activated on the hydroxy moiety, for example with triflic anhydride, to give a compound of formula XVI

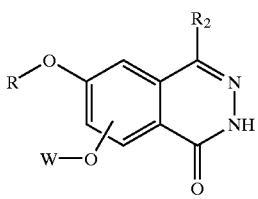
(XVI)

wherein R and $R_2$ are as defined above, and W is an activating group. This compound is then subdued to a coupling reaction in the presence of a catalyst, for example palladium, to give the desired compound of formula VI which is then worked up as above described to give the compound of formula I.

The compound of formula XV can be obtained, for example, starting from a compound of formula XVII

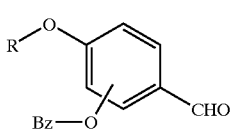
(XVII)

wherein R is as defined above and Bz is a benzyl group, which is oxidised, for example with potassium permanganate and tetrabutylammonium bromide, to give an acid of formula XVIII

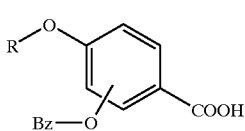
(XVIII)

wherein R and Bz are as defined above, which by treatment, for example, with thionyl chloride, is turned into the corresponding acyl halide of formula XIX

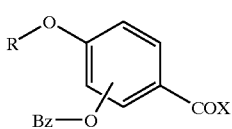
(XIX)

wherein R, Bz and X are as defined above. This is reacted with diethylamine in at least equimolar amount, to give a benzamide of formula XX

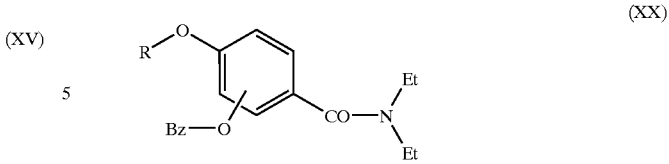
(XX)

wherein R and Bz are as defined above, which is reacted with dimethylformamide in the presence of a strong organic base such as, for example, butyl lithium, tert-butyl lithium, sec-butyl lithium, optionally in the presence of a ligand such as, for example tetramethylethylendiamine, to give a compound of formula XXIa

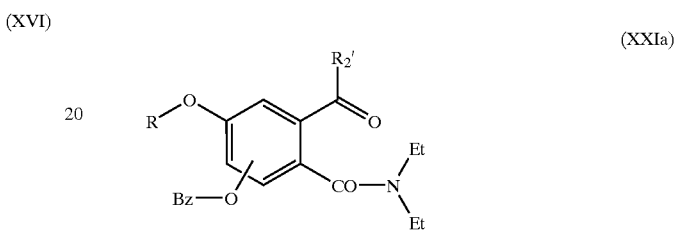
(XXIa)

wherein R and Bz are as defined above, and $R_2'$ is hydrogen. This compound is reacted with hydrazine in acetic acid to give the compound of formula XXII

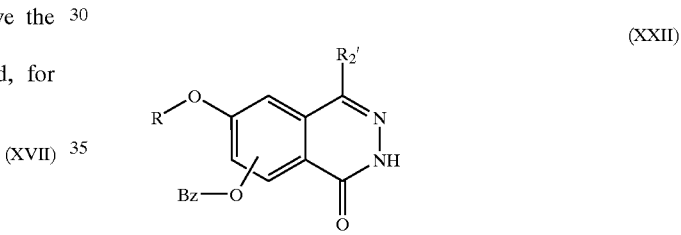
(XXII)

wherein R, Bz and $R_2'$ are as defined above, which is debenzylated with HCl in acetic acid to give the compound of formula XV.

The compound XXII, treated according to the methods already reported for analogous compounds (for example compound XVI) can also provide compound XXIII

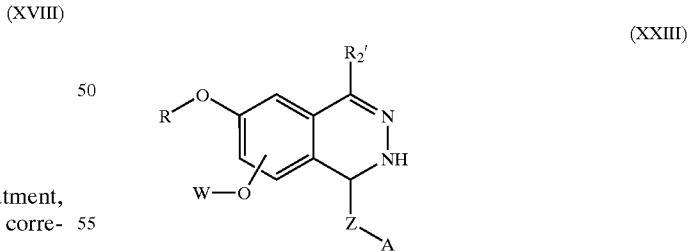
(XXIII)

wherein R, $R_2'$, W, Z and A are as defined above, which is reacted under coupling conditions with palladium to provide a compound of formula I wherein $R_2$ is hydrogen.

An alternative for obtaining a compound of formula I wherein $R_2$ is other than hydrogen foresees that the compound of formula XXIa is treated with $R_2''$-magnesium halide, for example chloride, or $R_2''$-lithium, wherein $R_2''$ has the meanings of $R_2$ above said but hydrogen, to give a compound of formula XXIV

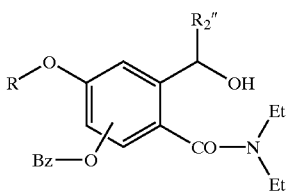

(XXIV)

wherein R, Bz and $R_2''$ are as defined above. The compound of formula XXIV is treated with a suitable oxidising agent such as, for example, pyridinium-chlorochromate and provides a compound of formula XXIb

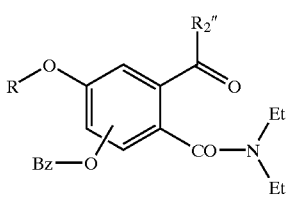

(XXIb)

wherein R and $R_2''$ are as defined above. The compounds of formula XXIa or XXIb are treated with acetic acid in acidic medium to give a compound of formula XXV

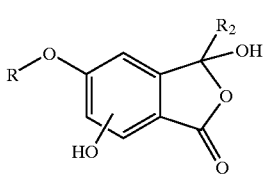

(XXV)

wherein R and $R_2$ are as defined above, which is reacted with hydrazine to give the phthalazinone of formula XV.

The synthesis of the N-oxide of the compounds of formula I is effected by treating the compounds of formula I with peracids such as, for example, m-chloroperbenzoic acid.

The preparation of the salts of the compounds of formula I is effected according to known methods.

The compounds of formula I are PDE 4 inhibitors as showed by the in vitro enzymatic inhibition activity tests (example 147), and also are able to inhibit the $TNF_\alpha$ release (example 148). Comparisons with the following compounds were made: 6,7-dimethoxy-4-(pyridin-4-ylmethyl-2H-phthalazin-1-one (reference 1) and 6,7-dimethoxy-4-(piperidin-4-ylmethyl)-2H-phthalazin-1-one (reference 2) comprised by the general formula of the already cited patent application EP 722 936 (Eisai) and selected in view of the structural affinity with the compounds of the present invention. The reference compounds, though chemically similar, showed to be inactive as PDE 4 inhibitors.

Furthermore the compounds of the present invention did not show any activity on PDE 3 and 5 enzymes (example 149).

It is apparent how these selectivity and specificity features combined with the lack of activity on the cardiovascular system make the compounds of formula I specifically suitable for treating pathologies involving PDE 4 and $TNF_\alpha$ such as asthma, the chronic obstructive pulmonary disease (COPD), the adult respiratory distress syndrome (ARDS), allergic rhinoconjunctivitis, psoriasis, atopic dermatitis, rheumatoid arthritis, septic shock, ulcerative cholitis, even if in the present contest the interest is particularly focused on the respiratory pathologies. Especially, the compounds of the invention are useful in the treatment of allergic and inflammatory diseases and above all in the therapy of COPD, asthma and allergic rhinitis.

The therapeutic doses shall be generally from 0.1 to 1,000 mg a day and from 1 to 200 mg by oral route for single administration.

A further object of the present invention are the pharmaceutical compositions containing a therapeutically effective amount of the compounds of formula I or pharmaceutically acceptable salts thereof in admixture with a suitable carrier.

The pharmaceutical compositions object of the invention may be liquid, suitable for the enteral or parenteral administration, and, preferably, solid such as tablets, capsules, granulates, suitable for the oral administration, or in a form suitable for the transdermal and inhalatory administration.

The preparation of the pharmaceutical compositions object of the invention can be effected according to common techniques.

For better illustrating the invention the following examples are provided.

The $^1$H-NMR spectra were run at 200 MHz on a Varian instrument; δ are in parts per million.

EXAMPLE 1

2-(4-Methoxy-phenyl)-4,4-dimethyl-4,5-dihydro-oxazole

A solution of 2-amino-2-methyl-propan-1-ol (104.5 g, 1.17 moles) in $CH_2Cl_2$ (400 ml) under $N_2$ was dropwise added in 30 minutes with a solution of 4-methoxybenzoyl chloride (100 g, 0.59 moles) in $CH_2Cl_2$ (500 ml), keeping the temperature at about 8° C. with water/ice. After 3 hours under stirring the precipitate was filtered over celite and washed with $CH_2C_2$. The organic phase was stirred under $N_2$ at 2° C. and dropwise added with thionyl chloride (123 ml, 1.77 moles), keeping the temperature below 10° C. At the end of the dropping the reaction mixture was stirred overnight, then concentrated under vacuum. The residue was taken up in 5% HCl and twice extracted with ethyl ether. The extracts were in turn extracted with 5% HCl. The aqueous phase was alkalinised with concentrated NaOH and extracted three times with ethyl ether, then anhydrified and concentrated under vacuum. The crude was distilled at 95–98° C. (30 Pascal) to give 106.43 g of the title compound (yield: 87.6%).

$^1$H-NMR (CDCl$_3$) δ: 7.87–6.84(m,4H); 4.04(s,2H); 3.80 (s,3H); 1.34(s, 6H).

EXAMPLE 2

2-(4,4-Dimethyl-4,5-dihydro-oxazol-2-yl)-5-methoxy-benzaldehyde

In dry environment under $N_2$, 2-(4-methoxy-phenyl)-4,4-dimethyl-4,5-dihydro-oxazole (20 g, 0.097 mole), prepared as described in example 1, was dissolved in ethyl ether (200 ml) and added at −2° C. with n-butyl lithium (44 ml, 0.11 mole), keeping the temperature below 5° C. The mixture was stirred and after 4 hours added with DMF (15.4 g, 16.3 ml, 0.21 mole). After stirring overnight at room temperature, the mixture was cooled and extracted with water/ice. The aqueous phase was extracted again with ethyl ether. The organic phase was washed with water/NaCl, discoloured with charcoal, anhydrified and concentrated under vacuum to give 19 g of the title compound (yield: 84%).

$^1$H-NMR (CDCl$_3$) δ: 10.75(s,1H); 7.84–7.05(m,3H); 4.10 (s,2H); 3.86(s,3H); 1.37(s,6H).

EXAMPLE 3

6-Methoxy-2H-phthalazin-1-one

A solution of 2-(4,4-dimethyl-4,5-dihydro-oxazol-2-yl)-5-methoxy-benzaldehyde (2 g, 8.58 mmoles), prepared as described in example 2, in 30 ml of a mixture of water (5 ml), ethanol (50 ml) and concentrated H$_2$SO$_4$ (4 ml) up to 100 ml with ethanol, was stirred under reflux for 20 hours, then concentrated to small volume, taken up in water, extracted with ethyl ether and the organic phase was washed with water, anhydrified and brought to dryness. The resultant oil was dissolved in acetic acid (14 ml) and dropwise added, under N$_2$, with hydrazine monohydrate (1.25 ml, 25.7 mmoles) dissolved in acetic acid (6 ml). The mixture was stirred for 3.5 hours at room temperature, then at 80° C. for 4 hours, then cooled, brought to almost complete dryness, taken up in water, neutralised with NaHCO$_3$, extracted more times with CH$_2$Cl$_2$. The organic phases were washed with water, anhydrified and concentrated. The residue was triturated in CH$_2$Cl$_2$ (10 ml) and filtered to give 1.1 g of the title compound (yield: 73.4%). m.p.: 200–205° C.

$^1$H-NMR (DMSO) δ: 12.50(s-broad,1H); 8.26(s,1H); 8.14–7.37(m,3H); 3.91(s,3H).

EXAMPLE 4

1-Chloro-6-methoxy-phthalazine

A suspension of 6-methoxy-2H-phthalazin-1-one (6.4 g, 36.3 mmoles), prepared as described in example 3, in acetonitrile (65 ml) under stirring and dry N$_2$ at room temperature, was dropwise added with phosphorous oxychloride (6.8 ml, 73 mmoles), then the mixture was refluxed. After 3 hours the mixture was concentrated, taken up in water, neutralised with NaHCO$_3$ and extracted more times with CH$_2$Cl$_2$. The organic phases were washed with water, anhydrified and concentrated to give 6.94 g of the title compound (yield: 98.3%). m.p.: 181–183° C.

$^1$H-NMR (CDCl$_3$) δ: 9.33(s,1H); 8.21–7.20(m,3H); 4.00 (s,3H).

EXAMPLE 5

1-(3,5-Dichloro-pyridin-4-ylmethyl)-6-methoxy-phthalazine (Compound 1)

A solution of 3,5-dichloro-4-methyl-pyridine (11.32 g, 70 mmoles) in dry DMF (100 ml) was stirred under N$_2$ at room temperature, then added with 60% NaH in oil (2.8 g, 70 mmoles). After 1 hour at room temperature a solution of 1-chloro-6-methoxy-phthalazine (6.8 g, 35 mmoles), prepared as described in example 4, in DMF (250 ml) was added. The mixture was left at room temperature for 20 hours, then poured into water/ice (pH≅8) and extracted more times with CH$_2$Cl$_2$. The organic phases were washed with water, anhydrified and brought to dryness to give a solid which was triturated in isopropyl ether (100 ml) and filtered. The mother liquors were dried and the residue flash chromatographed with ethyl acetate to give 8.9 g of the title compound (yield: 79.5%). m.p.: 173–175° C.

$^1$H-NMR (CDCl$_3$) δ: 9.32(s,1H); 8.50(s,2H); 8.11(d,1H, J=9.0 Hz); 7.56 (dd,1H); 7.20(d, 1H,J=2.6 Hz); 4.90(s,2H); 4.00(s,3H).

EXAMPLE 6

1(3,5-Dichloro-pyridin-4-ylmethyl)-6-methoxy-phthalazine 3-oxide (Compound 2)

A solution of 1-(3,5-dichloropyridin-4-ylmethyl)-4-methoxy-phthalazine (1 g, 3.13 mmoles), prepared as described in example 5, in dry CH$_2$Cl$_2$ (15 ml), under stirring and N$_2$ at room temperature, was added with m-chloroperbenzoic acid (0.81 g, 4.7 mmoles). After 1 hour the mixture was washed with 10% NaOH and water, anhydrified and brought to dryness. The residue was flash chromatographed (eluent: ethyl acetate 100%, then ethyl acetate/CH$_3$OH 8:2) to give a solid which was crystallised from acetic acid/ethyl acetate to give 0.32 g of the title compound (yield: 31%). m.p.>230° C.

$^1$H-NMR (CDCl$_3$) δ: 8.70(s,2H); 8.66(s,1H); 8.37(d,1H, J9.1 Hz); 7.42(dd,1H); 7.34(d,1H,J=2.4 Hz); 4.91(s,2H); 3.94(s,3H).

EXAMPLE 7

1-(3,5-Dichloro-1-oxy-pyridin-4-ylmethyl)-6-methoxy-phthalazine 3-oxide (Compound 3)

A solution of 1-(3,5-dichloro-pyridin-4-ylmethyl)-6-methoxy-phthalazine (1 g, 3.12 mmoles), prepared as described in example 5, in dry CHCl$_3$ (15 ml), under stirring and N$_2$ at room temperature, was added with m-chloroperbenzoic acid (1.62 g, 9.37 mmoles) and refluxed. After 3 hours the mixture was cooled and the solid was separated. The mother liquors were dried and the residue flash chromatographed (eluent: CH$_2$Cl$_2$/CH$_3$OH 95:5, then 9:1) to give 0.68 g of the title compound (yield: 62%). m.p.>230° C.

$^1$H-NMR (CDCl$_3$) δ: 8.41(s,1H); 8.18(s,21H); 8.00(d,1H, J=9.2 Hz); 7.32(dd,1H); 6.93(d,1H,J=2.5 Hz); 4.72(s,2H); 3.98(s,3H).

EXAMPLE 8

1-[2-(4,4-Dimethyl-4,5-dihydro-oxazol-2-yl)-5-methoxy-phenyl]-propan-1-one

A solution of 2-(4-methoxy-phenyl)-4,4-dimethyl-4,5-dihydro-oxazole (4.5 g, 21.9 mmoles), prepared as described in example 1, in dry ethyl ether (90 ml), under stirring and N$_2$ at 0° C., was added with 2.5M n-butyl lithium (9.6 ml, 24.1 mmoles) in hexane. The reaction went on for 4 hours. In another flask a suspension of ZnCl$_2$ (4.48 g, 33 mmoles) in dry ethyl ether (60 ml) was prepared and, at 0° C., dropwise added with the solution of the lithium derivative. At the end of the addition, the mixture was left at room temperature for 1.5 hours, then cooled to 0° C. and sequentially added with palladium acetate (0.25 g, 1.09 mmoles), triphenylphosphine (0.57 g, 2.19 mmoles) and, after 5 minutes, with propanoyl chloride (2.13 g, 23.02 mmoles). The mixture was left to stand for 20 hours, then poured into water/ice and extracted with ethyl acetate. The organic phase was anhydrified, discoloured and brought to dryness to give 6.6 g of the title compound (yield: 75%)

$^1$H-NMR (CDCl$_3$) δ: 7.87–6.73(m,3H); 4.00(s,2H); 3.80 (s,3H); 2.71(q,2H); 1.31(s,6H); 1.16(t,3H,J=7.4 Hz).

EXAMPLE 9

4-Ethyl-6-methoxy-2H-phthalazin-1-one

A solution of 1-[2-(4,4-dimethyl-4,5-dihydro-oxazol-2-yl)-5-methoxy-phenyl]-propan-1-one (6.4 g, 15.9 mmoles), prepared as described in example 8, in 110 ml of a mixture of water (10 ml), ethanol (100 ml) and concentrated H$_2$SO$_4$ (8 ml) up to 200 ml with ethanol, was stirred under N$_2$ and reflux for 20 hours, then concentrated, taken up in water and extracted more times with ethyl ether. The organic phases were washed with water, anhydrified and brought to dryness to give an oil which was dissolved in acetic acid and added, at 15° C., with hydrazine monohydrate (1.56 g, 31.2 mmoles) in acetic acid (10 ml). At the end of the addition, the mixture was heated to 80° C. and, after 20 hours, brought to small volume, taken up in water, neutralised with NaHCO$_3$ and extracted more times with CHCl$_3$. The organic phases were anhydrified and brought to dryness to give a residue, which was flash chromatographed (eluent: hexane/ethyl acetate 9:1, then 7:3). There were thus obtained 1.34 g of the title compound (yield: 44%). m.p.: 230–235° C.

$^1$H-NMR (CDCl$_3$) δ: 12.3(s-broad,1H); 8.18–7.27(m, 3H); 3.92(s,3H); 2.93(q,2H); 1.24(t,3H,J=7.5 Hz).

EXAMPLE 10

1-Chloro-4-ethyl-6-methoxy-phthalazine

A suspension of 4-ethyl-6-methoxy-2H-phthalazin-1-one (1.3 g, 6.76 mmoles), prepared as described in example 9, in dry acetonitrile (20 ml), under stirring and dry N$_2$ at room temperature, was added with phosphorous oxychloride (2.07 g, 13.52 mmoles). The mixture was refluxed and after 2 hours cooled, brought to small volume, taken up in water, added with Na$_2$CO$_3$ in excess and extracted three times with CH$_2$Cl$_2$. The organic phases were anhydrified and brought to dryness to give 1.34 g of the title compound (yield: 89%).

$^1$H-NMR (CDCl$_3$) δ: 820–7.54(m,3H); 4.01(s,3H); 3.30 (q,2H); 1.36(t,3H,J=7.4 Hz).

EXAMPLE 11

1-(3,5-Dichloro-pyridin-4-ylmethyl)-4-ethyl-6-methoxy-phthalazine (Compound 4)

Operating substantially as described in example 5 starting from 3,5-dichloro-4-methyl-pyridine (1.75 g, 10.77 mmoles), dry DMF (20 ml), 60% NaH in oil (0.26 g, 10.77 mmoles) and 1-chloro-4-ethyl-6-methoxy-phthalazine (1.2 g, 5.39 mmoles), prepared as described in example 10, in DMF (25 ml), 0.66 g of the title compound were obtained (yield: 36%). m.p.: 136–138° C.

$^1$H-NMR (CDCl$_3$) δ: 8.48(s,2H); 8.12(d,1H,J=9 Hz); 7.52 (dd,1H); 7.33(d,1H,J=2.5 Hz); 4.85(s,2H); 4.00(s,3H); 3.27 (q,2H); 1.47(t,3H,J=7.3 Hz).

EXAMPLE 12

[2-(4,4-Dimethyl-4,5-dihydro-oxazol-2-yl)-5-methoxy-phenyl]-phenyl-methanone

A solution of 2-(4-methoxy-phenyl)-4,4-dimethyl-4,5-dihydro-oxazole (4.5 g, 21.9 mmoles), prepared as described in example 1, in dry ethyl ether (90 ml), under stirring and dry N$_2$ at 0° C., was added with 2.5M n-butyl lithium (9.6 ml, 24.1 mmoles) in hexane, and the reaction went on for 4 hours. In another flask a suspension of ZnCl$_2$ (4.48 g, 33 mmoles) in dry ethyl ether (60 ml) was prepared and dropwise added with the solution of the lithium derivative at 0° C. and, after 1 hour, with benzoyl chloride (3.24 g, 23.02 mmoles). The mixture was left at room temperature for 3 hours, then added with bis(triphenylphosphine)palladium chloride (280 mg) and, after 3 days, poured into water/ice and extracted with ethyl acetate. The organic phases were washed with water, anhydrified and brought to dryness to give 3.5 g of the title compound (yield: 52%).

$^1$H-NMR (CDCl$_3$) δ: 7.86–6.95(m,8H); 3.84(s,3H); 3.51 (s,2H); 0.98(s,6H).

EXAMPLE 13

6-Methoxy-4-phenyl-2H-phthalazin-1-one

A suspension of [2-(4,4-dimethyl-4,5-dihydro-oxazol-2-yl)-5-methoxy-phenyl]-phenyl-methanone (34 g, 11 mmoles), prepared as described in example 12, in 3N HCl (45 ml) was refluxed under stirring for 2 days, then added with 36% HCl (10 ml). After 20 hours the mixture was cooled and extracted more times with CHCl$_3$. The organic phases were anhydrified and brought to dryness. The residue was dissolved in acetic acid and treated with hydrazine monohydrate (0.96 g, 19.24 mmoles) in acetic acid (7 ml). The mixture was heated to 80° C. under dry N$_2$ and stirring for 20 hours, then brought to small volume, poured into water, neutralised with NaHCO$_3$ in excess and extracted with CHCl$_3$. The organic phases anhydrified and brought to dryness yielded 0.6 g of the title compound (yield: 37%). m.p.: 230–235° C.

$^1$H-NMR (DMSO) δ: 12.71(s,1H); 8.29–7.00(m,8H); 3.8 (s,3H).

EXAMPLE 14

1-Chloro-6-methoxy-4-phenyl-phthalazine

Operating as described in example 4 starting from 6-methoxy-4-phenyl-2H-phthalazin-1-one (0.6 g, 2.38 mmoles), prepared as described in example 13, in acetonitrile (10 ml) and phosphorous oxychloride (0.44 ml, 4.76 mmoles), 0.4 g of the title compound were obtained (yield: 62.5%).

$^1$H-NMR (DMSO) δ: 8.33–7.26(m,8H); 3.88(s,3H).

EXAMPLE 15

1-(3,5-Dichloro-pyridin-4-ylmethyl)-6-methoxy-4-phenyl-phthalazine (Compound 5)

Operating as described in example 5 starting from 3,5-dichloro-4-methyl-pyridine (0.45 g, 2.81 mmoles) in dry DMF (10 ml), 60% NaH (67 mg, 2.81 mmoles) and 1-chloro-6-methoxy-4-phenyl-phthalazine (0.38 g, 1.4 mmoles), prepared as described in example 14, in DMF (10 ml), 0.26 g of the title compound were obtained (yield: 47.3%). m.p.: 206–208° C.

$^1$H-NMR (CDCl$_3$) δ: 8.51(s,2H); 8.22–7.39(m,8H); 4.94 (s,2H); 3.87(s,3H).

EXAMPLE 16

[2-(4,4-Dimethyl-4,5-dihydro-oxazol-2-yl)-5-methoxy-phenyl]-phenyl-methanol

Magnesium turnings for Grignard (0.12 g, 4.71 mmoles) in ethyl ether (8 ml) were put under N$_2$ and stirring at room temperature. Ethyl bromide (2 drops) and then, slowly, bromobenzene (0.52 ml, 4.93 mmoles) in ethyl ether (10 ml) and 1,2-dibromoethane (2 drops) were added. The temperature arose to reflux and was kept as such for 1 hour. The mixture was treated with 2-(4,4-dimethyl-4,5-dihydro-oxazol-2-yl)-5-methoxy-benzaldehyde (1 g, 4.29 mmoles), prepared as described in example 2, and kept at reflux for a further hour, then cooled, poured into water/ice and extracted more times with ethyl acetate. The organic phases were washed with water, anhydrified and brought to dryness to give 1.44 g of the title compound (yield: 98%).

$^1$H-NMR (CDCl$_3$) δ: 8.23(s-broad,1H); 7.80–6.67(m, 8H); 5.86(s-broad,1H); 4.15–3.79(m,2H); 3.76(s,3H); 1.31 and 0.96(2s,6H).

EXAMPLE 17

1-[2-(4,4-Dimethyl-4,5-dihydro-oxazol-2-yl)-5-methoxy-phenyl]-5-phenyl-pentan-1-ol A solution of 2-(4-methoxy-phenyl)-4,4-dimethyl-4,5-dihydro-oxazole (1.85 g, 9 mmoles), prepared as described in example 1, in dry ethyl ether (37 ml), at 0° C. was added with 2.5M n-butyl lithium (4 ml, 9.9 mmoles) in hexane, keeping the temperature below 5° C. The mixture was left at 0° C. for 4 hours, then dropwise added with a solution of 5-phenyl-pentanale (3.25 g, 20 mmoles) in dry ethyl ether (10 ml), keeping the temperature below 5° C. The mixture was kept at room temperature for 2 days, then poured into water/ice. The phases were separated and the aqueous one was extracted again with ethyl ether. The organic ones were discoloured with charcoal, anhydrified and concentrated to give an oil which was purified by flash chromatography (eluent: petrolatum/ethyl acetate 8:2, then 7:3) to give 1.17 g of the title compound (yield: 35%).

$^1$H-NMR (CDCl$_3$) δ: 7.83–6.75(m,8H); 4.65–4.58(m,1H); 4.12–4.02(m,2H); 3.81(s,3H); 2.63–2.55(m,2H); 2.00–1.28(m,6H); 1.36(s,6H).

EXAMPLE 18

1-[2-(4,4-Dimethyl-4,5-dihydro-oxazol-2-yl)-5-methoxy-phenyl]-5-pentan-1-one

A solution of 1-[2-(4,4-dimethyl-4,5-dihydro-oxazol-2-yl)-5-methoxy-phenyl]-5-phenyl-pentan-1-ol (0.62 g, 1.7 mmoles), prepared as described in example 17, in DMSO (10 ml) was added with triethylamine (35 ml) and, after 30 minutes, with pyridinium sulfur trioxide (1.62 g, 10.2 mmoles). After 6 hours, the mixture was diluted with 10 volumes of water and twice extracted with ethyl ether. The organic phases were washed with water, discoloured with charcoal, anhydrified and concentrated. The residue was flash chromatographed (eluent: petrolatum/ethyl acetate 7:3) to give 0.37 g of the title compound (yield: 60%).

$^1$H-NMR (CDCl$_3$) δ: 7.79–6.73(m,8H); 3.96(s,2H); 3.81 (s,3H); 2.78–2.58(m,4H); 1.82–1.59(m,4H); 1.28(s,6H).

EXAMPLE 19

6-Methoxy-4-(4-phenyl-butyl)-2H-phthalazin-1-one

A solution of 1-[2-(4,4-dimethyl-4,5-dihydro-oxazol-2-yl)-5-methoxy-phenyl]-5-phenyl-pentan-1-one (0.37 g, 1 mmole), prepared as described in example 18, in 5 ml of a mixture of water (0.5 ml), ethanol (5 ml), concentrated H$_2$SO$_4$ (0.4 ml) up to 10 ml with ethanol, was stirred at reflux for 20 hours, then concentrated to small volume, taken up in water, extracted with ethyl ether and the ethereal phase was washed with water, anhydrified and brought to dryness. The resultant oil was dissolved in acetic acid (10 ml) and dropwise added, under N$_2$, with a solution of hydrazine monohydrate (0.45 ml, 3 mmoles) in acetic acid (2 ml). The mixture was stirred for 3 hours at 80° C., then overnight at room temperature and at 80° C. for further 5 hours, cooled, almost brought to dryness, taken up in water, basified with NaOH, extracted more times with ethyl acetate. The organic phases were washed with water/NaCl, anhydrified and concentrated. The residue was flash chromatographed (eluent: petroleum/ethyl acetate 6:4) to give 0.09 g of the title compound (yield: 29%).

$^1$H-NMR (CDCl$_3$) δ: 10.03(s-broad,1H); 8.40–7.06(m,8H); 3.91(s,3H); 2.93–2.63(m,4H); 1.88–1.71(m,4H).

EXAMPLE 20

1-Chloro-6-methoxy-4-(4-phenyl-butyl)-phthalazine

Operating as described in example 10 starting from 6-methoxy-4-(4-phenyl-butyl)-2H-phthalazin-1-one (0.2 g, 0.65 mmoles), prepared as described in example 19, in dry acetonitrile (10 ml) and POCl$_3$ (0.31 g, 1.95 mmoles), 0.22 g of the title compound were obtained (stoichiometric yield).

$^1$H-NMR (CDCl$_3$) δ: 8.20–7.13(m,8H); 3.93(s,3H); 3.29–3.22(m,2H); 2.72–2.64(m,2H); 1.98–1.72(m,4H).

EXAMPLE 21

1-(3,5-Dichloro-pyridin-4-ylmethyl)-6-methoxy-4-(4-phenyl-butyl)-phthalazine (Compound 6)

Operating substantially as described in example 5 starting from 3,5-dichloro-4-methyl-pyridine (0.23 g, 1.4 mmoles) in dry DMF (10 ml), 55% NaH in oil (0.061 g, 1.4 mmoles) and 1-chloro-6-methoxy-4-(4-phenyl-butyl)-phthalazine (0.23 g, 0.7 mmole), prepared as described in example 20, in DMF (5 ml), 0.082 g of the title compound were obtained in form of amorphous hygroscopic solid (yield: 21%).

$^1$H-NMR (CDCl$_3$) δ: 8.79–7.94(m,3H); 8.72(s,2H); 7.27–7.10(m,5H); 5.70(broad,H$^+$); 5.12(s,2H); 4.09(s,3H); 3.48(t-broad); 2.60(t-broad,2H); 1.88–1.61(m,4H).

EXAMPLE 22

4-(3,5-Dichloro-pyridin-4-ylmethyl)-7-methoxy-1,2-dihydro-phthalazine (Compound 7)

A suspension of 1-(3,5-dichloro-pyridin-4-ylmethyl)-6-methoxy-phthalazine (23.5 g, 73.4 mmoles), prepared as described in example 5, and PtO$_2$ hydrate (0.5 g, 2.2 mmoles) in THF (600 ml) was put in a hydrogenator at room temperature and 2 atmospheres. After 22 hours the mixture was filtered over celite and brought to dryness to give 23.8 g of the title compound (stoichiometric yield). m.p.: 181–183° C.

$^1$H-NMR (CDCl$_3$) δ: 8.45(s,2H); 7.37–6.63(m,3H); 4.20 (s,2H); 4.08(s,2H); 3.83(s,3H).

EXAMPLE 23

1-[4-(3,5-Dichloro-pyridin-4-ylmethyl)-7-methoxy-1H-phthalazin-2-yl]-ethanone (Compound 8)

A. A solution of 1-(3,5-dichloro-pyridin-4-ylmethyl)-6-methoxy-phthalazine (1 g, 3.12 mmoles), prepared as described in example 5, in glacial acetic acid (30 ml) under stirring and N$_2$ was added with 10% Pd/C in catalytic amount, and the solution was put in a hydrogenator at 4 atmospheres. After 2 days the mixture was filtered and brought to dryness. The residue was flash chromatographed (eluent: hexane/ethyl acetate 3:7) to give 0.5 g of the title compound (yield: 50%). m.p.: 186–188° C.

B. As an alternative to the previous synthesis, the title compound was prepared starting from a solution of 4-(3,5-dichloro-pyridin-4-ylmethyl)-7-methoxy-1,2-dihydro-phthalazine (2 g, 6.2 mmoles), prepared as described in example 22, in dry THF (60 ml) under stirring and dry N$_2$ at 0° C. The mixture was added with triethylamine (1.57 g, 15.5 mmoles), then with acetyl chloride (0.44 ml, 6.2 mmoles). After 10 minutes the mixture was brought to room temperature and kept at such temperature for 2.5 hours, then poured into water/ice and extracted more times with CH$_2$Cl$_2$. The organic phases were washed with 5% NaOH and water, anhydrified and brought to dryness to give a solid which, by crystallisation from acetonitrile (70 ml), gave 1.95 g of the title compound having the same physochemical characteristics set forth at point A.

$^1$H-NMR (CDCl$_3$) δ: 8.48(s,2H); 7.46(d,1H,J=8.6 Hz); 6.88(dd,1H); 6.70(d,1H,J=2.4 Hz); 4.85(s,2H); 4.29(s,2H); 3.84(s,3H); 1.84(s,3H).

EXAMPLE 24

4-(3,5-Dichloro-pyridin-4-ylmethyl)-7-methoxy-1H-phthalazine-2-carboxylic acid amide (Compound 9)

A solution of 4-(3,5-dichloro-pyridin-4-ylmethyl)-7-methoxy-1,2-dihydro-phthalazine (0.4 g, 1.24 mmoles), prepared as described in example 22, in glacial acetic acid (8 ml), under stirring and dry $N_2$ at room temperature, was added with potassium cyanate (0.2 g, 2.48 mmoles) and the reaction mixture was left to stand for 20 hours, then poured into 10% NaOH in excess and extracted more times with $CH_2Cl_2$. The organic phases were washed with water, anhydrified and concentrated to give a residue which was flash chromatographed (eluent: hexane/ethyl acetate 3:7) to give 0.36 g of the title compound (yield: 80%). m.p.>230° C.

$^1$H-NMR (CDCl$_3$) δ: 8.50(s,2H); 7.47–6.69(m,3H); 5.01 (broad,2H); 4.82(s,2H); 4.29(s,2H); 3.85(s,3H).

EXAMPLE 25

1-[4-(3,5-Dichloro-pyridin-4-ylmethyl)-7-methoxy-1H-phthalazin-2-yl]-propan-1-one (Compound 10)

A solution of 4-(3,5-dichloro-pyridin-4-ylmethyl)-7-methoxy-1,2-dihydro-phthalazine (1 g, 3.1 mmoles), prepared as described in example 22, in THF (35 ml), under stirring and dry $N_2$ at room temperature, was dropwise added with triethylamine (1.08 ml, 7.76 mmoles), then, at 0° C., with propionyl chloride (0.323 ml, 3.72 mmoles). After 10 minutes the mixture was brought to room temperature and after 3 hours poured into water/ice and THF was evaporated. The mixture was extracted more times with $CH_2Cl_2$ and the organic phases were washed with 5% NaOH and water, anhydrified and brought to dryness to give a solid which was crystallised from acetonitrile (50 ml). 1 g of the title compound was obtained (yield: 86%). m.p.: 195–197° C.

$^1$H-NMR (CDCl$_3$) δ: 8.48(s,2H); 7.48–6.70(m,3H); 4.85 (s,2H); 4.29(s,2H); 3.84(s,3H); 2.15(q,2H); 0.87(t,3H,J=7.5 Hz).

EXAMPLE 26

1-[4-(3,5-Dichloro-pyridin-4-ylmethyl)-7-methoxy-1H-phthalazin-2-yl]-2-methyl-propan-1-one (Compound 11)

Operating substantially as described in example 25 starting from 4-(3,5-dichloro-pyridin-4-ylmethyl)-7-methoxy-1,2-dihydro-phthalazine (1 g, 3.1 mmoles), prepared as described in example 22, in dry THF (35 ml), triethylamine (1.08 ml, 7.76 mmoles) and isobutanoyl chloride (0.39 ml, 3.72 mmoles), 1 g of the title compound was obtained (yield: 83%). m.p.: 210–212° C.

$^1$H-NMR (CDCl$_3$) δ: 8.48(s,2H); 7.46(d,1H,J=8.6 Hz); 6.88(dd,1H); 6.71(d,1H,J=2.6 Hz); 4.83(s,2H); 4.29(s,2H); 3.84(s,3H); 2.80–2.60(m,1H); 0.83(d,6H,J=6.8 Hz).

EXAMPLE 27

[4-(3,5-Dichloro-pyridin-4-ylmethyl)-7-methoxy-1H-phthalazin-2-yl]-phenyl-methanone (Compound 12)

Operating substantially as described in example 25 starting from 4-(3,5-dichloro-pyridin-4-ylmethyl)-7-methoxy-1,2-dihydro-phthalazine (1 g, 3.1 mmoles), prepared as described in example 22, in dry THF (35 ml), triethylamine (1.08 ml, 7.76 mmoles) and benzoyl chloride (0.43 ml, 3.72 mmoles), 1 g of the title compound were obtained (yield: 85%). m.p.: 190–192° C.

$^1$H-NMR (CDCl$_3$) δ: 8.24(s,1H); 7.50–6.77(m,8H); 5.03 (s,2H); 4.22(s,2H); 3.87(s,3H).

EXAMPLE 28

1-[4-(3,5-Dichloro-pyridin-4-ylmethyl)-7-methoxy-1H-phthalazin-2-yl]-2-phenyl-ethanone (Compound 13)

Operating substantially as described in example 25 starting from 4-(3,5-dichloro-pyridin-4-ylmethyl)-7-methoxy-1,2-dihydro-phthalazine (1 g, 3.1 mmoles), prepared as described in example 22, in dry THF (35 ml), triethylamine (1.08 ml, 7.76 mmoles) and phenylacetyl chloride (0.49 ml, 3.72 mmoles), 0.9 g of the title compound were obtained (yield: 66.2%). m.p.: 143–145° C.

$^1$H-NMR (CDCl$_3$) δ: 8.48(s,2H); 7.47(d,1H,J=8.6 Hz); 7.2–6.85(m,6H); 6.71(d,1H,J=2.6 Hz); 4.88(s,2H); 4.31(s, 2H); 3.84(s,3H); 3.58(s,3H)

EXAMPLE 29

4-(3,5-Dichloro-pyridin-4-ylmethyl)-7-methoxy-1H-phthalazin-2-carbaldehyde (Compound 14)

A solution of formic acid (0.123 ml, 3.255 mmoles) in dry THF (40 ml), under stirring and dry $N_2$ at room temperature, was added with 1,1'-carbonyldiimidazole (0.53 g, 3.255 mmoles) and the mixture was left to stand for 1 hour. Then 4-(3,5-dichloro-pyridin-4-ylmethyl)-7-methoxy-1,2-dihydro-phthalazine (1 g, 3.1 mmoles), prepared as described in example 22, was portionwise added. After 6.5 hours another portion of a mixture of formic acid/carbonyldiimidazole (about ⅓ of the previous one) was added and the mixture was stirred at room temperature for 1 hour, then left to stand overnight. The mixture was poured into water/ice, THF was evaporated, and the solution was extracted more times with $CH_2Cl_2$. The organic phase was washed with $KHSO_4$, then with $NaHCO_3$ and with water, anhydrified and concentrated. The residue was crystallised from acetonitrile (40 ml) to give 1 g of the title compound (yield: 92.6%). m.p.: 165–167° C.

$^1$H-NMR (CDCl$_3$) δ: 8.48(s,2H); 8.29(s,1H); 7.47(s,1H, J=8.6 Hz); 6.89 (dd,1H); 6.71(d,1H,J=2.6 Hz); 4.82(s,2H); 4.29(s,2H); 3.85(s,3H).

EXAMPLE 30

4-(3,5-Dichloro-pyridin-4-ylmethyl)-2-methanesulfonyl-7-methoxy-1,2-dihydro-phthalazine (Compound 13)

Operating substantially as described in example 25 starting from 4-(3,5-dichloro-pyridin-4-ylmethyl)-7-methoxy-1,2-dihydro-phthalazine (1 g, 3.1 mmoles), prepared as described in example 22, in dry THF (30 ml), triethylamine (1.08 ml, 7.76 mmoles) and methanesulfonyl chloride (0.29 ml, 3.72 mmoles), 0.9 g of the title compound were obtained (yield: 75.6%). m.p.: 171–173° C.

$^1$H-NMR (CDCl$_3$) δ: 8.48(s,2H); 7.48–6.73(m,3H); 4.45 and 4.31(2s,4H); 3.85(s,3H); 2.75(s,3H).

EXAMPLE 31

4-(3,5-Dichloro-pyridin-4-ylmethyl)-7-methoxy-1H-phthalazine-2-carboxylic acid methyl ester (Compound 16)

A solution of 4-(3,5-dichloro-pyridin-4-ylmethyl)-7-methoxy-1,2-dihydro-phthalazine (1 g, 3.1 mmoles), prepared as described in example 22, in THF (35 ml), under stirring and dry $N_2$ at room temperature, was added with 1,1'-carbonyldiimidazole (0.55 ml, 3.41 mmoles). The mixture was refluxed for 1 hour. Dry $CH_3OH$ (2 ml) was added and the heating went on for further 2.5 hours. The mixture was cooled, poured into water/ice and extracted with $CH_2Cl_2$. The organic phases were washed with $KHSO_4$, then with 5% NaOH, at last with water, anhydrified and concentrated to give a solid which was put in $CH_3OH$ with a catalytic amount of $NaOCH_3$. The solution was refluxed for 1.5 hours, cooled, $CH_3OH$ was evaporated, the residue was taken up in water and $CH_2Cl_2$. The organic phases were washed with NaOH and water, anhydrified and concentrated to give a solid, which was triturated in $CH_3OH$. 0.6 g of the title compound were obtained (yield: 52%). m.p.: 184–186° C.

$^1$H-NMR ($CDCl_3$) δ: 8.46(s,2H); 7.36(d,1H,J=8.6 Hz); 6.83(dd,1H); 6.69(d,1H,J=2.6 Hz); 4.77(s,2H); 4.32(s,2H); 3.82(s,3H); 3.70(s,3H).

EXAMPLE 32

4-(3,5-Dichloro-pyridin-4-ylmethyl)-7-methoxy-1H-phthalazine-2-carboxylic acid methyl-amide (Compound 17)

Operating substantially as described in example 31 starting from 4-(3,5-dichloro-pyridin-4-ylmethyl)-7-methoxy-1,2-dihydro-phthalazine (1 g, 3.1 mmoles), prepared as described in example 22, in dry THF (35 ml), 1,1'-carbonyldiimidazole (0.55 g, 3.41 mmoles) and 8.03M methylamine in ethanol (2 ml), 1 g of the title compound was obtained (yield: 86%). m.p.: 203–205° C.

$^1$H-NMR ($CDCl_3$) δ: 8.50(s,2H); 7.41(d,1H,J=8.6 Hz); 6.86(dd,1H); 6.7(d,1H,J=2.6 Hz); 5.63–5.55(m,1H); 4.80(s, 2H); 4.27(s,2H); 3.84(s,3H); 2.69(d,3H,J=5 Hz).

EXAMPLE 33

4-(3,5-Dichloro-pyridin-4-ylmethyl)-7-methoxy-1H-phthalazine-2-carboxylic acid dimethyl-amide (Compound 18)

A solution of 4-(3,5-dichloro-pyridin-4-ylmethyl)-7-methoxy-1,2-dihydro-phthalazine (1 g, 3.1 mmoles), prepared as described in example 22, in dry THF (35 ml), under stirring and dry $N_2$ at room temperature, was added with 1,1'-carbonyldiimidazole (0.6 g, 3.72 mmoles), then the mixture was refluxed for 3 hours, cooled, added with 5.6M dimethylamine in ethanol (5 ml) and refluxed again. After 44 hours the mixture was cooled, poured into water/ice and extracted more times with $CH_2Cl_2$. The organic phases were washed with 5% NaOH, then with water, anhydrified and concentrated. The residue was flash chromatographed (eluent: hexane/ethyl acetate 1:1), then crystallised from acetonitrile (30 ml) to give 0.44 g of the title compound (yield: 36.4%). m.p.: 160–162° C.

$^1$H-NMR ($CDCl_3$) δ: 8.45(s,2H); 7.43(d,1H,J=8.5 Hz); 6.88(dd,1H); 6.71(d,1H,J=2.6 Hz); 4.49(s,2H); 4.27(s,2H); 3.84(s,3H); 2.64(s,6H).

EXAMPLE 34

6-Methoxy-3H-isobenzofuran-1-one

Concentrated HCl (1 l) was added with 40% w/v formaldehyde (65 ml, 0.86 mole) under vigorous stirring, then with 3-methoxybenzoic acid (100 g, 0.66 mole) and the mixture was heated to 100° C. controlling the, generation of gas, for 30 minutes. The cooling of the mixture yielded a precipitate which was filtered and stored, while the mixture was washed with water, then with 5% NaOH. The new precipitate was twice extracted with $CH_2Cl_2$, the extract anhydrified, concentrated, joined to the previously filtered solid and both were dissolved in $CH_2Cl_2$ and treated with diethylamine (120 ml, 1.15 moles). After 24 hours it was extracted with 10% HCl and the phases were separated and extracted with $CH_2Cl_2$. The organic phase was washed with 10% NaOH, discoloured with charcoal, anhydrified and concentrated. The residue was dissolved in $CH_2Cl_2$ and treated, under stirring, with 10% HCl for 30 minutes. The organic phase was washed with water, anhydrified and dried. The residue was dissolved in $CH_2Cl_2$ and treated with 10% NaOH under stirring for 30 minutes. The organic phase was washed with water, anhydrified and concentrated to give a solid which was crystallised from $CH_3OH/H_2O$ 65:35 and dried at 50° C. over $P_2O_5$, then crystallised again from $CH_3OH/H_2O$ 6:4 to give 35.28 g of the title compound (yield: 32%). m.p.: 115–117° C.

$^1$H-NMR ($CDCl_3$) δ: 7.37–7.20(m,3H); 5.21(s); 3.85(s, 3H).

EXAMPLE 35

3-Bromo-6-methoxy-3H-isobenzofuran-1-one

6-Methoxy-3H-isobenzofuran-1-one (35.28 g, 0.215 mole), prepared as described in example 34, suspended in $CCl_4$ (350 ml) under $N_2$ was added with N-bromosuccinimide (40 g, 0.225 mole) and benzyl peroxide in catalytic amount, then slowly brought to reflux. After 2.5 hours the heating was stopped and the mixture was left to stand overnight at room temperature. Further catalyst was added and the mixture was heated for further 3.5 hours. The mixture was cooled in ice, filtered over celite washing well with $CCl_4$ and dried to give 41 g of the title compound (yield: 78%).

$^1$H-NMR ($CDCl_3$) δ: 7.50–7.25(m,4H); 3.87(s,3H).

EXAMPLE 36

(5-Methoxy-3-oxo-1,3-dihydro-isobenzofuran-1-yl)-triphenyl-phosphonium bromide

3-Bromo-6-methoxy-3H-isobenzofuran-1-one (41 g, 0.169 mole), prepared as described in example 35, suspended in dry acetonitrile (205 ml) under $N_2$ was added with triphenylphosphine (42 g, 0.16 mole). The mixture was refluxed and after about 3 hours cooled and concentrated to give a solid, which was treated with ethyl ether, filtered and brought to dryness under vacuum. There were thus obtained 74 g of the title compound (yield: 84%).

$^1$H-NMR ($CDCl_3$) δ: 9.63(s,1H); 7.84–7.75(m,15H); 7.09–6.91(m,3H); 3.77(s,3H).

EXAMPLE 37

3-(3,5-Dichloro-pyridin-4-ylmethylene)-6-methoxy-3H-isobenzofuran-1-one

A suspension under $N_2$ of (5-methoxy-3-oxo-1,3-dihydro-isobenzofuran-1-yl)triphenyl-phosphonium bromide (74 g, 0.134 mole), prepared as described in example 36, and 3,5-dichloro-pyridin-4-carbaldehyde (23.6 g, 0.134 mole) in $CH_2Cl_2$ (500 ml) was dropwise added with triethylamine (18.5 ml, 0.134 mole), adjusting the temperature with a water bath. The mixture was stirred overnight, then cooled and treated with 5% HCl. The phases were separated and the acidic one was extracted with CH₂Cl₂, washed with H₂O/NaCl, discoloured with charcoal, anhydrified and concentrated at high vacuum. There were obtained 85.4 g of a crude which was used as such in the subsequent step. A sample of the crude was purified by flash chromatography (eluent: hexane/ethyl acetate 1:1).

¹H-NMR (CDCl₃) δ: 8.60(s,2H); 7.77–6.68(m,4H); 3.80 (s,3H).

EXAMPLE 38

4-(3,5-Dichloro-pyridin-4-ylmethyl)-7-methoxy-2H-phthalazin-1-one (Compound 19)

A suspension of 3-(3,5-dichloro-pyridin-4-ylmethylene)-6-methoxy-3H-isobenzofuran-1-one (84.4 g, 0.126 mole), prepared as described in example 37, in CH₃OH (200 ml) under N₂ was added with hydrazine monohydrate (18.4 ml, 0.378 mole). The mixture was refluxed for 1 hour, then left overnight at room temperature and cooled over ice. The solid was filtered, washed with cold CH₃OH and dried in oven at 50° C. under vacuum; 33.3 g of the title compound were thus obtained (yield: 80%). m.p.: 259–262° C.

¹H-NMR (CDCl₃) δ: 12.34(s,1H); 8.64(s,2H); 8.19–7.54 (m,3H); 4.58(s,2H); 3.95(s,3H).

EXAMPLE 39

4-(3,5-Dichloro-pyridin-4-ylmethyl)-2-ethyl-7-methoxy-2H-phthalazin-1-one (Compound 20)

A suspension of 4-(3,5-dichloro-pyridin-4-ylmethyl)-7-methoxy-2H-phthalazin-1-one (0.52 g, 1.55 mmoles), prepared as described in example 38, in DMF (10 ml) was added with NaH (0.057 g, 1.55 mmoles) and, after 1 hour, with ethyl iodide (0.125 ml, 1.55 mmoles). After 1 night the mixture was diluted with water (10 volumes) and extracted twice with ethyl acetate. The organic phase was anhydrified and concentrated to give a solid which was purified by flash chromatography (eluent: ethyl acetate/petrolatum 3:7). There was thus obtained 0.44 g of the title compound (yield: 78%). m.p.: 150.2–151.2° C.

¹H-NMR (CDCl₃) δ: 8.50(s,2H); 7.86–7.36(m,3H); 4.51 (s,2H); 4.01(q,2H,J=7.02 Hz); 3.96(s,3H); 1.13(t,3H).

EXAMPLE 40

2-Benzyl-4-(3,5-dichloro-pyridin-4-ylmethyl)-7-methoxy-2H-phthalazin-1-one (Compound 21)

Operating substantially as described in example 39 starting from 4-(3,5-dichloro-pyridin-4-ylmethyl)-7-methoxy-2H-phthalazin-1-one (1 g, 2.55 mmoles), prepared as described in example 38, in DMF (10 ml), NaH (0.1 g, 2.55 mmoles) and benzyl chloride (0.32 ml, 2.8 mmoles), 0.6 g of the title compound were obtained (yield: 55%). m.p.: 134–135° C.

¹H-NMR (CDCl₃) δ: 8.50(s,2H); 7.85–7.35(m,3H); 7.22–7.12(m,5H); 5.10(s,2H); 4.50(s,2H); 3.95(s,3H).

EXAMPLE 41

4-(3,5-Dichloro-pyridin-4-ylmethyl)-7-methoxy-2-phenethyl-2H-phthalazin-1-one (Compound 22)

Operating substantially as described in example 39 starting from 4-(3,5-dichloro-pyridin-4-ylmethyl)-7-methoxy-2H-phthalazin-1-one (1 g, 2.55 mmoles), prepared as described in example 38, in DMF (10 ml), NaH (0.1 g, 2.55 mmoles) and (2-chloroethyl)benzene (0.36 ml, 2.8 mmoles), 0.7 g of the title compound were obtained (yield: 62%). m.p.: 147.5–148.5° C.

¹H-NMR (CDCl₃) δ: 8.52(s,2H); 7.84–7.37(m,3H); 7.21–7.06(m,5H); 4.51(s,2H); 4.26–4.19(m,2H); 3.96(s, 3H); 2.92–2.84(m,2H).

EXAMPLE 42

4-(3,5-Dichloro-pyridin-4-ylmethyl)-7-methoxy-2-(5-phenyl-pentyl)-2H-phthalazin-1-one (Compound 23)

Operating substantially as described in example 39 starting from 4-(3,5-dichloro-pyridin-4-ylmethyl)-7-methoxy-2H-phthalazin-1-one (1.34 g, 3.4 mmoles), prepared as described in example 38, in DMF (25 ml), NaH (0.13 g, 3.4 mmoles) and (5-phenyl-pentyl-1-yl) 4-methyl-phenylsulfonate (1.34 ml, 4.2 mmoles), 1.1 g of the title compound were obtained (yield: 24%). m.p.: 107.9–109.9° C.

¹H-NMR (CDCl₃) δ: 8.49(s,2H); 7.86–7.37(m,3H); 7.27–7.07(mm,5H); 4.51(s,2H); 4.01–394(m,2H); 3.97(s, 3H); 2.55–217(m,2H); 1.68–1.12(m,6H)

EXAMPLE 43

4-(3,5-Dichloro-pyridin-4-methyl)-2-methanesulfonyl-7-methoxy-2H-phthalazin-1-one (Compound 24)

Operating substantially as described in example 39 starting from 4-(3,5-dichloro-pyridin-4-ylmethyl)-7-methoxy-2H-phthalazin-1-one (0.5 g, 1.27 mmoles), prepared as described in example 38, in DMF (10 ml), NaH (0.05 g, 1.27 mmoles) and mesyl chloride (0.1 ml, 1.27 mmoles), 0.18 g of the title compound were obtained (yield: 35%). m.p.: 192.6–193.6° C.

¹H-NMR (CDCl₃) δ: 8.52(s,2H); 7.86(d,1H,J=2.5 Hz); 7.845(d,1H,J=8.7 Hz); 7.48(dd,1H); 4.55(s,2H); 3.98(s,3H); 3.32(s,3H).

EXAMPLE 44

[4-(3,5-Dichloro-pyridin-4-ylmethyl)-7-methoxy-1-oxo-1H-phthalazin-2-yl]-acetic acid ethyl ester (Compound 25)

Operating substantially as described in example 39 starting from 4-(3,5-dichloro-pyridin-4-ylmethyl)-7-methoxy-2H-phthalazin-1-one (2 g, 5.1 mmoles), prepared as described in example 38, in DMF (20 ml), NaH (0.2 g, 5.1 mmoles) and ethyl bromoacetate (0.62 ml, 5.61 mmoles), a crude was obtained and crystallised from isopropyl ether/acetonitrile 85:15 (40 ml) yielding 1.12 g of the title compound (yield: 52%). m.p.: 141–142° C.

¹H-NMR (CDCl₃) δ: 8.48(s,2H); 7.85–7.39(m,3H); 4.688 (s,2H); 4.52(s,2H); 4.14(q,2H); 3.96(s,3H); 1.20(t,3H,J=7.1 Hz).

EXAMPLE 45

4-Chloro-1-(3,5-dichloro-pyridin-4-ylmethyl)-6-methoxy-phthalazine

A suspension of 4-(3,5-dichloro-pyridin-4-ylmethyl)-7-methoxy-2H-phthalazin-1-one (10 g, 25.5 mmoles), prepared as described in example 38, in acetonitrile (300 ml), was added with POCl₃ (22.2 ml, 230 mmoles) and the mixture was refluxed. After 3 hours, the solution was concentrated, taken up in $CH_2Cl_2$, in water, and the pH was brought to 7–8 by $Na_2CO_3$. The organic phases were discoloured with charcoal, anhydrified and concentrated to give 10 g of the title compound (stoichiometric yield). m.p.: 156–166° C.

$^1$H-NMR (CDCl$_3$) δ: 8.50(s,2H); 8.13–7.54(m,3H); 4.88 (s,2H); 4.04(s,3H).

EXAMPLE 46

4-Bromo-1-(3,5-dichloro-pyridin-4-ylmethyl)-6-methoxy-phthalazine

A suspension of 4-(3,5-dichloro-pyridin-4-ylmethyl)-7-methoxy-2H-phthalazin-1-one (10 g, 25.5 mmoles), prepared as described in example 38, in acetonitrile (300 ml), was added with POBr$_3$ (22 g, 76.5 mmoles) and the mixture was refluxed. After 1 night under reflux and another to stand, the solution was concentrated, taken up in water, cooled in ice and alkalinised with concentrated NaOH. There was extracted three times with $CH_2Cl_2$ and the organic phases were discoloured with charcoal, anhydrified and concentrated. The crude was purified by flash chromatography (eluent: petrolatum/ethyl acetate 8:2, then 6:4) to give 8.4 g of the title compound (yield: 82%).

$^1$H-NMR (CDCl$_3$) δ: 8.49(s,2H); 8.12–7.50(m,3H); 4.83 (s,2H); 4.04(s,3H).

EXAMPLE 47

1-(3,5-Dichloro-pyridin-4-ylmethyl)-6-methoxy-4-phenyl-phthalazine (Compound 5)

ZnCl$_2$ (2.04 g, 15 mmoles) under N$_2$ in THF (100 ml) was added with phenyl lithium (7.5 ml, 15 mmoles; 2M in cyclohexane/ethyl ether 7:3) at 0–4° C. The mixture was stirred at room temperature for 1 hour. 4-Bromo-(3,5-dichloro-pyridin-4-ylmethyl)-6-methoxy-phthalazine (3 g, 7.5 mmoles), prepared as described in example 46, palladium acetate (0.034 g, 0.15 mmole) and triphenylphosphine (0.08 g, 0.3 mmole) were added and the mixture was refluxed for 24 hours, cooled and extracted with a saturated solution of NHCl. The organic phase was extracted again with ethyl acetate, discoloured with charcoal, anhydrified and concentrated to give a solid which was flash chromatographed (eluent: petrolatum/ethyl acetate 6:4). The resultant solid was triturated in ethyl ether, crystallised from acetonitrile (80 ml) and dried overnight to give 1.44 g of the title compound (yield: 55%).

The analytical data obtained with this compound concur with the ones of the same compound obtained following the procedure described in example 15.

EXAMPLE 48

1-(3,5-Dichloro-pyridin-4-ylmethyl)-6-methoxy-4-thiazol-2-yl-phthalazine (Compound 26)

A suspension of zinc (0.18 g, 2.76 mmoles) in THF/toluene 2:1 (15 ml), under stirring and N$_2$ under reflux, was added with 2-bromothiazole (0.23 ml, 2.5 mmoles). After 2½ hours 4-bromo-1-(3,5-dichloro-pyridin-4-ylmethyl)-6-methoxy-phthalazine (0.5 g, 1.25 mmoles), prepared as described in example 46, palladium acetate (14 mg, 0.0625 mmole) and triphenylphosphine (32 mg, 0.125 mmole) were added to the cold mixture. The mixture was refluxed for further 30 minutes. After 21 hours the same amounts of palladium acetate and triphenylphosphine were added. After 3 hours under reflux the mixture was cooled and poured into water/ice and NH$_4$Cl, then extracted first with ethyl acetate, then with $CH_2Cl_2$. The organic phase was washed with water, anhydrified and concentrated to give a solid which was flash chromatographed (eluent: hexane/ethyl acetate 7:8) to give 0.26 g of the title compound (yield: 51%). m.p.: 225–230° C.

$^1$H-NMR (CDCl$_3$) δ: 9.34(d,1H,J=2.6 Hz); 8.51(s,2H); 8.19–7.56(m,3H); 7.49(d,1H); 4.93(s,2H); 4.07(s,3H).

EXAMPLE 49

1-(3,5-Dichloro-pyridin-4-ylmethyl)-6-methoxy-4-phenylethynyl-phthalazine (Compound 27)

A solution of 4-chloro-1-(3,5-dichloro-pyridin-4-ylmethyl)-6-methoxy-phthalazine (0.52 g, 1.5 mmoles), prepared as described in example 45, in dry DMF (10 ml) under N$_2$ was added with piperidine (1 ml, 10 mmoles), phenylacetylene (0.15 g, 1.5 mmoles), PdCl$_2$ (0.013 g, 0.075 mmole), triphenylphosphine (0.039 g, 0.15 mmole) and CuI (0.014 g, 0.075 mmole). The mixture was stirred for 20 hours, poured into saturated NHCl (10 volumes) and extracted twice with $CH_2Cl_2$, then washed with 5% HCl, anhydrified and concentrated to give a solid which was flash chromatographed (eluent: $CH_2Cl_2$/ethyl ether 9:1). The resultant solid was triturated in ethyl ether to give 0.41 g of the title compound (yield: 52%). m.p.: 213.4–214.4° C. (dec.).

$^1$H-NMR (CDCl$_3$) δ: 8.51(s,2H); 8.15–7.37(m,8H); 4.91 (s,2H); 4.05(s,3H).

EXAMPLE 50

1-[4-(3,5-Dichloro-pyridin-ylmethyl)-7-methoxy-1H-phthalazin-1-yl]-pyrrolidin-2-one (Compound 28)

A solution of 2-pyrrolidinone (0.14 ml, 1.83 mmoles) in dry DMF (10 ml) under N$_2$ was added with NaH (0.068 g, 1.7 mmoles; 60% in oil) and the mixture was heated to 40° C. for 1 hour, cooled and added with 4-chloro-1-(3,5-dichloro-pyridin-4-ylmethyl)-6-methoxy-phthalazine (0.5 g, 1.41 mmoles), prepared as described in example 45. The mixture was heated to 80° C. overnight, then poured into water (10 volumes) and extracted three times with ethyl acetate. The organic phase was discoloured with charcoal, anhydrified and concentrated to give a solid which was flash chromatographed (eluent: ethyl acetate/petrolatum 9:1). The resultant solid was triturated in ethyl ether and 0.306 g of the title compound were yielded (yield: 53%). m.p.: 223–225° C.

$^1$H-NMR (CDCl$_3$) δ: 8.50(s,2H); 8.14–7.23(m,3H); 4.87 (s,2H); 4.22(t,2H,J=6.9 Hz); 3.97(s,3H); 2.69(t,2H,J=7.9 Hz); 2.37–2.22(m,2H).

EXAMPLE 51

1-(3,5-Dichloro-pyridin-4-ylmethyl)-6-methoxy-4-[1,2,4]triazol-1-yl-phthalazine (Compound 29)

Operating substantially as described in example 50 starting from 1,2,4-triazole (0.19 g, 2.8 mmoles) in dry DMF (10 ml), NaH (0.084 g, 2.1 mmoles; 60% in oil) and 4-chloro-1-(3,5-dichloro-pyridin-4-ylmethyl)-6-methoxy-phthalazine (0.5 g, 1.4 mmoles), prepared as described in example 45, 0.42 g of the title compound were obtained (yield: 77%). m.p.: 207–208° C.

$^1$H-NMR (CDCl$_3$) δ: 9.21(s,1H); 8.53(s,2H); 8.46(d,1H, J=2.6 Hz); 8.25(s,1H); 8.22(d,1H,J=9.1 Hz); 7.66(dd,1H); 4.94(s,2H); 4.02(s,3H).

EXAMPLE 52

3-Benzyloxy-4-methoxy-benzaldehyde

A mixture of 3-hydroxy-4-methoxy-benzaldehyde (100 g, 0.657 mole), ethanol (300 ml), $K_2CO_3$ (108.9 g, 0.788 mole), benzyl chloride (86.8 ml, 0.755 mole) and NaI (5 g) under $N_2$ was refluxed under stirring for 2.5 hours, then cooled and added with water (900 ml). The precipitate was filtered, washed with water, and then with petrolatum, then dried under vacuum at 40° C. to give 159 g of the title compound which was used as such in the subsequent step.

EXAMPLE 53

3-Benzyloxy-4-methoxy-benzoic acid

A solution of $KMnO_4$ (24.81 g, 0.157 mole) in water (100 ml) was added under stirring with a solution of tetrabutylammonium bromide (50.61 g, 0.157 mole) in water (200 ml), diluting with further water (200 ml). The solid was separated by filtration, squeezed and dissolved in pyridine (300 ml). The solution was dropped into a solution of 3-benzyloxy-4-methoxy-benzaldehyde (38.2 g, 0.157 mole), prepared as described in example 52, in pyridine (150 ml) in water bath. After 3 hours the mixture was brought to acidic pH with 1N HCl, the solid was filtered off and the mother liquors were extracted more times with $CH_2Cl_2$. The organic phase was anhydrified, concentrated and the residue taken up in 1N NaOH and washed with ethyl ether. The aqueous solution was acidified and extracted twice with $CH_2Cl_2$, brought to dryness, discoloured with TONSIL® and concentrated to small volume. The precipitate was filtered to give 35.869 g of the title compound (yield: 88%).

$^1$H-NMR (CDCl$_3$) δ: 7.78–6.69(m,8H); 5.18(s,2H); 3.39 (s,3H).

EXAMPLE 54

3-Benzyloxy-4-methoxy-benzoyl chloride

A solution of 3-benzyloxy-4-methoxy-benzoic acid (35.86 g, 0.139 mole), prepared as described in example 53, in thionyl chloride (150 ml) was refluxed for 2 hours under $N_2$, evaporated to dryness and taken up twice in toluene (100 ml) to give 35.01 g of the title compound (yield: 98%).

$^1$H-NMR (CDCl$_3$) δ: 7.84–6.90(m,8H); 5.16(s,2H); 3.95 (s,3H).

EXAMPLE 55

3-Benzyloxy-N,N-diethyl-4-methoxy-benzamide

A solution of 3-benzyloxy-4-methoxy-benzoyl chloride (35.01 g, 0.127 mole), prepared as described in example 54, in $CH_2Cl_2$ (200 ml) was dropwise added at 5–10° C. with diethylamine (131 ml, 92.54 g, 1.27 mole) in $CH_2Cl_2$ (130 ml). The mixture was evaporated to dryness, dissolved in ethyl acetate, washed with water, 2% $KHSO_4$, water again and $NaHCO_3$, anhydrified over $Na_2SO_4$ and brought to dryness. The residue was taken up in petrolatum (250 ml) to give 37.65 g of the title compound (yield: 95%)

$^1$H-NMR (CDCl$_3$) δ: 7.43–6.84(m,8H); 5.14(s,2H); 3.88 (s,3H); 3.31(m,4H); 1.07(m,6H).

EXAMPLE 56

3-Benzyloxy-N,N-diethyl-2-formyl-4-methoxy-benzamide

A solution of 3-benzyloxy-N,N-diethyl-4-methoxy-benzamide (39.54 g, 126.2 mmoles), prepared as described in example 55, and tetramethylethylendiamine (16.13 g, 138.8 mmoles) in THF (4,250 ml), cooled to –78° C. under $N_2$, was dropwise added with 1.21M sec-butyl lithium (115.64 ml, 138.8 mmoles). After 2 hours DMF (43 ml, 555 mmoles) was added and the mixture was left at –78° C. for 4 hours, then overnight let the temperature rise. The mixture was washed with a 0.4M pH=7 phosphate buffer, the organic phase was separated and the aqueous one was extracted with ethyl ether. The organic phase was anhydrified and dried to give a solid which was filtered off. The mother liquors were brought to dryness and the crude flash chromatographed (eluent: ethyl acetate/petrolatum 1:1) to give 13.76 g of the title compound (yield: 32%).

$^1$H-NMR (CDCl3) δ: 10.22(s,1H); 7.36–7.29(m,5H); 7.13 and 6.94(2s,2H,J=8.3 Hz); 5.17(s,2H); 3.94(s,3H); 3.52 and 2.93(2q,4H); 1.26 and 0.93(2t,H).

EXAMPLE 57

3,4-Dihydroxy-5-methoxy-3H-isobenzofuran-1-one

A solution of 3-benzyloxy-N,N-diethyl-2-formyl-4-methoxy-benzamide (11.6 g, 34 mmoles), prepared as described in example 56, in 10% HCl (80 ml) and acetic acid (80 ml) was refluxed for 18 hours. The solvents were evaporated and the crude taken up in toluene. The solid was washed with ethyl ether and brought to dryness to give 6.66 g of the title compound (quantitative yield) which was used as such in the subsequent step.

$^1$H-NMR (CDCl$_3$) δ: 9.64 and 7.82(2s broad,2H); 7.28–7.16(m,2H); 3.89(s,3H); 6.53(s broad,1H).

EXAMPLE 58

5-Hydroxy-6-methoxy-2H-phthalazin-1-one

A solution of 3,4-dihydroxy-5-methoxy-3H-isobenzofuran-1-one (6.63 g, 34 mmoles), prepared as described in example 57, in ethanol (60 ml) was added with 98% hydrazine (8.5 ml). The mixture was heated to clarity and after 5 minutes a precipitate formed and was filtered and treated with 1N HCl. The mother liquors were concentrated more times and the resultant solid fractions joined to give 4.65 g of the title compound (yield: 72%).

$^1$H-NMR (CDCl$_3$) δ: 12.33(m,1H); 10.06(s,1H); 8.36(s, 1H); 7.68 and 7.49(2d,2H,J=8.6 Hz); 3.94(s,3H).

EXAMPLE 59

Trifluoro-methanesulfonic acid 6-methoxy-1-oxo-1,2-dihydro-phthalazin-5-yl ester A suspension of 5-hydroxy-6-methoxy-2H-phthalazin-1-one (4.9 g, 25.5 mmoles), prepared as described in example 58, in $CH_2Cl_2$ (100 ml) and pyridine (10.27 ml, 127.5 mmoles) under $N_2$ was dropwise added, at –5÷0° C., with triflic anhydride (4.72 ml, 28.05 mmoles). After 30 minutes at –5° C., further triflic anhydride (0.94 ml) was added and after 30 minutes the mixture was diluted with $CH_2Cl_2$ (500 ml), washed with 5% citric acid (200 ml) and water, anhydrified over $Na_2SO_4$ and evaporated to small volume. The crystallised product was filtered and washed with $CH_2Cl_2$ to give 4.14 g of the title compound. The mother liquors were brought to dryness and flash chromatographed (eluent: petrolatum/ethyl acetate 1:1). The resultant solid was taken up in petrolatum and filtered to give 1.9 g of the title compound which joined to the previous gave a total of 6.04 g (yield: 73%).

$^1$H-NMR (CDCl$_3$) δ: 10.60(s-broad,1H); 8.44(d,1H,J=8 Hz); 8.29(s,1H); 7.49(d,1H); 4.07(s,3H).

EXAMPLE 60

6-Methoxy-5-phenylethynyl-2H-phthalazin-1-one

A mixture under $N_2$ of trifluoro-methanesulfonic acid 6-methoxy-1-oxo-1,2-dihydrophthalazin-5-yl ester (1 g, 3.08 mmoles), prepared as described in example 59, phenylacetylene (0.507 ml, 4.62 mmoles), bis(triphenylphosphine)PdCl$_2$ (108 mg, 0.154 mmole), triethylamine (1.71 ml, 12.32 mmoles) in DMF (20 ml) was heated at 90° C. under stirring for 3 hours, then cooled, poured into water and extracted with CH$_2$Cl$_2$. The extract was washed with water, anhydrified over Na$_2$SO$_4$ and brought to dryness. The residue was taken up in ethyl ether and filtered to give 680 mg of the title compound (yield: 80%).

$^1$H-NMR (DMSO) δ: 12.70(s-broad,1H); 8.53(s,1H); 8.25–7.45(m,7H); 4.03(s,3H).

EXAMPLE 61

1-Chloro-6-methoxy-5-phenylethynyl-phthalazine

A suspension of 6-methoxy-5-phenylethynyl-2H-phthalazin-1-one (0.67 g, 2.42 mmoles), prepared as described in example 60, in POCl$_3$ (20 ml) was heated at 80° C. under stirring up to dissolution. After 30 minutes the solution was brought to dryness and the residue taken up in CH$_2$Cl$_2$ (100 ml), washed to alkalinity with a solution of K$_2$CO$_3$, then with water, then anhydrified over Na$_2$SO$_4$ and evaporated to give 715 mg of the title compound (quantitative yield). The compound was used as such in the subsequent step.

$^1$H-NMR (CDCl$_3$) δ: 10.17(s-broad,1H); 8.51(d,1H,J=10 Hz); 8.07(d,1H); 8.70–7.37(m,6H); 4.25(s,3H).

EXAMPLE 62

1(3,5-Dichloro-pyridin-4-ylmethyl)-6-methoxy-5-phenylethynyl-phthalazine (Compound 30)

A solution under $N_2$ of 3,5-dichloro-4-methyl-pyridine (0.768 g, 4.74 mmoles) in dry DMF (10 ml) was added under stirring at room temperature with 60% NaH (189.6 mg, 4.74 mmoles) and the mixture was stirred for 1 hour, then dropwise added with 1-chloro-6-methoxy-5-phenylethynyl-phthalazine (700 mg, 2.37 mmoles), prepared as described in example 61, in dry DMF (20 ml). After 3 hours the mixture was poured into water, extracted with ethyl acetate, washed with water, anhydrified over Na$_2$SO$_4$ and brought to dryness. The residue was flash chromatographed (eluent: petrolatum/ethyl acetate 3:7). The separated product was taken up in ethyl ether and crystallised from 30 ml of ethyl acetate/CH$_2$Cl$_2$ to give 600 mg of the title compound (yield: 60%). m.p.: 217–219° C.

$^1$H-NMR (CDCl$_3$) δ: 9.88(s,1H); 8.51(s,2H); 8.20–7.38(m,7H); 4.90(s,2H); 4.13(s,3H).

EXAMPLE 63

1-(3,5-Dichloro-pyridin-ylmethyl)-6-methoxy-5-styryl-phthalazine (Compound 31)

A solution of 1-(3,5-dichloropyridin-4-ylmethyl)-6-methoxy-5-phenylethynyl-phthalazine (0.47 g, 1.12 mmoles), prepared as described in example 62, in THF (50 ml) was hydrogenated in Parr in the presence of 10% Pd/C (0.1 g) for 2 hours, then filtered, brought to dryness and flash chromatographed (eluent: petrolatum/ethyl acetate 1:1). The fractions containing the product were concentrated and taken up in 20 ml of ethyl ether/petrolatum 1:1. The crystallised was filtered and dried under vacuum at 40° C. to give 0.37 g of the title compound (yield: 78%). m.p.: 180–182° C.

$^1$H-NMR (CDCl$_3$) δ: 9.37(s,1H); 8.48(s,2H); 8.17(d,1H, J=9.2 Hz); 7.62(d,1H); 7.07–6.65(m,7H); 4.89(s,2H); 3.92(s,3H).

EXAMPLE 64

6-Methoxy-5-(5-phenyl-pent-1-ynyl)-2H-phthalazin-1-one

A mixture under $N_2$ of trifluoro-methanesulfonic acid 6-methoxy-1-oxo-1,2-dihydrophthalazin-5-yl ester (2 g, 6.16 mmoles), prepared as described in example 59, pent-4-ynyl-benzene (1.33 g, 9.24 mmoles), bis(triphenylphosphine)PdCl$_2$ (216 mg, 0.308 mmole) and triethylamine (3.42 ml, 24.64 mmoles) in DMF (40 ml) was heated to 90° C. for 3 hours, then poured into water (200 ml), filtered and the precipitate was washed with water to give 1.28 g of the title compound (yield: 65%).

$^1$H-NMR (DMSO) δ: 12.63(s,1H); 8.41(s,1H); 8.16(d,1H, J=8.8 Hz); 7.6(d,H); 7.34–7.14(m,5H); 3.98(s,3H); 2.82–2.53(m,4H); 1.98–1.83(m)

EXAMPLE 65

1-Chloro-6-methoxy-5-(5-phenyl-pent-1-ynyl)-phthalazine

A suspension of 6-methoxy-5-(5-phenyl-pent-1-ynyl)-2H-phthalazin-1-one (1.26 g, 3.96 mmoles), prepared as described in example 64, and POCl$_3$ (30 ml) was heated at 80° C. under stirring up to dissolution. After 30 minutes the solution was brought to dryness, the residue dissolved in CH$_2$Cl$_2$, washed to alkalinity with a diluted solution of K$_2$CO$_3$, then with water, anhydrified over Na$_2$SO$_4$ and brought to dryness to give 1.33 g of the title compound (quantitative yield). The compound was used as such in the subsequent step.

$^1$H-NMR (CDCl$_3$) δ: 9.77(s,1H); 8.21(d,1H,J=9.2 Hz); 7.59(d,1H); 7.34–7.14(m,5H); 4.08(s,3H); 2.89–2.58(m, 4H); 2.10–1.96(m).

EXAMPLE 66

1-(3,5-Dichloro-pyridin-4-ylmethyl)-6-methoxy-5-(5-phenyl-pent-1-ynyl)-phthalazine (Compound 32)

A solution under $N_2$ of 3,5-dichloro-4-methyl-pyridine (1.28 g, 7.9 mmoles) in dry DMF (15 ml) was added under stirring at room temperature with 60% NaH (316 mg, 7.9 mmoles). The mixture was stirred for 1 hour, then dropwise added with 1-chloro-6-methoxy-5-(5phenyl-pent-1-ynyl)-phthalazine (1.33 g, 3.95 mmoles), prepared as described in example 65, in dry DMF (20 ml). After 3 hours the mixture was poured into water, extracted with ethyl acetate, washed with water, anhydrified over Na$_2$SO$_4$ and brought to dryness. The residue was flash chromatographed (eluent: petrolatum/ethyl acetate 1:1). The separated product was taken up in ethanol (10 ml) and crystallised. The resultant product was filtered and dried under vacuum at 40° C. to give 940 mg of the title compound (yield: 51%). m.p.: 130–132° C.

$^1$H-NMR (CDCl$_3$) δ: 9.78(s,1H); 8.50(s,2H); 8.12 and 7.60(2d,2H); 7.33–7.14(m,5H); 4.88(s,2H); 4.09(s,3H); 2.89–2.81(m,2H); 2.62(t,2H,J=7.0 Hz); 2.11–1.96(m,2H).

EXAMPLE 67

1-(3,5-Dichloro-pyridin-4-ylmethyl)-6-methoxy-5-(5-phenyl-pent-1-enyl)phthalazine (Compound 33)

A solution of 1-(3,5-dichloro-pyridin-4-ylmethyl)-6-methoxy-5-(5-phenyl-pent-1-ynyl)-phthalazine (280 mg, 0.6 mmole), prepared as described in example 66, in THF (15 ml) was hydrogenated in Parr in the presence of 10% Pd/C (50 mg) for 1 hour, then filtered, brought to dryness and flash chromatographed (eluent: $CH_2Cl_2/CH_3OH$ 98:2). The separated oil was taken up in ethyl ether (5 ml) and crystallised. The yielded crystallised was filtered and dried under vacuum at 40° C. to give 120 mg of the title compound (yield: 43%). m.p.: 121–123° C.

$^1$H-NMR (CDCl$_3$) δ: 9.42(s,1H); 8.51(s,2H); 8.16 and 7.62(2d,2H,J=9.1 Hz); 7.20–6.97(m,5H); 6.50(d-broad,1H, J=11.4 Hz); 6.14(dt,1H,J=7.1 Hz); 4.90(s,2H); 3.99(s,3H); 2.51–2.43(m,2H); 1.94–1.63(m,4H).

EXAMPLE 68

1-(3,5-Dichloro-pyridin-4-ylmethyl)-6-methoxy-5-(5-phenyl-pentyl)-phthalazine hydrochloride (Compound 34)

A solution of 1-(3,5-dichloro-pyridin-4-ylmethyl)-6-methoxy-5-(5-phenyl-pent-1-ynyl)-phthalazine (770 mg, 1.665 mmoles), prepared as described in example 66, in THE (50 ml). was hydrogenated in Parr in the presence of 10% Pd/C (100 mg) for 24 hours. The catalyst was filtered off and the hydrogenation was kept on for further 24 hours at room temperature and for 5 hours at 80° C. The solution was brought to dryness and flash chromatographed (eluent: petrolatum/ethyl acetate 1:1). The fractions corresponding to the starting compound were brought to dryness and hydrogenated again for 24 hours, then worked up as above. The fractions containing the desired product were joined to the previously obtained ones, dissolved in ethyl acetate and acidified with HCl/ethyl acetate. The precipitate was filtered and crystallised from ethanol (2 ml) and ethyl acetate (8 ml) by subsequent concentration. There were yielded 142 mg of the title compound (yield: 17%). m.p.: 170–173° C.

$^1$H-NMR (CDCl$_3$) δ: 9.83(s,1H); 8.54(s,2H); 8.39 and 7.97(2d,2H,J=9.1 Hz); 7.29–7.11(m,5H); 5.02(s,2H); 4.12(s,3H); 3.16–3.08 and 2.63–2.56(2m,4H); 1.72–1.38(m,6H).

EXAMPLE 69

5-Benzyloxy-6-methoxy-2H-phthalazin-1-one

Glacial acetic acid (285 ml) at 10–20° C. was dropwise added with hydrazine monohydrate (10.16 ml, 209 mmoles) and added with 3-benzyloxy-N,N-diethyl-2-formyl-4-methoxy-benzamide (14.27 g, 41.8 mmoles), prepared as described in example 56. The mixture was left to stand for 2 hours, then evaporated, dissolved in $CH_2Cl_2$, washed with water, anhydrified over $Na_2SO_4$, brought to dryness, and the crude was triturated in petrolatum/ethyl ether 2:1 (150 ml) and filtered to give 11.3 g of the title compound (yield: 96%).

$^1$H-NMR (CDCl$_3$) δ: 10.61(s,1H); 8.30(s,1H); 8.18–7.31 (m,7H); 5.17(s,2H); 4.03(s,3H).

EXAMPLE 70

5-Benzyloxy-1-chloro-6-methoxy-phthalazine

A suspension of 5-benzyloxy-6-methoxy-2H-phthalazin-1-one (4 g, 14.17 mmoles), prepared as described in example 69, in acetonitrile (40 ml), and POCl$_3$ (6.5 ml, 70.8 mmoles) was heated at 80° C. under stirring up to dissolution. After 30 minutes the solution was evaporated and the residue taken up in $CH_2Cl_2$ (100 ml), washed with a cold solution of NaOH (20 ml) and water (200 ml) and extracted in ethyl ether (twice) and ethyl acetate (once) checking the pH to be around 7. The organic phase was washed with a saturated NaCl solution, anhydrified and concentrated to give 4.15 g of the title compound (yield: 97%).

$^1$H-NMR (CDCl$_3$) δ: 9.49(s,1H); 7.95(d,1H,J=9.0 Hz); 7.62(d,1H); 7.41–7.28(m,5H); 5.24(s,2H); 4.86(s,2H); 4.06 (s,3H).

EXAMPLE 71

5-Benzyloxy-1-(3,5-dichloro-pyridin-4-ylmethyl)-6-methoxy-phthalazine

A solution of 3,5-dichloro-4-methyl-pyridine (5.57 g, 34.38 mmoles) in DMF (30 ml) under N$_2$ was added with NaH (60% in oil, 1.38 g, 34.38 mmoles) and the mixture was heated in water-bath at 40° C. After 1 hour a solution of 5-benzyloxy-1-chloro-6-methoxy-phthalazine (4.15 g, 13.75 mmoles), prepared as described in example 70, in DMF (30 ml) was dropped therein and the whole was left at room temperature for 2 hours, then the mixture was poured into salted water and extracted with ethyl acetate. The whole was poured into salted water and pH=7 buffer and extracted three times with ethyl acetate. The resultant solid was filtered, put to dry at the air, dissolved in $CH_2Cl_2$ and concentrated. The organic phase was anhydrified and concentrated to give a solid which triturated in ethyl acetate+ propyl ether gave 3.866 g of product which joined to the previously treated solid amount to a total of 4.346 g of the title compound (yield: 78%).

$^1$H-NMR (CDCl$_3$) δ: 9.60(s,1H); 8.49(s,2H); 7.93(d,1H, J=9.2 Hz); 7.66(d,1H); 7.49–7.31 (m,5H); 5.26(s,2H); 4.86 (s,2H); 4.08(s,3H).

EXAMPLE 72

1-(3,5-Dichloro-pyridin-4-ylmethyl)-6-methoxy-phthalazin-5-ol dihydrochloride

5-Benzyloxy-1-(3,5-dichloro-pyridin-4-ylmethyl)-6-methoxy-phthalazine (4.3 g, 10.08 mmoles), prepared as described in example 71, in glacial acetic acid and 7% HCl was put in a flask under stirring at room temperature for ½ hour, then at 60° C. for 1 hour. The mixture was brought to dryness, taken up more times in toluene to give a solid which was triturated in acetone and dried to give 4.04 g of the title compound (yield: 98%).

$^1$H-NMR (DMSO) δ: 10.14(s,1H); 8.72(s,2H); 8.35–8.25 (m,2H); 5.10(s,2H); 4.12(s,3H).

EXAMPLE 73

Trifluoro-methanesulfonic acid 1-(3,5-dichloro-pyridin-4-ylmethyl)-6-methoxy-phthalazin-5-yl ester A suspension under N$_2$ of 1-(3,5-dichloro-pyridin-4-ylmethyl)-6-methoxy-phthalazin-5-ol (0.469 g, 1.4 mmoles), prepared as described in example 72, in acetonitrile (5 ml) at 40° C. was added with K$_2$CO$_3$ (0.77 g, 5.58 mmoles), a catalytic amount of Na$_2$S$_2$O$_5$ and N,N-bis (trifluoro-methanesulfonyl)phenylamine (1 g, 2.8 mmoles). The suspension turned red and became a solution which was brought to dryness, the residue taken up in $CH_2Cl_2$ and washed with 5% citric acid and water. The solution was anhydrified and concentrated to give a solid which was triturated in ethyl ether to give 1 g of the title compound (yield: 56%).

$^1$H-NMR (CDCl$_3$) δ: 9.52(s,1H); 8.41(s,2H); 8.27(d,1H, J=9.0 Hz); 7.79(d,1H); 5.26(s,2H); 4.87(s,2H); 4.08(s,3H).

EXAMPLE 74

Benzyl-{3-[1-(3,5-dichloro-pyridin-4-ylmethyl)-6-methoxy-phthalazin-5-yl]-prop-2-ynyl}-methyl-amine dihydrochloride (Compound 35)

A suspension under $N_2$ of trifluoro-methanesulfonic acid 1-(3,5-dichloro-pyridin-4-ylmethyl)-6-methoxy-phthalazin-5ester (5 g, 10.68 mmoles), prepared as described in example 73, benzyl-methyl-prop-2-ynyl-amine (2.16 ml, 12.82 mmoles) and diethylamine (100 ml) was added under stirring with bis(triphenylphosphine)$PdCl_2$ (150.2 mg, 0.214 mmole) and CuI (40.75 mg, 0.214 mmole). The mixture was refluxed for 6 hours, brought to dryness and the residue flash chromatographed (eluent: ethyl acetate) to give a solid which was dissolved in $CH_2Cl_2/CH_3OH$ 1:1 (50 ml), acidified with a solution of HCl in ethyl acetate and brought to dryness. The residue was dissolved in $CH_2Cl_2$ (100 ml), brought to dryness again, triturated in ethyl acetate (150 ml), filtered and dried in oven under vacuum at 40° C. to give 5.22 g of the title compound (yield: 83%).

$^1$H-NMR (DMSO) δ: 11.70(s-broad,1H); 9.91(s,1H); 8.72 and 8.13(2d,2H,J=9.3 Hz); 8.69(s,2H); 7.69–7.45(m,5H); 5.05(s,2H); 4.54–4.37(m,4H); 4.15(s,3H); 2.48(s,3H).

EXAMPLE 75

1-(3,5-Dichloro-pyridin-4-ylmethyl)-6-methoxy-5-(5-morpholin-4-yl-pent-1-ynyl)-phthalazine dihydrochloride (Compound 36)

Trifluoro-methanesulfonic acid 1-(3,5-dichloro-pyridin-4-ylmethyl)-6-methoxy-phthalazin-5-yl ester (0.935 g, 2 mmoles), prepared as described in example 73, 4-pent-4-ynyl-morpholine (0.37 g, 2.4 mmoles), diethylamine (9 ml) and dry acetonitrile (6 ml), then bis(triphenylphosphine)$PdCl_2$ (0.014 g, 0.02 mmole) and CuI (0.004 g, 0.02 mmole) were charged in a flask under $N_2$ and the mixture was stirred at room temperature overnight, brought to dryness, the residue taken up in ethyl acetate and washed with water. The organic phase was washed with water, anhydrified and concentrated to give an oil which was flash chromatographed (eluent: $CH_2Cl_2/CH_3OH/NH_3$ 95:5:0.5) to give an oil which was dissolved in ethyl acetate and precipitated by adding HCl in ethyl ether. There was yielded 0.09 g of the title compound. m.p.: 129–131° C. (dec.).

$^1$H-NMR (DMSO) δ: 9.71(s,1H); 8.67(s,2H); 8.59 and 8.02(2d,2H,J=9.2 Hz); 5.00(s,2H); 4.08(s,3H); 4.02–3.63 (m,4H); 3.49–2.70(m,8H); 2.14–1.99(m,2H).

EXAMPLE 76

3-[1-(3,5-Dichloro-pyridin-4-ylmethyl)-6-methoxy-phthalazin-5-yl]-prop-2-yn-1-ol (Compound 37)

Under $N_2$, prop-2-yn-1-ol (0.151 ml, 2.55 mmole), triethylamine (0.95 ml, 6.8 mmoles), trifluoro-methanesulfonic acid 1-(3,5-dichloro-pyridin-4-ylmethyl)-6-methoxy-phthalazin-5-yl ester (0.795 g, 1.7 mmoles), prepared as described in example 73, bis(triphenylphosphine)$PdCl_2$ (0.06 g, 0.08 mmole) and DMF (10 ml) were charged in a flask and heated at 85° C. for 5 hours, then kept at room temperature overnight. The mixture was diluted with ethyl acetate and washed with water. The organic phase was anhydrified and concentrated to give a solid which was triturated in ethyl ether. Adding this product to the one yielded by extraction and chromatography of the mother liquors (eluent: $CH_2Cl_2/CH_3OH/NH_3$ 95:5:0.5), 0.164 g of the title compound were obtained (yield: 26%).

$^1$H-NMR (DMSO) δ: 9.69(s,1H); 8.68(s,2H); 8.57(d,1H, J=9.3 Hz); 7.79(d,1H); 5.50(t,1H); 4.98(s,2H); 4.47(d,2H, J=5.9 Hz); 4.08(s,3H).

EXAMPLE 77

1(3,5-Dichloro-pyridin-4-ylmethyl)-6-methoxy-4-morpholin-4-yl-phthalazine (Compound 38)

A solution under stirring and dry $N_2$ of 4-chloro-(3,5-dichloro-pyridin-4-ylmethyl)-6-methoxy-phthalazine (1 g, 2.82 mmoles), prepared as described in example 45, in DMF (25 ml), at room temperature, was added with morpholine (0.73 g, 8.46 mmoles) and the temperature was raised to 100° C. After 14 hours the whole was brought to dryness and the solid partitioned between water and $CH_2Cl_2$. The organic phase was washed with water, anhydrified and brought to dryness to give a solid which was flash chromatographed (eluent hexane/ethyl acetate 6:4, then in gradient up to 3:7) to give 0.9 g of the title compound (yield: 79%). m.p.: 179–180° C.

$^1$H-NMR (CDCl$_3$) δ: 8.48(s,2H); 8.10–7.34(m,3H); 4.78 (s,2H); 3.98(s,3H); 3.96–3.91(m,4H); 3.41–3.36(m,4H).

EXAMPLE 78

[4-(3,5-Dichloro-pyridin-4-ylmethyl)-7-methoxy-phthalazin-1-yl]-propyl-amine (Compound 39)

4-Chloro-1-(3,5-dichloro-pyridin-4-ylmethyl)-6-methoxy-phthalazine (3.9 g, 11 mmoles), prepared as described in example 45, and n-propylamine (40 ml) were put in autoclave at external 120° C. (internal 100° C., 4 atm) for 2 hours. The solution was concentrated to residue, taken up in $CH_2Cl_2$ and 5% HCl and extracted more times. The aqueous phase was alkalinised with $K_2CO_3$ and extracted with $CH_2Cl_2$. The resultant solid was crystallised from acetonitrile (110 ml), then filtered to give 3.26 g of the title compound (yield: 82%). m.p.: 222–223° C.

$^1$H-NMR (CDCl$_3$) δ: 8.42(s,2H); 7.99(d,1H,J=9.0 Hz); 7.44(dd,1H); 7.03(d,1H,J=2.5 Hz); 4.89(t,1H,J=5.3 Hz); 4.68(s,2H); 3.95(s,3H); 3.63–3.53(m,2H); 1.79–1.60(m, 2H); 0.96(t,3H,J=7.3 Hz).

EXAMPLE 79

4-(3,5-Dichloro-pyridin-4-ylmethyl)-7-methoxy-1H-phthalazine-2-carboxylic acid hydroxyamide (Compound 40)

At room temperature, under stirring and $N_2$, a solution of 4-(3,5-dichloro-pyridin-4-ylmethyl)-7-methoxy-1H-phthalazine (1 g, 3.1 mmoles), prepared as described in example 22, in THF (35 ml), was added with 1,1'-carbonyldiimidazole (0.55 g, 3.41 mmoles) and refluxed, then concentrated and taken up in ethanol. Hydroxylamine hydrochloride (0.26 g, 3.72 mmoles) in ethanol was added. After 10 hours under reflux, the mixture was cooled, concentrated and partitioned between water and $CH_2Cl_2$. The organic phase was washed with water, anhydrified and brought to dryness to give a residue which was flash chromatographed (eluent: $CH_2Cl_2/CH_3OH$ 98:2, then hexane/ethyl acetate 3:7) to give 0.3 g of the title compound (yield: 25%). m.p.: 155–158° C.

$^1$H-NMR (CDCl$_3$) δ: 8.50(s,2H); 7.72(d,1H,J=3.5 Hz); 7.45(d,1H,J=8.7 Hz); 7.22(d,1H); 6.88(dd,1H); 6.69(d,1H, J=2.5 Hz); 4.79(s,2H); 4.27(s,2H); 3.84(s,3H).

EXAMPLE 80

[4-(3,5-Dichloro-pyridin-4-ylmethyl)-7-methoxy-1H-phthalazin-2-yl]oxo-acetic ethyl ester (Compound 41)

At room temperature, under $N_2$ and stirring, a solution of 4-(3,5-dichloro-pyridin-4-ylmethyl)-7-methoxy-1H- phthalazine (2 g, 6.2 mmoles), prepared as described in example 22, in THF (70 ml), was added with triethylamine (2.16 ml, 15.5 mmoles), cooled at 0° C. and dropwise added with ethyl oxalyl chloride (0.83 ml, 7.44 mmoles). After 30 minutes the cooling was stopped and after 5 hours at room temperature the mixture was poured into water/ice, concentrated and extracted more times with $CH_2Cl_2$. The organic phase was washed with water, anhydrified and brought to dryness to give a solid which was crystallised from acetonitrile to give 1.87 g of the title compound (yield: 73%). m.p.: 140–142° C.

$^1$H-NMR (CDCl$_3$) δ: 8.46(s,2H); 7.52–6.70(m,3H); 4.87 (s,2H); 4.28(s,2H); 3.86(s,3H); 3.79(q,2H); 1.15(t,3H,J=7.1 Hz).

EXAMPLE 81

2-Chloro-1-[4-(3,5-dichloro-pyridin-4-ylmethyl)-7-methoxy-1H-phthalazin-2-yl]-ethanone At room temperature, under $N_2$ and stirring, a solution of 1-[4-(3,5-dichloro-pyridin-4-ylmethyl)-7-methoxy-1H-phthalazine (1.9 g, 5.9 mmoles), prepared as described in example 22, in dry THF (70 ml) was added with triethylamine (2.05 ml, 14.7 mmoles) and cooled at 0° C. Chloroacetyl chloride (0.56 ml, 7.07 mmoles) was dropwise added and a precipitate formed. After 1 night further 50% of triethylamine and chloroacetyl chloride was added, and after 20 hours at room temperature the mixture was poured into water/ice, concentrated and extracted more times with $CH_2Cl_2$. The organic phase was washed with water, anhydrified and brought to dryness to give 2.6 g of the title compound (quantitative yield).

EXAMPLE 82

1-[4-(3,5-Dichloro-pyridin-4-ylmethyl)-7-methoxy-1H-phthalazin-2-yl]-2-morpholin-4-yl-ethanone (Compound 42)

A solution under $N_2$ and stirring of 2-chloro-1-[4-(3,5-dichloro-pyridin-4-ylmethyl)-7-methoxy-1H-phthalazin-2-yl]-ethanone (1.3 g, 3.26 mmoles), prepared as described in example 81, in dry CHCl$_3$ (15 ml), at room temperature, was added with morpholine (0.85 g, 9.78 mmoles) and refluxed for 20 hours. The mixture was poured into water/ice, the phases separated and the organic one was washed with water, anhydrified and brought to dryness to give a solid which was crystallised from acetonitrile (45 ml) to give 0.77 g of the title compound (yield: 53%). m.p.: 180–182° C.

$^1$H-NMR (CDCl$_3$) δ: 8.50(s,2H); 7.46(d,1H,J=8.5 Hz); 6.89(dd,1H); 6.71(d,1H,J=2.6 Hz); 4.85(s,2H); 429(s,2H); 3.85(s,3H); 3.70–3.65(m,4H); 3.01(s,2H); 2.39–2.35(m, 4H).

EXAMPLE 83

1-[4-(3,5-Dichloro-pyridin-4-ylmethyl)-7-methoxy-1-phthalazin-2-yl]-2-pyrrolidin-1-yl-ethanone (Compound 43)

A solution under $N_2$ and stirring of 2-chloro-1-[4-(3,5-dichloro-pyridin-4-ylmethyl)-7-methoxy-1H-phthalazin-2-yl]ethanone (1.3 g, 3.26 mmoles), prepared as described in example 81, in dry CHCl$_3$ (15 ml) at room temperature was added with pyrrolidine (0.82 ml, 9.78 mmoles) and refluxed. After 20 hours the mixture was poured into water/ice, the phases separated, and the organic one washed with water, anhydrified and brought to dryness to give a residue which was crystallised from acetonitrile (40 ml) to give 0.79 g of the title compound yield: 58%). m.p.: 148–150° C.

$^1$H-NMR (CDCl$_3$) δ: 8.49(s,2H); 7.45(d,1H,J=8.6 Hz); 6.88(dd,1H,J); 6.70(d,1H,J=2.6 Hz); 4.85(s,2H); 4.28(s,2H); 3.84(s,3H); 3.14(s;2H); 2.48–2.41(m,4H); 1.77–1.68(m, 4H).

EXAMPLE 84

[4-(3,5-Dichloro-pyridin-4-ylmethyl)-7-methoxy-phthalazin-1-yl]-dimethyl-amine (Compound 44)

At room temperature a solution of [4-(3,5-dichloro-pyridin-4-ylmethyl)-7-methoxy-phthalazin-1-yl]-propyl-amine (3.5 g, 5.64 mmoles), prepared as described in example 78, in DMF (35 ml) was stirred under $N_2$, then added with $K_2CO_3$ (0.78 g, 5.64 mmoles) and methyl iodide (0.35 ml, 5.64 mmoles). The mixture was heated at 50° C. and after 20 hours was dried and partitioned between water and $CH_2Cl_2$. The organic phase was washed with water, anhydrified and concentrated to give an oil which was flash chromatographed (eluent: hexane/ethyl acetate 4:6) to give 1 g of the title compound (yield: 50%). m.p.: 170–173° C.

$^1$H-NMR (CDCl$_3$) δ: 8.46(s,2H); 8.05–7.39(m,3H); 4.75 (s,2H); 3.98(s,3H); 3.07(s,6H).

EXAMPLE 85

1-(3,5-Dichloro-pyridin-4-ylmethyl)-4-imidazol-1-yl-6-methoxy-phthalazine (Compound 45)

A solution of imidazole (0.814 g, 11.21 mmoles) in dry DMF (30 ml) was stirred under $N_2$ at room temperature and added with NaH (8.46 mmoles). After 30 minutes 4-chloro-1-(3,5-dichloro-pyridin-4-ylmethyl)-6-methoxy-phthalazine (2 g, 5.64 mmoles), prepared as described in example 45, in dry DMF (30 ml) was added. The mixture was heated at 80° C. for 3.5 hours, cooled, poured into water/ice and extracted three times with $CH_2Cl_2$. The organic phase was washed with water, anhydrified and concentrated to give a solid which was flash chromatographed (eluent: ethyl acetate) yielding 0.9 g of the title compound (yield: 50%). m.p. 250° C.

$^1$H-NMR (CDCl$_3$) δ: 8.53(s,2H); 8.27–7.31(m,6H); 4.94 (s,2H); 3.95(s,3H).

EXAMPLE 86

[4-(3,5-Dichloro-pyridin-4-ylmethyl)-7-methoxy-phthalazin-1-yl]-thiazol-2-yl amine (Compound 46)

At 100° C. a solution of 4-chloro-1-(3,5-dichloro-pyridin-4-ylmethyl)-6-methoxy-phthalazine (0.5 g, 1.41 mmoles), prepared as described in example 45, 2-aminothiazole (0.424 g, 4.23 mmoles), triethylamine (0.59 ml, 4.23 mmoles), palladium acetate (16 mg, 0.07 mmoles) and triphenylphosphine (56 mg, 0.21 mmoles) was stirred under $N_2$. After 20 hours the mixture was poured into water/ice and extracted more times with $CH_2Cl_2$. The organic phase was washed with water, anhydrified and concentrated to give a solid which was flash chromatographed (eluent: hexane/ ethyl acetate 7:3) yielding 0.24 g of the title compound (yield: 50%). m.p.: 218–220° C.

$^1$H-NMR (CDCl$_3$) δ: 14.41(s,1H); 8.51(s,2H); 8.09(d,1H, J=2.7 Hz); 7.81(d,1H,J=8.8 Hz); 7.42–7.36(m,2H); 6.82(d, 1H,J=3.8 Hz); 4.55(s,2H); 4.03(s,3H).

EXAMPLE 87

1-(3,5-Dichloro-pyridin-4-methyl)-6-methoxy-4-phenoxy-phthalazine (Compound 47)

A suspension of DMF (15 ml), phenol (0.53 g, 5.64 mmoles) and NaH (4.23 mmoles) was stirred under dry $N_2$ at room temperature. After 15 minutes 4-chloro-1-(3,5-dichloro-pyridin-4-ylmethyl)-6-methoxy-phthalazine (0.5 g, 1.41 mmoles), prepared as described in example 45, was dropped and the temperature brought to 100° C. After 20 hours the mixture was partitioned between water and $CH_2Cl_2$. The organic phase was washed with water, anhydrified and concentrated to give a residue which was triturated in ethyl ether. The insoluble was flash chromatographed (eluent: hexane/ethyl acetate 7:3) to give a solid which was crystallised from isopropyl ether (15 ml) and yielded 0.25 g of the title compound (yield: 49%). m.p.: 130–132° C.

$^1$H-NMR (CDCl$_3$) δ: 8.43(s,2H); 8.10–7.54(m,3H); 7.43–7.15(m,5H); 4.78(s,2H); 4.03(s,3H).

EXAMPLE 88

1-(3,5-Dichloro-pyridin-4-ylmethyl)-6-methoxy-4-(4-methyl-piperazin-1-yl)-phthalazine (Compound 48)

A solution of 4-chloro-1-(3,5-dichloro-pyridin-4-ylmethyl)-6-methoxy-phthalazine (1 g, 2.82 mmoles), prepared as described in example 45, in DMF (25 ml) was stirred under dry $N_2$ at room temperature, and dropwise added with 1-methylpiperazine (0.848 g, 8.46 mmoles). The mixture was heated at 100° C. for 20 hours, then brought to small volume and partitioned between water and $CH_2Cl_2$. The organic phase was washed with water, anhydrified and concentrated to give a residue which was flash chromatographed (eluent: $CH_2Cl_2/CH_3OH/NH_4OH$ 95:5:0.5). The resultant solid was crystallised from tert-butyl-methyl ether (35 ml) to give 0.4 g of the title compound (yield: 34%). m.p.: 160–162° C.

$^1$H-NMR (CDCl$_3$) δ: 8.47(s,2H); 8.05(d,1H,J=9.1 Hz); 7.42(dd,1H); 7.36(d,1H,J=2.5 Hz); 4.77(s,2H); 3.98(s,3H); 3.49–3.44(m,4H); 2.69–2.63(m,4H); 2.37(s,3H).

EXAMPLE 89

1-(3,5-Dichloropyridin-4-ylmethyl)-6-methoxy-4-pyrrolidin-1-yl-phthalazine (Compound 49)

A solution of 4-chloro-(3,5-dichloro-pyridin-4-ylmethyl)-6-methoxy-phthalazine (1 g, 2.82 mmoles), prepared as described in example 45, in DMF (25 ml) was stirred under dry $N_2$ at room temperature, and dropwise added with pyrrolidine. The mixture was heated at 100° C. for 20 hours, then concentrated and partitioned between water and $CH_2Cl_2$. The organic phase was washed with water, anhydrified and concentrated to give a solid which was crystallised from ethyl acetate (25 ml) to give 0.77 g of the title compound (yield: 71%). m.p.: 170–172° C.

$^1$H-NMR (CDCl$_3$) δ: 8.45(s,2H); 7.98(d,1H,J=9.1 Hz); 7.55(d,1H,J=2.6 Hz); 7.44(dd,1H); 4.69(s,2H); 3.95(s,3H); 3.85–3.78(m,4H); 2.00–1.94(m,4H).

EXAMPLE 90

[4-(3,5-Dichloro-pyridin-4-ylmethyl)-7-methoxy-1-oxo-1H-phthalazin-2-yl]-acetic acid (Compound 50)

A suspension of [4-(3,5-dichloro-pyridin-4-ylmethyl)-7-methoxy-1-oxo-1H-phthalazin-2-yl]-acetic acid ethyl ester (0.65 g, 1.54 mmoles), prepared as described in example 44, in ethanol (30 ml) was added with concentrated NaOH (3 ml). The mixture was stirred overnight at room temperature, then dried, taken up in water and washed twice with $CH_2Cl_2$. The aqueous phase was acidified with concentrated HCl. The precipitate was filtered and dried over $P_2O_5$ at 60° C., then crystallised from $CH_3OH$ (25 ml) and the filtrate was dried at 45° C. to give 0.36 g of the title compound (yield: 60%). m.p.: 221.4–222.4° C.

$^1$H-NMR (CDCl$_3$) δ: 8.63(s,2H); 8.20(d,1H,J=8.8 Hz); 7.68(d,1H,J=2.8 Hz); 7.60(dd,1H); 4.61 and 4.50(2s,4H); 3.96(s,3H).

EXAMPLE 91

2-[4-(3,5-Dichloro-pyridin-4-ylmethyl)-7-methoxy-1-oxo-1H-phthalazin-2-yl]-N-hydroxy-acetamide (Compound 51)

A solution of [4(3,5-dichloro-pyridin-4-ylmethyl)-7-methoxy-1-oxo-1H-phthalazin-2-yl]-acetic acid (0.61 g, 1.55 mmoles), prepared as described in example 90, in dry DMF (25 ml), pH under $N_2$, was added with 1,1'-carbonyldiimidazole (0.38 g, 2.32 mmoles). The mixture was stirred at room temperature for 4 hours then cooled, added with hydroxylamine hydrochloride (0.18 g, 2.55 mmoles) and stirred overnight. A precipitate formed and the solution was dried under vacuum, then taken up in 10% NaOH. The stirring was kept on for 2 hours, then the solid was filtered, washed with water, then with acetone and ethyl ether. It was taken up in 5% HCl and stirred for 1 hour, then filtered and washed with water, acetone and ethyl ether. The solid was dried under vacuum at 50° C., crystallised from acetic acid (60 ml) and dried under vacuum at 40° C. to give 0.3 g of the title compound (yield: 40%).

m.p.: 256.4–258° C.

$^1$H-NMR (DMSO) δ: 10.51(broad,1H); 8.82(broad,1H); 8.63(s,2H); 8.21–7.57(m,3H); 4.60(s,2H); 4.35(s,2H); 3.96(s,3H).

EXAMPLE 92

1-(3,5-Dichloro-pyridin-4-ylmethyl)-6-methoxy-4-[1,2,4]triazol-1-yl-phthalazine 3-oxide (Compound 52)

Under $N_2$ at 0° C. a solution of 1-(3,5-dichloro-pyridin-4-ylmethyl)-6-methoxy-4-[1,2,4]triazol-1-yl-phthalazine (5.1 g, 13.2 mmoles), prepared as described in example 51, in trifluoroacetic acid (25 ml), was dropwise added with $H_2O_2$ (1.35 ml, 13.5 mmoles). The temperature was left to rise to the room value and, after 48 hours, the pH was adjusted with NaOH. After further 24 hours under stirring, the mixture was dried, taken up in $CH_2Cl_2$. The organic phase was washed with water, anhydrified and dried to give a foam which was flash chromatographed (eluent: ethyl acetate/ethyl ether 6:4, then 8:2) to give 2.2 g of the title compound (yield: 41%). m.p.: 218–220° C. (dec.).

$^1$H-NMR (CDCl$_3$) δ: 9.12 and 8.26(2s,2H); 8.42(s,2H); 8.48–7.49(m,3H); 4.90(s,2H); 3.98(s,3H).

EXAMPLE 93

6-Hydroxy-3H-isobenzofuran-1-one

A solution of 6-methoxy-3H-isobenzofuran-1-one (50 g, 0.3 moles), prepared as described in example 34, in $CH_2Cl_2$ (250 ml) under $N_2$ at −5° C., was dropwise added with BBr$_3$ (360 ml, 0.36 moles). At the end of the addition the solution was stirred at room temperature overnight, then cooled and added with further BBr$_3$ (60 ml, 60 mmoles). The stirring was kept on for 4 hours at room temperature. The mixture was cooled and added with $CH_3OH$ (250 ml), then dried under vacuum to give a solid which was triturated in ethyl ether and washed with ethyl ether and ethyl acetate. After drying under vacuum at 40° C. a solid was obtained which was joined to the solid yielded by drying the mother liquors, discolouring and triturating in ethyl ether. There were obtained 33.51 g of the title compound (yield: 73%).

$^1$H-NMR (DMSO) δ: 10.05(s,1H); 7.50–7.08(m,3H); 5.29(s,2H).

EXAMPLE 94

6-Difluoromethoxy-3H-isobenzofuran-1-one

In autoclave a solution of 6-hydroxy-3H-isobenzofuran-1-one (34.06 g, 0.227 moles), prepared as described in example 93, in DMF (340 ml) was added with $K_2CO_3$ (34.5 g, 0.25 moles), and put under freon atmosphere. After 1 night under vigorous stirring at 110° C., the mixture was cooled and the $K_2CO_3$ filtered off. The solution was dried to give a solid which was taken up in water/ethyl acetate. The insoluble was filtered and treated with water and ethyl acetate. The organic phase was anhydrified and dried under vacuum to give an oil which was taken up in $CHCl_3$. The solution was flash chromatographed (eluent: petrolatum/ethyl acetate 7:3) to give 24.1 g of the title compound (yield: 53%).

$^1$H-NMR ($CDCl_3$) δ: 7.61–7.40(m,3H); 6.56(t, 1H,J=72 Hz); 5.29(s,2H).

EXAMPLE 95

3-Bromo-6-difluoromethoxy-3H-isobenzofuran-1-one

A suspension of 6-difluoromethoxy-3H-isobenzofuran-1-one (1 g, 5 mmoles), prepared as described in example 94, in $CCl_4$ (10 ml), under $N_2$, was added with N-bromosuccinimide (0.91 g, 5.1 mmoles) and the mixture was heated at 76° C. A solution of α,α'-azaisobutyronitrile (0.01 g) in $CHCl_3$ (1 ml) was slowly added. The mixture was refluxed for 1.5 hours, then cooled, filtered over celite and washed with $CCl_4$. By drying, 1.41 g of the title compound were obtained as an oil (quantitative yield).

$^1$H-NMR ($CDCl_3$) δ: 7.65–7.49(m,3H); 7.37(s,1H); 6.60 (t,1H,J=72 Hz).

EXAMPLE 96

(5-Difluoromethoxy-3-oxo-1,3-dihydro-isobenzofuran-1-yl)triphenyl-phosphonium bromide Under $N_2$, a solution of 3-bromo-6-difluoromethoxy-3H-isobenzofuran-1-one (6.2 g, 22.2 mmoles), prepared as described in example 95, in dry acetonitrile (30 ml) was added with triphenylphosphine (6.4 g, 24.4 mmoles). After 4 hours under reflux the mixture was dried to give a foam which was triturated in ethyl ether overnight, then filtered, washed with ethyl ether and dried to give 11.4 g of the title compound (yield: 95%).

$^1$H-NMR ($CDCl_3$) δ: 9.96(s,1H); 7.89–7.16(m,18H); 6.58 (t,1H,JH=72 Hz).

EXAMPLE 97

3-(3,5-Dichloro-pyridin-4-ylmethylene)-6-difluoromethoxy-3H-isobenzofuran-1-one

A solution of (5-difluoromethoxy-3-oxo-1,3-dihydro-isobenzofuran-1-yl)triphenyl-phosphonium bromide (11.4 g, 21 mmoles), prepared as described in example 96, in dry $CH_2Cl_2$ (110 ml), under $N_2$, was added with 3,5-dichloro-4-formyl-pyridine (4.06 g, 23.1 mmoles). The mixture was cooled to 4° C. and added with triethylamine (3.8 ml, 27.3 mmoles) while keeping the temperature below 10° C. At the end of the addition the mixture was stirred at room temperature for 3 hours, then cooled and added with 5% HCl. The organic phase was washed with an aqueous NaCl solution, discoloured with charcoal, filtered over celite and dried to give 14.4 g of the title compound (stoichiometric yield; containing 1 equivalent of triphenylphosphine oxide).

$^1$H-NMR ($CDCl_3$) δ: 8.62(s,2H); 8.29–7.78(m,4H); 6.59 (t,1H,$J_{HF}$=72 Hz).

EXAMPLE 98

4-(3,5-Dichloro-pyridin-4-ylmethyl)-7-difluoromethoxy-2H-phthalazin-1-one (Compound 53)

A solution of 3-(3,5-dichloro-pyridin-4-ylmethylen)-6-difluoromethoxy-3H-isobenzofuran-one (14.4 g, 21 mmoles), prepared as described in example 97, in $CH_3OH$ (100 ml), under $N_2$, was added with acetic acid (3.6 ml, 63 mmoles) and hydrazine monohydrate (3.15 ml, 63 mmoles). A precipitate formed and the mixture was refluxed for 2 hours. After 1 night to stand the mixture was cooled over ice and the solid filtered and washed with little $CH_3OH$. After drying under vacuum at 50° C., 6.64 g of the title compound were obtained [yield: 85% from (5-difluoromethoxy-3-oxo-1,3-dihydro-isobenzofuran-1-yl)-triphenyl-phosphonium bromide].

$^1$H-NMR ($CDCl_3$) δ: 12.54(s,1H); 8.65(s,2H); 8.36–7.80 (m,3H); 7.58(t,1H,$J_{HF}$=74 Hz); 4.62(s,2H).

EXAMPLE 99

4-Chloro-1-(3,5-dichloro-pyridin-4-ylmethyl)-6-difluoromethoxy-phthalazine

A suspension of 4-(3,5-dichloro-pyridin-4-ylmethyl)-7-difluoromethoxy-2H-phthalazin-1-one (6.64 g, 17.8 mmoles), prepared as described in example 98, in acetonitrile (70 ml), under $N_2$, was added with $POCl_3$ (8.3 ml, 89 mmoles). After 4.5 hours under reflux and 1 night to stand, the mixture was dried under vacuum, taken up in $CH_2Cl_2$ and washed with an aqueous $Na_2CO_3$ solution, then discoloured with charcoal, filtered over celite and dried again to give 6.8 g of the title compound (yield: 97%).

$^1$H-NMR ($CDCl_3$) δ: 8.50(s,2H); 8.29–7.78(m,3H); 6.77 (t,1H,$J_{HF}$=72 Hz); 4.89(s,2H).

EXAMPLE 100

1-(3,5-Dichloro-pyridin-4-ylmethyl)-6-difluoromethoxy-4-[1,2,4]triazol-1-yl-phthalazine (Compound 54)

A solution under $N_2$ of 1,2,4-triazole (2.4 g, 34.8 mmoles) in DMF (100 ml) was added with NaH (1.05 g, 26.1 mmoles). The mixture was stirred at room temperature up to clarity, then added with 4-chloro-1-(3,5-dichloro-pyridin-4-ylmethyl)-6-difluoromethoxy-phthalazine (6.8 g, 17.4 mmoles), prepared as described in example 99. The mixture was heated at 100° C. for 5 hours, extracted three times with $CH_2Cl_2$. The organic phase was anhydrified and dried to give a solid which was flash chromatographed (eluent: ethyl acetate/petrolatum 7:3 to 100% of ethyl acetate) to give 4.14 g of the title compound (yield: 28%). m.p.: 220–224° C.

¹H-NMR (CDCl₃) δ: 9.26 and 827(2s,2H); 8.97(d,1H,J= 2.4 Hz); 8.55(s,2H); 8.36(d,1H,J=7.2 Hz); 7.86(dd,1H); 6.79(t,1H,J=72 Hz); 4.97(s,2H).

EXAMPLE 101

1-(3,5-Dichloro-pyridin-4-ylmethyl)-6-difluoromethoxy-4-morpholin-4-yl-phthalazine (Compound 55)

A suspension under $N_2$ of 4-chloro-1-(3,5-dichloro-pyridin-4-ylmethyl)-6-difluoromethoxy-phthalazine (5.5 g, 14.1 mmoles), prepared as described in example 99, in morpholine (11 ml) was heated at 100° C. for 1 hour, then cooled and poured into water (150 ml). A solid formed and was stirred for 15 minutes, then filtered, washed with water, dried over $P_2O_5$ at 50° C. under high vacuum. There were obtained 6 g of the title compound (yield: 96%). m.p.: 128.6–130.6° C.

¹H-NMR (CDCl₃) δ: 8.49(s,2H); 8.20–7.65(m,3H); 6.70 (t,1H,J=71.9 Hz); 4.81(s,2H); 3.95–3.91 (m,4H); 3.47–3.42 (m,4H).

EXAMPLE 102

4-(3,5-Dichloro-pyridin-4-ylmethyl)-7-methoxy-phthalazin-1-carboxylic acid methyl ester A suspension of 4-chloro-1-(3,5-dichloro-pyridin-4-ylmethyl)-6-methoxy-phthalazine (9.7 g, 27 mmoles), prepared as described in example 45, in DMSO/CH₃OH (80/40 ml) was added with $K_2CO_3$ (7.4 g, 54 mmoles), palladium acetate (0.31 g, 1.4 mmoles) and 1,3-bis(diphenylphosphine)propane (0.75 g, 1.82 mmoles). The mixture was placed in autoclave under CO atmosphere (8 bar) and heated at 50° C. After 4 hours the mixture was poured into water (10 volumes) and extracted four times with ethyl acetate. The organic phase was washed with aqueous NaCl and discoloured with charcoal, filtered and dried to give a solid which was flash chromatographed (eluent: petrolatum/ethyl acetate 1:1) to give 5 g of the title compound (yield: 49%).

¹H-NMR (CDCl₃) δ: 8.48(s,2H); 8.22–7.55(m,3H); 4.91 (s,2H); 4.02 and 4.01(2s,6H).

EXAMPLE 103

[4-(3,5-Dichloro-pyridin-4-ylmethyl)-7-methoxy-phthalazin-1-yl]-methanol

A suspension of 4-(3,5-dichloro-pyridin-4-ylmethyl)-7-methoxy-phthalazin-1-carboxylic acid methyl ester (3.9 g, 10.3 mmoles), prepared as described in example 102, in DMF/CH₃OH (30/50 ml) under $N_2$ was portionwise added with NaBH (1.17 g, 30.9 mmoles) in 1.5 hours. The stirring went on for 2.5 hours. The mixture was cooled on ice and added with concentrated HCl up to pH<1, then dried, taken up in water and extracted three times with $CH_2Cl_2$, the organic phase was anhydrified and dried to give 3.5 g of the title compound (yield: 97%). m.p.: 190–195° C.

¹H-NMR (CDCl₃) δ: 8.51(s,2H); 8.20–7.10(m,3H); 5.22 (s,2H,J=4.4 Hz); 4.90(s,2H); 4.50(t,1H); 4.01(s,3H).

EXAMPLE 104

1-(3,5-Dichloro-pyridin-4-ylmethyl)-6-methoxy-4-morpholin-4-ylmethyl-phthalazine (Compound 56)

A suspension under $N_2$ of [4-(3,5-dichloro-pyridin-4-ylmethyl)-6-methoxy-phthalazin-1-yl]-methanol (1.25 g, 3.6 mmoles), prepared as described in example 103, in $CH_2Cl_2$ (30 ml) was added with triethylamine (0.75 ml, 5.4 mmoles). The mixture was cooled to 0–4° C. and dropwise added with methanesulfonyl chloride (0.33 ml, 4.32 mmoles) in $CH_2Cl_2$ (5 ml). At the end of the addition the resultant solution was stirred for 1 hour at room temperature, then cooled and added with morpholine (0.94 ml, 10.8 mmoles). The mixture was stirred at room temperature for 3 hours, then poured into 5% HCl. The acidic phase was alkalinised and twice extracted with $CH_2Cl_2$, then discoloured with charcoal, filtered over celite and dried to give a foam which was flash chromatographed (eluent: $CH_2Cl_2$/CH₃OH 98:2). The yielded foam was triturated in ethyl ether to give 1.1 g of the title compound (yield: 52%). m.p.: 202.6–205.6° C.

¹H-NMR (CDCl₃) δ: 8.49(s,2H); 8.14–7.52(m,3H); 4.87 (s,2H); 4.10(s,2H); 4.00(s,3H); 3.68–3.64(m,4H); 2.57–2.52 (m,4H).

EXAMPLE 105

1-(3,5-Dichloro-pyridin-4-ylmethyl)-6-methoxy-4-pyrrolidin-1-ylmethyl-phthalazine (Compound 57)

Operating analogously to what described in example 104 starting from [4-(3,5-dichloro-pyridin-4-ylmethyl)-6-methoxy-phthalazin-1-yl]-methanol (1.75 g, 5 mmoles), prepared as described in example 103, in $CH_2Cl_2$ (30 ml), triethylamine (1 ml, 7.5 mmoles), methanesulfonyl chloride (0.47 ml, 6 mmoles) in $CH_2Cl_2$ (5 ml), and pyrrolidine (1.24 ml, 15 mmoles), 1.04 g of the title compound were obtained (yield: 51%). m.p.: 174.6–176.6° C.

¹H-NMR (CDCl₃) δ: 8.48(s,2H); 8.12–7.49(m,3H); 4.86 (s,2H); 4.19(s,2H); 4.00(s,3H); 2.63–2.57(m,4H); 1.77–1.71 (m,4H).

EXAMPLE 106

1-(3,5-Dichloro-pyridin-4-ylmethyl)-6-methoxy-4-(3-moroholin-4-yl-propl-ynyl)-phthalazine (Compound 58)

A solution under $N_2$ of 4-chloro-1-(3,5-dichloro-pyridin-4-ylmethyl)-6-methoxy-phthalazine (1.3 g, 3.7 mmoles), prepared as described in example 45, in dry DMF (50 ml) was added with $K_2CO_3$ (1.28 g, 9.25 mmoles), palladium acetate (0.017 g, 0.074 mmoles), CuI (0.028 g, 0.15 mmoles), and triphenylphosphine (0.58 g, 0.22 mmoles). After 30 minutes under stirring 4-prop-2-ynyl-morpholine (1.16 g, 9.25 mmoles) was added and the mixture was stirred overnight, poured into water (10 volumes) and extracted twice with ethyl acetate. After decolouring with charcoal, filtering over celite, concentrating and triturating in ethyl ether, 1.15 g of the title compound were obtained (yield: 70%). m.p.: 171.7–172.7° C. (dec.).

¹H-NMR (CDCl₃) δ: 8.49(s,2H); 8.13–7.54(m,3H); 4.88 (s,2H); 4.02(s,3H); 3.77–3.72(m,4H); 3.72(s,2H); 2.76–2.71 (m,4H).

EXAMPLE 107

4-[4-(3,5-Dichloro-pyridin-4-ylmethyl)-7-methoxy-phthalazin-1-yl]-2-methyl-but-3-yn-2-ol (Compound 59)

Operating analogously to what described in example 106 starting from 4-chloro-1-(3,5-dichloro-pyridin-4-ylmethyl)-6-methoxy-phthalazine (1 g, 2.8 mmoles), prepared as described in example 45, in dry DMF (25 ml), $K_2CO_3$ (0.97 g, 7 mmoles), palladium acetate (0.013 g, 0.056 mmoles), CuI (0.021 g, 0.11 mmoles), triphenylphosphine (0.044 g, 0.17 mmoles) and 2-methyl-3-butyn-2-ol (0.59 g, 7 mmoles), 0.93 g of the title compound were obtained. m.p.: 203.6–205.6° C. (dec.).

$^1$H-NMR (CDCl$_3$) δ: 8.48(s,2H); 8.10–7.52(m,3H); 4.87 (s,2H); 4.00(s,3H); 2.65(s,1H); 1.70(s,6H).

EXAMPLE 108

1-(3,5-Dichloro-pyridin-4-ylmethyl)-4-ethynyl-6-methoxy-phthalazine (Compound 60)

In a Claisen flask, a suspension under N$_2$ of 4-[4-(3,5-dichloro-pyridin-4-ylmethyl)-7-methoxy-phthalazin-1-yl]-2-methyl-but-3-yn-2-ol (0.4 g, 1 mmole), prepared as described in example 107, in dry toluene (50 ml) was added with a catalytic amount of NaH, the mixture was refluxed, then distilled up to half volume. The mixture was left to stand overnight, then poured into water, extracted three times with CH$_2$Cl$_2$, discoloured with charcoal, filtered over celite and dried to give a solid which was triturated in ethyl ether to give 0.21 g of the title compound. m.p.: 210.3–211.3° C. (dec.).

$^1$H-NMR (CDCl$_3$) δ: 8.49(s,2H); 8.14–7.54(m,3H); 4.90 (s,2H); 4.03(s,3H); 3.62(s, 1H).

EXAMPLE 109

4-(3,5-Dichloro-pyridin-4-ylmethyl-7-methoxy-phthalazine-1-carboxylic acid amide (Compound 61)

An excess of NH$_3$ was bubbled into a suspension of 4-(3,5-dichloro-pyridin-4-ylmethyl)-7-methoxy-phthalazin-1-carboxylic acid methyl ester (1.6 g, 4.23 mmoles), prepared as described in example 102, in dry CH$_3$OH, under stirring and dry N$_2$ at 10° C., and the mixture was left for 3 hours at room temperature, then refluxed for 1.5 hours in environment saturated of NH$_3$. After 2 days at room temperature, the mixture was dried to give 1.48 g of the title compound (yield: 67.7%).

$^1$H-NMR (CDCl$_3$) δ: 9.00–7.57(m,3H); 8.53(s,2H); 4.95 (s,2H); 4.05(s,3H).

EXAMPLE 110

4-(3,5-Dichloro-pyridin-4-ylmethyl)-7-methoxy-phthalazine-1-carbonitrile (Compound 62)

A solution of 4(3,5-dichloro-pyridin-4-ylmethyl)-7-methoxy-phthalazine-1-carboxylic acid amide (1.06 g, 2.92 mmoles), prepared as described in example 109, in pyridine (80 ml) and trifluoroacetic anhydride (1.65 ml, 11.67 mmoles), under dry N$_2$ at room temperature, was stirred for 3 hours, then dried, taken up in CH$_2$Cl$_2$, washed with citric acid, 5% NaOH and water. The organic phase was anhydrified and dried to give a solid which was flash chromatographed (eluent: CH$_2$Cl$_2$/CH$_3$OH 99:1) to give 0.33 g of the title compound (yield: 33%).

$^1$H-NMR (CDCl$_3$) δ: 8.52(s,2H); 8.22(d,1H,J=9.2 Hz); 7.69(dd,1H); 7.47(d,1H,J=2.5 Hz); 4.96(s,2H); 4.07(s,3H).

EXAMPLE 111

4-(3,5-Dichloro-pyridin-4-ylmethyl)-7-methoxy-1-phenyl-1,2-dihydro-phthalazine (Compound 63)

1-(3,5-Dichloro-pyridin-4-ylmethyl)-4-phenyl-6-methoxy-phthalazine (0.5 g, 1.26 mmoles), prepared as described in example 47, in THF (40 ml) was added with platinum oxide hydrate (catalytic amount), then hydrogenated in a Parr at 4 atmospheres under stirring for 4 days and at 50° C. for 24 hours. The catalyst was filtered off and the mixture dried to give a solid which flash chromatographed (eluent: petrolatum/ethyl acetate 8:2) giving 0.16 g of the title compound (yield: 32%). m.p.: 175.3–177.3° C.

$^1$H-NMR (CDCl$_3$) δ: 8.45(s,2H); 7.42–6.27(m,8H); 5.78 (s,1H); 5.21(s,1H); 4.36–4.15(m,2H); 3.71(m,3H).

EXAMPLE 112

4-(3,5-Dichloro-pyridin-4-ylmethyl)-2-methanesulfonyl-7-methoxy-1-phenyl-1,2-dihydro-phthalazine (Compound 64)

4-(3,5-Dichloro-pyridin-4-ylmethyl)-7-methoxy-1-phenyl-1,2-dihydrophthalazine (0.16 g, 0.4 mmole), prepared as described in example 111, in dry CH$_2$Cl$_2$ (10 ml), under N$_2$, was added with triethylamine (0.1 ml, 0.72 mmole) and methanesulphonyl chloride (0.037 ml, 0.48 mmole). The mixture was stirred at room temperature overnight, then added again with triethylamine (0.05 ml, 0.36 mmole) and methanesulphonyl chloride (0.02 ml, 0.24 mmole). After 4 hours methanesulphonyl chloride (0.04 ml, 0.48 mmole) and 1,8-diazabicyclo[5.4.0]undec-7-ene (0.085 ml, 0.56 mmole) were added. After 24 hours the mixture was poured into water and the aqueous phase separated and extracted with CH$_2$Cl$_2$. The organic phase was washed in diluted citric acid, anhydrified and dried to give a solid which was flash chromatographed (eluent: petrolatum/ethyl acetate 7:3). The resultant solid was triturated in ethyl ether to give 0.21 g of the title compound (quantitative yield).

m.p.: 222.6–224.4° C.

$^1$H-NMR (CDCl$_3$) δ: 8.47(s,2H); 7.60(d,1H,J=8.7 Hz); 7.28–7.24(m,5H); 6.94(dd,1H); 6.64(d,1H,J=2.6 Hz); 6.23 (s,1H); AB system: Va=4.51, Vb=4.33, Jab=16.3 Hz); 3.80 (s,3H); 2.21(s,3H).

EXAMPLE 113

4-(6-Methoxy-4-oxo-3,4-dihydro-phthalazin-1-yl)-butyric acid methyl ester (Compound 65)

A solution of 3-formyl-propionic acid methyl ester (13.4 g, 0.1155 moles) and (5-methoxy-3-oxo-1,3-dihydro-isobenzofuran-1-yl)-triphenyl-phosphonium bromide (55.6 g, 0.11 moles), prepared as described in example 36, in CH$_2$Cl$_2$ (440 ml) in water bath was dropwise added with triethylamine (16.1 ml, 0.1155 mole). At the end of the addition the mixture was stirred at room temperature overnight, then washed with water, anhydrified and dried to give a residue which was taken up in ethanol (180 ml). The solution was cooled and added with hydrazine monohydrate (11 g, 0.22 mole). A precipitate formed and was filtered. After 6 days the mother liquors gave a precipitate which joined to the previous one yielded 23 g of the title compound (yield: 75.5%). m.p.: 175–177° C.

$^1$H-NMR (DMSO) δ: 12.40(broad, 1H); 7.96–7.45(m, 3H); 3.92(s,3H); 3.57(s,3H); 2.92–2.85(m,2H); 2.48–2.40 (m,2H); 2.00–1.84(m,2H).

EXAMPLE 114

4-(4-Chloro-6-methoxy-phthalazin-1-yl)-butyric acid methyl ester

A suspension of 4-(6-methoxy-4-oxo-3,4-dihydro-phthalazin-1-yl)-butyric acid methyl ester (9.23 g, 0.034 moles), prepared as described in example 113, and POCl$_3$ (1.87 ml, 0.2 mole) in acetonitrile (100 ml) was refluxed. After 1.5 hours the mixture was dried, taken up in water and neutralised with NaHCO$_3$. The mixture was extracted with ethyl acetate and the organic phase dried to give a residue which was chromatographed (eluent: petrolatum/ethyl acetate 7:3). There were yielded 7.4 g of the title compound (yield: 63.9%).

EXAMPLE 115

4(6-Methoxy-4-thiazol-2-yl-phthalazin-1-yl)-butyric acid methyl ester (Compound 66)

Operating analogously at what described in example 48 starting from 4-(4-chloro-6-methoxy-phthalazin-1-yl)-butyric acid methyl ester (12.5 g, 0.0424 mole), prepared as described in example 114, zinc (17.3 g), 2-bromothiazole (24.3 g, 0.1484 mole), palladium acetate (0.476 g, 2.12 mmole), triphenylphosphine (1.67 g, 6.36 mmole), 3.8 g of the title compound were obtained (yield: 12.6%). m.p.: 136–137° C.

$^1$H-NMR (CDCl$_3$) δ: 9.24(d,1H,J=2.7); 8.11(d,1H,J=9.1); 8.04(d,1H,J=3.3); 7.53–7.47(m,2H); 4.03(s,3H); 3.67(s,3H); 3.42–3.34(m,2H); 2.57–2.50(m,2H); 2.33–2.19(m,2H).

EXAMPLE 116

N-hydroxy-4-(6-methoxy-4-thiazol-2-yl-phthalazin-1-yl)-butyramide (Compound 67)

A solution of sodium (388 mg, 16.9 mmoles) in CH$_3$OH (6 ml) was added with hydroxylamine hydrochloride (1.3 g, 18.71 mmoles). The resultant solution was added to a solution of 4-(6-methoxy-4-thiazol-2-yl-phthalazin-1-yl)-butyric acid methyl ester (1.5 g, 4.4 mmoles), prepared as described in example 115, in CH$_3$OH (30 ml), and stirred at room temperature for 2 days, then refluxed for 7 hours. NH$_2$OH.HCl (1.6 g) and sodium (450 mg) were added, and the mixture was refluxed. After 1 night further NH$_2$OH.HCl (0.9 g) and sodium (257 mg) were added, and the mixture was refluxed for 24 hours. The precipitate was filtered off and the mother liquors dried, taken up in water and filtered. The resultant solid was chromatographed (eluent: CH$_2$Cl$_2$/CH$_3$OH 95:5) to give a solid which was suspended in water, dissolved in 10% NaOH and precipitated with saturated ammonium chloride to give 430 mg of the title compound (yield: 28.6%). m.p.: 189–190° C. (dec.).

$^1$H-NMR (DMSO) δ: 10.36 and 8.72(2 broad,2H); 9.15 (d,1H,J=2.6); 8.32(d,1H,J=9.2); 8.19(d,1H,J=3.3); 7.99(d,1H); 7.70(dd,1H); 3.99(s,3H); 3.35–3.27(m,2H); 2.18–1.97 (m,4H).

EXAMPLE 117

4-(6-Methoxy-4-thiazol-2-yl-phthalazin-1-yl)-butyramide (Compound 68)

A suspension of 4-(6-methoxy-4-thiazol-2-yl-phthalazin-1-yl)-butyric acid methyl ester (1.2 g, 3.5 mmoles), prepared as described in example 115, in NH$_3$/THF (10 ml) was added with THF (15 ml), then placed in autoclave at 85° C. After 1 night the mixture was dried, taken up in CH$_3$OH (30 ml) and saturated with NH$_3$ at 0° C., then heated at 85° C. for 44 hours. The mixture was cooled and dried to give a residue which was chromatographed (eluent: CH$_2$Cl$_2$/CH$_3$OH 95:5 to 90:10). The solid was triturated in CH$_2$Cl$_2$ to give 840 mg of the title compound (yield: 73.1%)

$^1$H-NMR (DMSO) δ: 9.15(d,1H,J=2.6); 8.35(d,1H,J=9.2); 8.19(d,1H,J=3.2); 7.99(d,1H); 7.69(dd,1H); 7.30 and 6.77(2s broad,2H); 3.99(s,3H); 3.35–3.28(m,2H); 2.26–2.19 (m,2H); 2.09–1.95(m,2H).

EXAMPLE 118

4-(6-Methoxy-4-thiazol-2-yl-phthalazin-1-yl)-butyric acid (Compound 69)

4-(6-Methoxy-4-thiazol-2-yl-phthalazin-1-yl)-butyric acid methyl ester (1.2 g, 3.5 mmoles), prepared as described in example 115, was dissolved in warm CH$_3$OH (30 ml) and added with 10% NaOH (2.8 ml, 7 mmoles), then refluxed. After 30 minutes the mixture was cooled, dried, taken up in water and extracted with CH$_2$Cl$_2$. The aqueous phase was discoloured with charcoal and acidified with acetic acid. The precipitate was filtered, washed with water and dried to give 0.95 g of the title compound (yield: 82.4%). m.p.: 218–220° C.

$^1$H-NMR (DMSO) δ: 12.11(s,1H); 9.13(d,1H,J=2.7); 8.32 (d,1H,J=9.2); 8.18(d,1H,J=3.3); 7.98(d,1H); 7.67(dd,1H); 3.98(s,3H); 3.37–3.29(m,2H); 2.45–2.38(m,2H); 2.11–1.96 (m,2H).

EXAMPLE 119

3-(6-Methoxy-4-oxo-3,4-dihydro-phthalazin-1-yl)-propionic acid ethyl ester (Compound 70)

Operating analogously to what described in example 113 starting from potassium 2-ethoxycarbonyl-ethenolate (771 mg, 5 mmoles), (5-methoxy-3-oxo-1,3-dihydro-isobenzofuran-1-yl)-triphenyl-phosphonium bromide (2.53 g, 5 mmoles), prepared as described in example 36, CH$_2$Cl$_2$ (20 ml) and hydrazine monohydrate (250 mg, 5 mmoles) in ethanol (20 ml), 0.52 g of the title compound were obtained.

$^1$H-NMR (CDCl$_3$) δ: 7.80–7.35(m,3H); 4.13(q,2H); 3.95 (s,3H); 3.28–2.77(m,4H); 1.23(t,3H,J=7.1).

EXAMPLE 120

3-(3-Methanesulfonyl-6-methoxy-4-oxo-3,4-dihydro-phthalazin-1-yl)-propionic acid ethyl ester (Compound 71)

A suspension of 3-(6-methoxy-4-oxo-3,4-dihydro-phthalazin-1-yl)-propionic acid ethyl ester (4 g, 0.0145 mole), prepared as described in example 119, and NaH (0.638 g, 0.016 mole) in acetonitrile (80 ml) was heated at 55° C. After 2 hours the mixture was cooled, added with methanesulfonyl chloride (1.35 ml, 0.017 mole), and stirred at room temperature overnight. K$_2$CO$_3$ (2 g, 0.0145 mole) and methanesulfonyl chloride (1.12 ml, 0.0145 mole) were added, and the mixture was stirred overnight, then dried and partitioned between water and CHCl$_3$. The organic phase was washed with a K$_2$CO$_3$ solution, anhydrified and dried to give a residue which was chromatographed (eluent: CH$_2$Cl$_2$/ethyl acetate 95:5). The resultant solid was crystallised from acetonitrile (5 ml) to give 0.9 g of the title compound (yield: 17.5%).

$^1$H-NMR (DMSO) δ: 7.81(d,1H); 7.78(d,1H); 4.41(dd, 1H,J=8.9 Hz,2.8 Hz); 4.15(q,2H); 3.95(s,3H); 3.55(s,3H); 3.31–3.24(m,2H); 2.90–2.83(m,2H); 1.26(t,3H,J=7.1).

EXAMPLE 121

3-(4-Chloro-6-methoxy-phthalazin-1-yl)-propionic acid ethyl ester

Operating analogously to example 114 starting from 3-(6-methoxy-4-oxo-3,4-dihydrophthalazin-1-yl)-propionic acid ethyl ester (552 mg, 2 mmoles), prepared as described in example 119, and POCl$_3$ (1.12 ml, 12 mmoles) in acetonitrile (5 ml), 0.5 g of the title compound were obtained (yield: 84.8%).

EXAMPLE 122

3-(6-Methoxy-4-thiazol-2-yl-phthalazin-1-yl)-propionic acid ethyl ester (Compound 72)

Operating analogously at what described in example 48 starting from 3-(4-chloro-6-methoxy-phthalazin-1-yl)-propionic acid ethyl ester (4.5 g, 0.0153 mole), prepared as described in example 121, zinc (2.2 g), 2-bromothiazole (5 g, 0.0305 mole), palladium acetate (180 mg, 0.8 mmole), triphenyphosphine (630 mg, 2.4 mmoles), 1.4 g of the title compound were obtained (yield: 21%). m.p.: 153–154° C.

$^1$H-NMR (CDCl$_3$) δ: 9.26(d,1H,J=2.7); 8.11(d,1H,J=9.2); 8.09(d,1H,J=3.2); 7.52(dd,1H); 7.50(d, 1H); 4.15(q,2H); 4.04(s,3H); 3.68–3.61 (m,2H); 3.16–3.09 (m,2H); 1.24(t, 3H,J=7.1).

EXAMPLE 123

3-(6-Methoxy-4-thiazol-2-yl-phthalazin-1-yl)-propionic acid (Compound 73)

Operating analogously to what described in example 118 starting from 3-(6-methoxy-4-thiazol-2-yl-phthalazin-1-yl)-propionic acid ethyl ester (1.05 g, 3.06 mmoles), prepared as described in example 122, CH$_3$OH (25 ml) and 10% NaOH (2.5 ml, 6.25 mmoles), 0.8 g of the title compound were obtained (yield: 82.9%). m.p.: 228–229° C.

$^1$H-NMR (DMSO) δ: 12.7(s,1H); 9.14(d,1H,J=2.6); 8.33 (d,1H,J=9.3); 8.19 and 7.99(2d,2H,J=3.3); 7.69(dd, 1H); 3.99(s,3H); 3.60–3.54(m,2H); 2.96–2.89(m,2H).

EXAMPLE 124

N-hydroxy-3-(6-Methoxy-4-thiazol-2-yl-phthalazin-1-yl)-propionamide (Compound 74)

A solution of 3-(6-methoxy-4-thiazol-2-yl-phthalazin-1-yl)-propionic acid (200 mg), prepared as described in example 123, H$_2$SO$_4$ (3 drops) and CH$_3$OH (15 ml) was refluxed overnight, then discoloured with charcoal, neutralised with Na$_2$CO$_3$ and dried. The residue was partitioned between ethyl acetate and water, the organic phase was anhydrified and dried to give a residue (A). In another flask, sodium (47 mg, 2.04 mmoles) in CH$_3$OH (2 ml) was added with NH$_2$OH.HCl (142 mg, 2.04 mmoles) and with the residue A in CH$_3$OH (12 ml). The mixture was refluxed under N$_2$ for 2 hours, then stirred at room temperature for 4 days. A precipitate formed, the whole was cooled in water/ice, filtered, washed with water and dried to give 75 mg of the title compound (yield: 53.4%).

$^1$H-NMR (DMSO) δ: 10.51 and 8.72(2s,2H); 9.16(d,1H, J=2.6); 8.33(d,1H,J=9.1); 8.20(d,1H,J=3.3); 7.99(d,1H); 7.71(dd,1H); 4.00(s,3H); 3.57(t,2H,J=7.3); 2.64(t,2H).

EXAMPLE 125

Sodium 1-[4-(3,5-dichloro-pyridin-4-ylmethyl)-7-methoxy-phthalazin-1-yl]-pyrrolidine-2-carboxylate (Compound 75)

A suspension of L(–)-proline (5.2 g, 0.045 mole) in acetonitrile (50 ml), under N$_2$, was added with NaH (0.9 g, 0.0375 mole), and the mixture stirred for 1 hour at room temperature. 4-Chloro-1-(3,5-dichoro-pyridin-4-ylmethyl)-6-methoxy-phthalazine (5.32 g, 0.015 mole), prepared as described in example 45, was added and the mixture refluxed. After 2 days the mixture was dried under vacuum, the residue taken up in water and extracted with CH$_2$Cl$_2$. The alkaline aqueous phase was discoloured with charcoal, filtered over celite, and the filtrate acidified (pH=4) with 10% HCl and extracted three times with CH$_2$Cl$_2$. The organic phase was anhydrified over Na$_2$SO$_4$ and dried. The residue was salified with sodium methoxide, dissolved in CH$_3$OH and dried. The salt was triturated with warm tert-butylmethyl ether (100 ml), cooled in water/ice and filtered to give 6.4 g of the title compound (yield: 84.3%).

$^1$H-NMR (DMSO) δ: 8.10(s,2H); 8.10(d,1H,J=9.0); 7.79 (d,1H,J=2.4); 7.45(dd,1H); 4.64(s,2H); 4.65–4.58(m,1H) ;3.92(s,3H); 3.78–3.66(m,2H); 2.24–1.66(m,4H).

EXAMPLE 126

4-Furan-2-ylmethyl-7-methoxy-2H-phthalazin-1-one (Compound 76)

A mixture of (5-methoxy-3-oxo-1,3-dihydro-isobenzofuran-1-yl)-triphenyl-phosphonium bromide (8 g, 15.83 mmoles), prepared as described in example 36, CH$_2$Cl$_2$ (100 ml) and furfural (1.31 ml, 15.83 mmoles), cooled in ice and under N$_2$, was dropwise added with triethylamine (2.2 ml, 15.83 mmoles). The cooling was removed and the mixture was stirred for 1.5 hours, then washed with water, anhydrified over Na$_2$SO$_4$ and dried. The residue was dissolved in CH$_3$OH (50 ml) and added with hydrazine monohydrate (2.3 ml, 47.49 mmoles). The mixture was refluxed for 1 hour, then concentrated to half volume. A precipitate crystallised and dried under vacuum at 40° C. gave 1.82 g of the title compound (yield: 45%).

$^1$H-NMR (DMSO) δ: 12.50(s,1H); 7.96–7.43(m,3H); 7.51–6.20(m,3H); 4.27(s,2H); 3.91(s,3H).

EXAMPLE 127

4-Chloro-1-furan-2-ylmethyl-6-methoxy-phthalazine

A suspension under N$_2$ of 4-furan-2-ylmethyl-7-methoxy-2H-phthalazin-1-one (1.8 g, 7.02 mmoles), prepared as described in example 126, in acetonitrile (40 ml) was added under stirring with POCl$_3$ (3.27 ml, 35.1 mmoles), and refluxed for 1 hour, then dried. The residue was suspended in water (50 ml), added with NaHCO$_3$ up to alkalinity, and stirred for 30 minutes, then extracted in CH$_2$Cl$_2$. The organic phase was anhydrified over Na$_2$SO$_4$ and dried to give a residue which was taken up in petrolatum and filtered. The resultant solid was dried under vacuum at 40° C. to give 1.72 g of the title compound (yield: 89%).

EXAMPLE 128

1-Furan-2-ylmethyl-6-methoxy-4-phenyl-phthalazine (Compound 77)

A solution under N$_2$ of ZnCl$_2$ in THF 0.5M (18.35 ml, 9.18 mmoles) was dropwise added under stirring at 0° C. with 2M phenyl lithium (4.37 ml, 8.74 mmoles). The mixture was left at room temperature for 1 hour, then sequentially added with 4-chloro-1-furan-2-ylmethyl-6-methoxy-phthalazine (1.2 g, 4.37 mmoles), prepared as described in example 127, palladium acetate (49 mg, 0.218 mmole) and triphenylphosphine (114.4 mg, 4.36 mmoles). The mixture was refluxed for 45 minutes, then diluted with ethyl acetate and washed with water. The organic phase was anhydrified over $Na_2SO_4$ and dried. The residue was flash chromatographed (eluent: petrolatum/ethyl acetate 1:1). The resultant oil was crystallised from ethyl ether (15 ml) to give 480 mg of the title compound (yield: 34%). m.p.: 128–129° C.

$^1$H-NMR (CDCl$_3$) δ: 8.14(d,1H,J=9.2 Hz); 7.76–7.50(m, 5H); 7.44(dd,1H,J=2.6 Hz); 7.31–17.29(m,2H); 6.28–6.25 (m, 1H); 6.10(d, 1H,J=3.3 Hz); 4.72(s,2H); 3.82(s,3H).

EXAMPLE 129

1-Furan-2-ylmethyl-6-methoxy-4-pyrrolidin-1-yl-phthalazine (Compound 78)

A solution of 4-chloro-1-furan-2-ylmethyl-6-methoxy-phthalazine (500 mg, 1.82 mmoles), prepared as described in example 127, in DMF (10 ml) was added under stirring with pyrrolidine (0.91 ml, 10.92 mmoles), and heated at 60° C. overnight. The mixture was diluted with ethyl acetate, washed three times with water, anhydrified over $Na_2SO_4$ and dried. The residue was crystallised from ethyl ether/petrolatum 1:1 (10 ml) to give 420 mg of the title compound (yield: 75%). m.p.: 148–149° C.

$^1$H-NMR (CDCl$_3$) δ: 7.91(d,1H,J=9.1 Hz); 7.48(d,H,J= 2.6 Hz); 7.34–7.26(m,2H); 6.24–6.21(m,1H); 6.01(d,1H,J= 3.3 Hz); 4.49(s,2H); 3.91(s,3H); 3.87–3.81(m,4H); 2.03–1.96(m,4H).

EXAMPLE 130

7-Methoxy-4-pyridin-4-ylmethyl-2H-phthalazin-1-one (Compound 79)

A solution of (5-methoxy-3-oxo-1,3-dihydro-isobenzofuran-1-yl)-triphenyl-phosphonium bromide (43,5 g, 0.0861 mole), prepared as described in example 36, and 4-pyridincarboxaldehyde (9.22 g, 0.0861 mole) in $CH_2Cl_2$ (300 ml) was dropwise added with triethylamine (12 ml, 0.0861 mole) while controlling the temperature in water bath. After 1 night under stirring at room temperature, the mixture was washed with water, discoloured, anhydrified and dried. The residue was suspended in $CH_3OH$ (135 ml) and added with hydrazine monohydrate (12.55 ml, 0.2583 mole). The mixture was refluxed for 1 hour, then cooled in water/ice, filtered and dried. The residue was crystallised in $CH_3OH$ to give 8 g of the title compound. The mother liquors were dried and the residue triturated in $CH_3OH$ (50 ml) to give further 3,5 g of the title compound (total yield: 50%).

$^1$H-NMR (DMSO) δ: 12.54(s,1H); 8.46–7.27(m,7H); 4.28(s,2H); 3.90(s,3H).

EXAMPLE 131

4-Chloro-4-methoxy-1-pyridin-4-ylmethyl-phthalazine

A suspension of 7-methoxy-4-pyridin-4-ylmethyl-2H-phthalazin-1-one (11.4 g, 42.65 mmoles), prepared as described in example 130, and POCl$_3$ (7.95 ml, 85.30 mmoles) in acetonitrile (110 ml) was refluxed for 1.5 hours. Further POCl$_3$ (40 ml) was added and the reflux was kept on overnight. The mixture was dried, dissolved in water, neutralised with $NaHCO_3$, extracted with $CH_2Cl_2$ and dried. The residue was chromatographed (eluent: $CH_2Cl_2/CH_3OH$ 97:3) to give 2.9 g of the title compound (yield: 23.8%).

$^1$H-NMR (CDCl$_3$) δ: 8.48—7.15(m,4H); 7.85–7.40(m, 3H); 4.62(s,2H); 4.00(s,3H).

EXAMPLE 132

6-Methoxy-1-pyridin-4-ylmethyl-4-pyrrolidin-1-ylphthalazine (Compound 80)

Operating analogously to what described in example 129, but under $N_2$ and starting from 4-chloro-6-methoxy-1-pyridin-4-ylmethyl-phthalazine (200 mg, 0.7 mmole), prepared as described in example 131, in DMF (5 ml) and pyrrolidine (0.17 ml, 2.1 mmoles), 180 mg of the title compound were obtained (yield: 65%).

$^1$H-NMR (DMSO) δ: 8.90–8.86(m,2H); 8.27(d,1H,J=9.1 Hz); 8.00–7.95(m,3H); 7.78(dd,1H,J=2.1 Hz); 4.88(s,2H); 4.05–3.96(m,4H); 4.02(s,3H); 2.09–2.02(m,4H).

EXAMPLE 133

3-[2-(2-Methoxy-ethoxy)-ethoxy]-propyne

A solution under $N_2$ of 2-(2-methoxy-ethoxy)ethanol (4.9 ml, 41.61 mmoles) in dry THF (50 ml) was portionwise added at room temperature under stirring with 60% NaH in oil (1.66 g, 41.61 mmoles). The mixture was stirred for 30 minutes then dropped into a solution of 80% 3-bromo-propyne in toluene (5.1 ml, 45.77 mmoles), and stirred for 1 hour, then diluted with ethyl ether, thrice washed with water, anhydrified over $Na_2SO_4$ and dried to give 5 g of the title compound as an oil (yield: 76%).

$^1$H-NMR (CDCl$_3$) δ: 4.18(d,2HJ=2.4 Hz); 3.71–3.51(m, 8H); 3.36(s,3H); 2.40(t,1H).

EXAMPLE 134

1-(3,5-Dichloro-pyridin-4-ylmethyl)-6-methoxy-5-{3-[2-(2-methoxy-ethoxy)-ethoxy]-prop1-ynyl}-phthalazine (Compound 81)

A suspension under $N_2$ of 3-[2-2-methoxy-ethoxy)-ethoxy]-propyne (810 mg, 5.12 mmoles), prepared as described in example 133, trifluoro-methanesulfonic acid 1-(3,5-dichloro-pyridin-4-ylmethyl)-6-methoxy-phthalazin-5-yl ester (2 g, 4.27 mmoles), prepared as described in example 73, and diethylamine (40 ml) was added under stirring with bis(triphenylphosphine) PdCl$_2$ (60 mg, 0.085 mmole) and CuI (16.18 mg, 0.085 mmole). The mixture was refluxed for 6 hours, then dried. The residue was flash chromatographed (eluent: ethyl acetate) to give a solid which was taken up in ethyl ether, filtered and dried under vacuum, at 40° C. to give 940 mg of the title compound (yield: 46%).

$^1$HNMR (DMSO) δ: 9.62(s,1H); 8.68(s,2H); 8.59–7.99 (2d,2H,J=9.3 Hz); 4.99(s,2H); 4.59(s,2H); 4.09(s,3H); 3.74–3.40(m,8H); 3.21(s,3H).

EXAMPLE 135

Benzyl-{3-[1-(3,5-dichloro-pyridin-4-ylmethyl)-6-methoxy-phthalazin-5-yl]-ally}-methyl-amine (Compound 82)

A solution of benzyl-{3-[1(3,5-dichloro-pyridin-4-ylmethyl)-6-methoxy-phthalazin-5-yl]-prop-2-ynyl}-methyl-amine (0.17 g, 0.36 mmoles), prepared as described in example 74, in THF (5 ml) and 10% Pd/C (0.07 g) was charged in a Parr apparatus at 2.7 atmospheres for 1.5 hours. The mixture was filtered over celite and dried to give an oil which was flash chromatographed (eluent: $CH_2Cl_2/CH_3OH/NH_3$ 98:2:0.2, then 98:2:0.5). The resultant oil was crystallised from isopropyl ether to give 0.105 g of the title compound (yield: 61%)

$^1$H-NMR (CDCl$_3$) δ: 9.40(s,1H); 8.51(s,2H); 8.17 and 7.62(2d,2H,J=9.2 Hz); 7.23–7.11 (m,5H); 6.65(dt,1H); 6.29 (dt,1H,J=11.5 Hz,J=6.6 Hz); 4.91(s,2H); 3.98(s,3H); 3.34(s, H); 2.83(dd,2H,J$_{2HH}$=1.65 Hz).

EXAMPLE 136

Methanesulfonic acid prop-2-ynyl ester

A solution of prop-2-yn-1-ol (5 g, 89.19 mmoles) in $CH_2Cl_2$ (25 ml) was cooled to 0–5°C. and added with triethylamine (13.6 ml, 98.11 mmoles) and with a solution of methanesulfonyl chloride (7.6 ml, 98.11 mmoles) in $CH_2Cl_2$ (20 ml). After 2 hours the mixture was put in a refrigerator overnight. The mixture was washed with water and the organic phase was dried to give 6.88 g of the title compound.

$^1$H-NMR ($CDCl_3$) δ: 4.82(d,2H,J=2.4 Hz); 3.11(s,3H); 2.68(t,1H).

EXAMPLE 137

4-Prop-2-ynyl-morpholine

A mixture of methanesulfonic acid prop-2-ynyl ester (3.44 g, 25.7 mmoles), prepared as described in example 136, morpholine (5.4 g) and $Na_2CO_3$ (3.3 g, 30.84 mmoles) in ethanol was stirred at room temperature for 6 hours. The solid was filtered off and the solution was concentrated and poured into water. The mixture was acidified with HCl, extracted with ethyl ether, alkalinised with $NaHCO_3$ and extracted with ethyl acetate. The organic phase was anhydrified over $Na_2SO_4$ and dried to give 3.87 g of the title compound which was used as such in the subsequent step.

EXAMPLE 138

1-(3,5-Dichloro-pyridin-4-ylmethyl)-6-methoxy-5-
(3-morpholin-4-yl-prop-1-ynyl)-phthalazine
(Compound 83)

Operating analogously to what described in example 74 starting from trifluoro-methanesulfonic acid 1-(3,5-dichloro-pyridin-4-ylmethyl)-6-methoxy-phthalazin-5-yl ester (2 g, 4.27 mmoles), prepared as described in example 73, 4-prop-2-ynyl-morpholine (640 mg, 5.12 mmoles), prepared as described in example 137, diethylamine (40 ml), bis(triphenylphosphine)$PdCl_2$ (60 mg, 0.0854 mmole) and CuI (16 mg, 0.0854 mmole), 728 mg of the title compound were obtained (yield: 38.6%).

$^1$H-NMR ($CDCl_3$) δ: 9.76(s,1H); 8.50(s,2H); 8.16 and 7.60(2d,2H); 4.88(s,2H); 4.08(s,3H); 3.80–3.75(m,4H); 3.72(s,2H); 2.73–2.68(m,4H).

EXAMPLE 139

6-Methoxy-5-trimethylsilanylethynyl-2H-phthalazin-1-one

A solution of trifluoro-methanesulfonic acid 6-methoxy-1-oxo-1,2-dihydro-phthalazin-5-yl ester (4.52 g, 13.94 mmoles), prepared as described in example 59, trimethylsilylethyne (3.94 ml, 27.88 mmoles), bis(triphenylphosphine)$PdCl_2$ (245 mg, 0.384 mmole) and triethylamine (6.56 ml) in DMF (30 ml) was heated at 60° C. for 4 hours. Further trimethylsilylethyne (2 ml) was added and the mixture was heated at 90° C. for 3 hours. After evaporation of the solvent, the residue was taken up in ethyl acetate and the solid was filtered off. After evaporation, the residue was taken up in diethylcarbonate, washed with water, dried, evaporated again, taken up in ethyl ether and filtered giving 2.87 g of the title compound (yield: 75.6%).

$^1$H-NMR (DMSO) δ: 12.70(s,1H); 8.33(s,1H); 8.22–7.58 (m,2H); 3.98(s,3H); 0.28(s,9H).

EXAMPLE 140

5-Ethynyl-6-methoxy-2H-phthalazin-1-one

A suspension of 6-methoxy-5-trimethylsilanylethynyl-2H-phthalazin-1-one (2.87 g, 10.20 mmoles), prepared as described in example 139, in acetonitrile (50 ml) was added with 32% NaOH (15 ml) and stirred at room temperature for 1 hour. The mixture was neutralised with concentrated HCl and the precipitate filtered off. The aqueous phase was extracted with ethyl acetate, the organic phase was dried and taken up in acetone. The solid was filtered off and joined to the previous precipitate to give 1.99 g of the title compound (yield: 97.3%).

$^1$H-NMR (DMSO) δ: 12.68(bs,1H); 8.37(s,1H); 8.24–7.60(m,2H); 4.82(s,1H); 4.00(s,3H).

EXAMPLE 141

6-methoxy-5-pyridin-4-ylethynyl-2H-phthalazin-1-one

A suspension of 5-ethynyl-6-methoxy-2H-phthalazin-1-one (1.9 g, 9.49 mmoles), prepared as described in example 140, 4-bromopyridine hydrochloride (2.214 g, 11.39 mmoles), bis(triphenylphosphine)$PdCl_2$ (133 mg, 0.1998 mmole) and CuI (36 mg, 0.1898 mmole) in diethylamine (40 ml) was heated at 75° C. for 1 hour, cooled, diluted with water (40 ml) and the solid was filtered after 30 minutes under stirring. The solid was suspended in acetone, stirred for 15 minutes, filtered again and dried in oven at 45° C. under vacuum giving 2.263 g of the title compound (yield: 86%).

$^1$H-NMR (DMSO) δ: 8.56(s,1H); 8.30–7.65(m,2H); 4.05 (s,3H).

EXAMPLE 142

1-Chloro-6-methoxy-5-pyridin-4-ylethynyl-phthalazine

A suspension under $N_2$ of 6-methoxy-5-pyridin-4-ylethynyl-2H-phthalazin-1-one (2.26 g,), prepared as described in example 141, in $POCl_3$ (40 ml) was heated for 3 hours at 85° C., then dried. The residue was taken up in a saturated $NaHCO_3$ solution up to alkalinity, then filtered and extracted with ethyl acetate. The solid was dissolved in a $CH_2Cl_2/CH_3OH$/ethyl acetate mixture, dried over $Na_2SO_4$ and filtered. The solution was joined to the previous organic phase and dried to give a residue which was taken up in acetone and filtered yielding 1.5 g of the title compound (yield: 62%).

$^1$H-NMR ($CDCl_3$) δ: 9.87(s,1H); 8.70–7.70(m,4H); 8.41–8.04(m,2H); 4.14(s,3H).

EXAMPLE 143

1-(3,5-Dichloro-pyridin-4-ylmethyl)-6-methoxy-5-
pyridin-4-ylethynyl-phthalazine (Compound 84)

Operating analogously to what described in example 15 starting from 1-chloro-6-methoxy-5-pyridin-4-ylethynyl-phthalazine (1.38 g, 4.66 mmoles), prepared as described in example 142, 3,5-dichloro-4-methylpyridine (1.887 mg, 11.65 mmoles), DMF (20 ml), NaH (466 mg, 11.65 mmoles), 793 mg of the title compound were obtained.

$^1$H-NMR ($CDCl_3$) δ: 9.83(s,1H); 8.68–8.64(m,2H); 8.52 (s,2H);8.25 and 7.66(2d,2H,J=9.3 Hz);7.51–7.48(m,2H); 4.91(s,2H); 4.15(s,3H).

EXAMPLE 144

3-(3,5-Dichloro-pyridin-4-ylmethylene)-6-methoxy-
1-thiazol-2-yl-1,3-dihydro-isobenzofuran-1-ol A milky solution of 2-bromothiazole (5.6 g, 34.2 mmoles) in dry ethyl ether (17 ml) was added dropwise to a solution of n-butyl lithium (14.4 ml, 36 mmoles) in dry ethyl ether (50 ml), under $N_2$ at −80° C. The reaction mixture was stirred at −80° C. for 15 minutes, then a solution of 3-(3,5-dichloro-pyridin-4-ylmethylene)-6-methoxy-3H-isobenzofuran-1-one (10 g, 31 mmoles), prepared as described in example 37, in dry THF (60 ml) was slowly added. After 45 minutes at −78° C., the resultant solution was treated with saturated $NH_4Cl$, with water and brought to room temperature. The aqueous phase was separated and extracted with ethyl acetate, decoloured with charcoal, filtered over celite and concentrated under vacuum. The resultant foam was flash cromatographed (eluent petrolatum:ethyl acetate 6:4) obtaining 4.64 g of the title compound (yield: 38%).

$^1$H-NMR (CDCl$_3$) δ: 8.42(s,2H); 7.88–6.80(m,3H); 7.77 (d,1H,J=3 Hz); 7.38(d,1H); 5.37(s, 1H); 3.87(s,1H); 3.83(s, 3H).

EXAMPLE 145

3-(3,5-Dichloro-1-oxy-pyridin-4-ylmethylene)-6-methoxy-1-thiazol-2-yl-1,3-dihydro-isobenzofuran-1-ol Under $N_2$, m-chloroperbenzoic acid (4.15 g, 13.2 mmoles) was added to a solution of 3-(3,5-dichloro-pyridin-4-ylmethylene)-6-methoxy-1-thiazol-2-yl-1,3-dihydro-isobenzofuran-1-ol (4.47 g, 11 mmoles), prepared as described in example 144, in CHCl$_3$ (45 ml) and the mixture was refluxed overnight. Further m-chloroperbenzoic acid (0.34 g) was added and the mixture was refluxed again, then cooled with ice. The solid was filtered and washed with CHCl$_3$ and with ethyl ether obtaining a crude solid. The mother liquors were washed with water, with Na$_2$S$_2$O$_5$ and with water/Na$_2$CO$_3$, decoloured with charcoal, filtered over celite and concentrated under vacuum. The resultant solid was joined to the previous one and flash chromatographed (eluent CH$_2$Cl$_2$:CH$_3$OH 95:5) obtaining a solid which was triturated in ethyl ether yielding 2.56 g of the title compound (yield: 55%). m.p. 230–233° C. (dec.)

$^1$H-NMR (DMSO) δ: 8.59–8.55(m,2H); 7.80–7.71(m, 2H); 7.77–6.82(m,3H); 7.33(s,1H); 5.22(s,1 H); 3.81(s,3H).

EXAMPLE 146

1-(3,5-Dichloro-1-oxy-pyridin-4-ylmethyl)-6-methoxy-4-thiazol-2-yl-phthalazine (Compound 85)

Acetic acid (1.68 g, 28 mmoles) and then hydrazine monohydrate (0.3 g, 5.88 mmoles) were added to a suspension of 3-(3,5-dichloro-1-oxy-pyridin-4-ylmethylene)6-methoxy-1-thiazol-2-yl-1,3-dihydro-isobenzofuran-1-ol (2.36 g, 5.6 mmoles), prepared as described in example 145. The mixture was refluxed for 5 hours, left to stand for 2 days, then refluxed again overnight. Further hydrazine monohydrate (5.88 mmoles) was added and the mixture was refluxed overnight, cooled with ice and filtered, washing with a lot of water. After drying at 60° C. under vacuum, the resultant solid was flash chromatographed (eluent ethyl acetate) obtaining a solid which was triturated in ethyl ether yielding 1.59 g of the title compound. m.p. 248.4–249.4° C. (dec.).

$^1$H-NMR (CDCl$_3$) δ: 9.35(d,2H,J=2.6 Hz); 8.22(s,2H); 8.14(d,1H,J=9.1 Hz); 8.06(d,1H,J=3.3 Hz); 7.61(dd,1H); 7.51(d,1H); 4.87(s,2H); 4.07(s,3H).

EXAMPLE 147

PDE 4 Enzyme Inhibition a) Human Polymorphonuclear Leukocyte Isolation

The polymorphonuclear leukocytes (PMNs) were isolated from peripheral blood of healthy volunteers according to Boyum A. (Scand. J. Immunol., 1976, 5th suppl., 9). Briefly, the PMNs were purified by Ficoll-Paque gradient centrifugation followed by sedimentation on dextran and the erythrocyte contamination was eliminated by hypotonic lysis.

b) PDE 4 Enzyme Purification

The human PMNs were suspended in TRIS/HCl buffer (10 mM, pH 7.8) containing MgCl$_2$ (5 mM), EGTA (4 mM), mercaptoethanol (5 mM), TRITON-X100 (1%), pepstatin A (1 μM), PMSF (100 μM) and leupeptin (1 μM), and homogenised by Polytron homogeniser. The homogenate was centrifuged at 25,000×g for 30 minutes at 4° C. and the PDE 4 enzyme was purified by ion exchange chromatography using the FPLC technique according to Schudt C. et al. (Naunyn-Schmidberg's Arch. Pharmacol., 1991, 334, 682). The supernatant was seeded on a UNO Q12 column (Bio-Rad) and the enzyme was eluted by sodium acetate linear gradient from 50 mM to 1M using a flow rate of 4.5 ml/minutes. The fractions containing enzymatic activity were pooled, dialysed against water and concentrated. The PDE 4 enzyme was stored at, −20° C. in the presence of ethylene glycol (30% v/v) until the use.

c) PDE 4 Activity Assay

The enzyme activity was evaluated with a Scintillation Proximity Assay (SPA) kit (Amersham). The enzymatic reaction was performed in a final volume of 100 μl of TRIS/HCl buffer (50 mM, pH 7.5), MgCl$_2$ (8.3 mM), EGTA (1.7 mM), cAMP (1 μM) and [$^3$H]cAMP (~100.000 dpm) as tracer. The compounds of the invention, the reference ones or the vehicle were added at different concentrations. As reference compounds 6,7-dimethoxy-4-pyridin-4-yl-methyl)2H-phthalazin-1-one (reference 1) and 6,7-dimethoxy-4-(piperidin-4-yl-methyl)2H-phthalazin-1-one (reference 2) embraced by the general formula of the patent application EP-0 722 936 (in the name of Eisai) were used. The reaction was started by adding 1.5 μg protein and incubated for 40 minutes at 30° C. SPA beads (50 μl) containing 18 mM zinc sulphate were added to stop the reaction and after 20 minutes at room temperature the radioactivity was measured using a scintillation counter.

The IC$_{50}$ value refers to the nanomolar concentration of the compound required to inhibit cyclic nucleotide hydrolysis by 50%, and it was calculated by non-linear regression analysis.

The compounds of formula I of the present invention are able to selectively inhibit PDE 4. The results are shown in the following Table 1.

TABLE 1

| Compound | IC$_{50}$ nM |
| --- | --- |
| 5 | 37 ± 6 |
| 8 | 51 ± 7 |
| 9 | 36 ± 4 |
| 10 | 28 ± 4 |
| 11 | 26 ± 3 |
| 12 | 30 ± 8 |
| 13 | 12 ± 2 |
| 15 | 21 ± 4 |
| 16 | 72 ± 16 |
| 17 | 131 ± 24 |
| 20 | 158 ± 34 |
| 22 | 225 ± 35 |

TABLE 1-continued

| Compound | IC$_{50}$ nM |
|---|---|
| 23 | 209 ± 26 |
| 24 | 36 ± 9 |
| 26 | 14 ± 2 |
| 27 | 48 ± 12 |
| 29 | 241 ± 73 |
| 32 | 10 ± 2 |
| 33 | 19 ± 3 |
| 35 | 7.1 ± 0.5 |
| 36 | 96.4 ± 7.3 |
| 37 | 61 ± 2.4 |
| 38 | 132 ± 30 |
| 55 | 312 ± 48 |
| 56 | 364 ± 67 |
| 60 | 93 ± 29 |
| Reference 1 | <100 μM |
| Reference 3 | <100 μM |

EXAMPLE 148

TNF$_\alpha$ Release Inhibition a) Human Monocyte Isolation

The monocytes were isolated from peripheral blood of healthy volunteers according to the procedure of Schreek L. et al. (J. Natl. Cancer Inst., 1964, 32, 507). The monocyte and lymphocyte population was isolated by Ficoll gradient centrifugation, and the cells diluted at a density of 2.5×10$^6$ cells/ml in RPMI1640 incubation medium containing 1% heat-inactivated foetal calf serum, penicillin (100 U/ml) and streptomycin (100 μg/ml) were plated in 24-wells plates (1 ml/well) and left to adhere for 1 hour at 37° C. with 5% CO$_2$. Non-adherent lymphocytes were removed by aspiration and the monocytes adhered to the plate were used in the next step.

b) TNF$_\alpha$ Release Assay

The TNF$_\alpha$ release from human monocytes was measured according to the method of Barnette M. et al. (Biochemical Pharmacology, 1996, 51, 949). The monocytes were incubated for 1 hour with 1 ml of RPMI1640 incubation medium (1% beat-inactivated foetal calf serum, 100 U/ml penicillin and 100 μg/ml streptomyc in) containing different concentrations of the products according to the present invention or the vehicle for the controls. The TNF$_\alpha$ release from monocytes was induced by adding 1 ng/ml of LPS (lipopolysaccharide from E. Coli) and after 16 hours of incubation at 37° C., 5% CO$_2$, the incubation medium was removed, centrifuged and the supernatant stored at −80° C. until TNF$_\alpha$ assay by ELISA kit (Amersham). The results are expressed as IC$_{50}$ following the same calculation explained in example 147.

TABLE 2

| Compound | IC$_{50}$ nM |
|---|---|
| 5 | 46 ± 15 |
| 8 | 48 ± 14 |
| 29 | 73 ± 21 |
| 38 | 62 ± 17 |
| 49 | 9.1 ± 2.9 |
| 56 | 260 ± 44 |

EXAMPLE 149

PDE 3 and PDE 5 Enzyme Inhibition a) Human Platelet Preparation

Human platelets were prepared from platelet rich plasma (PRP) obtained from healthy volunteers. The PRP was centrifuiged at 2,200 rpm for 15 minutes at 4° C. and the pellet was suspended in lysis solution (15 ml; 155 mM NH$_4$Cl, 10 mM KHCO$_3$ and 0.1 mM Na$_2$EDTA, pH=7.4) and incubated for 10 minutes on ice-bath to remove the erythrocyte contamination. After centrifugation at 1,400 rpm for 10 minutes at 4° C., platelets were suspended in 10 ml of 145 nM NaCl, 5 mM KCl, 1 mM MgSO$_4$, 10 mM glucose, 10 mM HEPES (pH 7.4) and 0.05 U/ml of hirudin, and stored at −20° C. until homogenisation. Platelets were thawed and 50 ml of 20 mM TRIS (pH=6.5) containing 5 mM β-mercapto-ethanol, 2 mM EDTA, 50 mM sodium acetate and 50 μM PMSF (homogenisation buffer) were added. The platelet suspension was then homogenised by a Polytron homogeniser (Polytron PT 1200) for 20 seconds. The homogenate was centrifuged at 14,500 rpm for 20 minutes at 4° C., and the supernatant was applied to an UNO Q12 column (Bio-Rad). The PDE 3 and PDE 5 were eluted by sodium acetate linear gradient from 0.05M to 1M using a flow rate of 4.5 ml/minutes. The fractions containing the enzymatic activities (PDE 3 or PDE 5) were pooled, dialysed against water and concentrated 10 times by ultrafiltration. The PDE 3 and PDE 5 fractions were stored at −20° C. in the presence of ethylene glycol (30% v/v) until use.

b) PDE 3 and PDE 5 Activity Assay

The enzyme activity was evaluated with a Scintillation Proximity Assay (SPA) kit (Amersham). The enzymatic reaction was performed in a final volume of 100 μl of TRIS/HCl buffer (50 mM, pH7.5), MgCl$_2$ (8.3 mM), EGTA (1.7 mM), cAMP (for PDE 3 assay) or cGMP (for PDE 5 assay) (1 μM), [$^3$H]cAMP or [$^3$H]cGMP (10 μl), and 10 μl of the compounds of the invention or vehicle. The reaction was started by adding the enzyme (1.0 μg) and incubated for 40 minutes at 30° C. SPA beads (50 μl) containing 18 mM zinc sulphate were added to stop the reaction and after 20 minutes at room temperature the radioacticity was measured using a scintillation counter.

The compounds were tested at 10$^{-6}$M and the results are expressed as percent of inhibition.

TABLE 3

| Compound | PDE 3 % inhibition at 10$^{-6}$ M | PDE 5 % inhibition at 10$^{-6}$ M |
|---|---|---|
| 5 | 7 | 21 |
| 8 | 12 | 35 |
| 11 | 17 | 10 |
| 15 | 15 | 0 |
| 17 | 12 | 21 |
| 20 | 5 | 11 |
| 22 | 20 | 8 |
| 23 | 19 | 21 |
| 26 | — | 0 |
| 27 | 15 | 9 |
| 29 | −4 | 1 |
| 38 | −2 | 1 |
| 49 | −10 | 10 |
| 54 | 2 | 33 |
| 56 | −9 | 14 |
| 60 | −2 | 1 |

What is claimed is:

1. A compound of formula

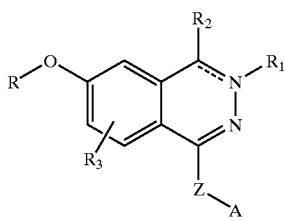

(I)

wherein

=== is a single or double bond;

Z is NH, methylene, a ($C_2$–$C_6$) alkylene chain optionally branched and/or unsaturated and/or interrupted by a ($C_5$–$C_7$) cycloalkyl residue;

A is phenyl or heterocycle optionally substituted by one or more substituent(s) selected among oxo, nitro, carboxy groups and halogen atoms, or A is a $COR_4$ group wherein $R_4$ is hydroxy, ($C_1$–$C_6$) alkoxy, amino optionally substituted by one or two ($C_1$–$C_6$) alkyl group(s) or by hydroxy;

R is a ($C_1$–$C_6$) alkyl or polyluoro ($C_1$–$C_6$) alkyl group;

$R_1$ is absent when === is a double bond or, when === single bond, is a) hydrogen;

b) ($C_1$–$C_6$) alkyl optionally substituted by aryl, by heterocycle or by a $COR_5$ group wherein $R_5$ is hydroxy, ($C_1$–$C_4$) alkoxy or hydroxyamino;

c) —$COR_6$ wherein $R_6$ is hydrogen, aryl, aryl-($C_1$–$C_6$) alkyl, amino optionally alkylated or monohydroxylated, hydroxy, ($C_1$–$C_4$) alkoxy, carboxy, ($C_1$–$C_4$) alkoxycarbonyl,

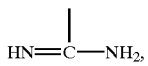

or ($C_1$–$C_4$) alkyl optionally substituted by heterocycle;

d) ($C_1$–$C_4$) alkylsulfonyl;

$R_2$ represents two hydrogen atoms or a group =O when === is a single bond, or, when === is a double bond, $R_2$ is hydrogen, cyano, ($C_1$–$C_4$) alkoxycarbonyl, amido, optionally substituted aryl or heterocycle, ($C_1$–$C_8$) alkyl, ($C_2$–$C_8$) alkenyl or ($C_2$–$C_8$) alkynyl optionally branched and/or substituted by aryl or heterocycle; aryloxy, heterocyclyloxy, aryl-($C_1$–$C_4$)-alkoxy, heterocyclyl-($C_1$–$C_4$) alkoxy, amino substituted by one or two ($C_1$–$C_4$) alkyl group(s), arylamino, heterocyclylamino, aryl-($C_1$–$C_4$) alkylamino, heterocyclyl-($C_1$–$C_4$)-alkylamino;

$R_3$ is hydrogen, or a ($C_1$–$C_8$) alkyl, ($C_2$–$C_8$) alkenyl or ($C_2$–$C_8$) alkynyl group optionally substituted by hydroxy, oxo, aryl or heterocycle, and optionally interrupted by one or more heteroatom(s) or heterogroup(s);

the N→O derivatives of the compounds of formula I and the pharmaceutically acceptable salts thereof.

2. A compound according to claim 1 wherein === is a double or single bond; and Z is methylene or a ($C_2$–$C_6$) alkylene chain.

3. A compound according to claim 1 wherein === is a double or single bond; Z is methylene or a ($C_2$–$C_6$)alkylene chain; and A is a heterocycle optionally substituted by one or more substituent(s).

4. A compound according to claim 1 wherein === is a double or single bond; Z is methylene; and A is pyridine substituted by two substituents.

5. A compound of formula

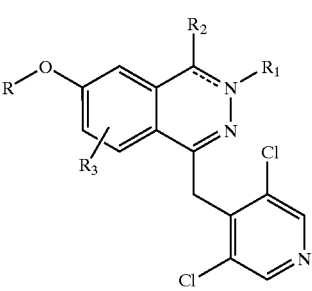

(I-A)

wherein

=== is a single or double bond;

R is a ($C_1$–$C_6$) alkyl or polyfluoro ($C_1$–$C_6$) alkyl group;

$R_1$ is absent when === is a double bond or, when === is a single bond, is a) hydrogen;

b) ($C_1$–$C_6$) alkyl optionally substituted by aryl, by heterocycle or by a $COR_5$ group wherein $R_5$ is hydroxy, ($C_1$–$C_4$) alkoxy or hydroxyamino;

c) —$COR_6$ wherein $R_6$ is hydrogen, aryl, aryl-($C_1$–$C_6$) alkyl, amino optionally alkylated or monohydroxylated, hydroxy, ($C_1$–$C_4$) alkoxy, carboxy, ($C_1$–$C_4$) alkoxycarbonyl,

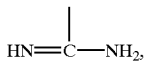

or ($C_1$–$C_4$) alkyl optionally substituted by heterocycle;

d) ($C_1$–$C_4$) alkylsulfonyl;

$R_2$ represents two hydrogen atoms or a group =O when === is a single bond, or, when === is a double bond, $R_2$ is hydrogen, cyano, ($C_1$–$C_4$) alkoxycarbonyl, amido,=optionally substituted aryl or heterocycle, ($C_1$–$C_8$) alkyl, ($C_2$–$C_8$) alkenyl or ($C_2$–$C_8$) alkynyl optionally branched and/or substituted by aryl or heterocycle; aryloxy, heterocyclyloxy, aryl-($C_1$–$C_4$)-alkoxy, heterocyclyl-($C_1$–$C_4$) alkoxy, amino substituted by one or two ($C_1$–$C_4$) alkyl group(s), arylamino, heterocyclylamino, aryl-($C_1$–$C_4$) alkylamino, heterocyclyl-($C_1$–$C_4$)-alkylamino;

$R_3$ is hydrogen, or a ($C_1$–$C_8$) alkyl, ($C_2$–$C_8$) alkenyl or ($C_2$–$C_8$) alkynyl group optionally substituted by hydroxy, oxo, aryl or heterocycle, and optionally interrupted by one or more heteroatom(s) or heterogroup(s);

the N→O derivatives of the compounds of formula I-A and the pharmaceutically acceptable salts thereof.

6. A compound according to claim 5 wherein === is a single bond and $R_2$ represents two hydrogen atoms.

7. A compound according to claim 5 wherein === is a double bond; and $R_2$ is cyano, ($C_1$–$C_4$)alkoxycarbonyl, amido, optionally substituted heterocycle, ($C_2$–$C_8$)alkenyl or ($C_2$–$C_8$)-alkynyl optionally substituted by aryl or heterocycle; aryloxy, heterocyclyloxy, arylamino, heterocyclylamino.

8. A compound according to claim 7 of formula

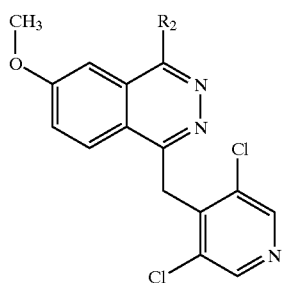

(I-B)

wherein R₂ is a heterocycle.

9. A compound according to claim 1, wherein heterocycle is independently selected from the group consisting of pyrrole, imidazole, pyrazole, pyridine, pyrazine, pyrimidine, pyridazine, piperazine, triazole, morpholine, pyrrolidine, pyrroline, imidazoline, pyrazoline, pyrazolidine, imidazolidine, piperidine, furan, pyran, thiazole, isothiazole, isoxazole, and thiophene.

10. A compound according to claim 5, wherein heterocycle is independently selected from the group consisting of pyrrole, imidazole, pyrazole, pyridine, pyrazine, pyrimidine, pyridazine, piperazine, triazole, morpholine, pyrrolidine, pyrroline, imidazoline, pyrazoline, pyrazolidine, imidazolidine, piperidine, furan, pyran, thiazole, isothiazole, isoxazole, and thiophene.

11. A pharmaceutical composition containing a therapeutically effective amount of a compound according to claim 1 in admixture with a suitable carrier.

12. A pharmaceutical composition according to claim 11, wherein heterocycle is independently selected from the group consisting of pyrrole, imidazole, pyrazole, pyridine, pyrazine, pyrimidine, pyridazine, piperazine, triazole, morpholine, pyrrolidine, pyrroline, imidazoline, pyrazoline, pyrazolidine, imidazolidine, piperidine, furan, pyran, thiazole, isothiazole, isoxazole, and thiophene.

13. A pharmaceutical composition containing a therapeutically effective amount of a compound according to claim 5 in admixture with a suitable carrier.

14. A method for the treatment of allergic and inflammatory diseases comprising administering the pharmaceutical composition according to claim 11 to a patient in need thereof.

15. A method for the treatment of respiratory diseases comprising administering the pharmaceutical composition according to claim 11 to a patient in need thereof.

16. A method for the treatment of allergic and inflammatory diseases comprising administering the pharmaceutical composition according to claim 13 to a patient in need thereof.

17. A method for the treatment of respiratory diseases comprising administering the pharmaceutical composition according to claim 13 to a patient in need thereof.

* * * * *